United States Patent
Wang et al.

(10) Patent No.: US 7,473,843 B2
(45) Date of Patent: *Jan. 6, 2009

(54) MAGNETIC RESONANCE IMAGING COATED ASSEMBLY

(75) Inventors: Xingwu Wang, Wellsville, NY (US); Howard J. Greenwald, Rochester, NY (US); Jeffrey L. Helfer, Webster, NY (US); Robert W. Gray, Rochester, NY (US); Michael L. Weiner, Webster, NY (US)

(73) Assignee: Biophan Technologies, Inc., Pittsford, NY (US)

( * ) Notice: Subject to any disclaimer, the term of this patent is extended or adjusted under 35 U.S.C. 154(b) by 447 days.

This patent is subject to a terminal disclaimer.

(21) Appl. No.: 11/331,928

(22) Filed: Jan. 13, 2006

(65) Prior Publication Data

US 2006/0118319 A1   Jun. 8, 2006

Related U.S. Application Data

(63) Continuation of application No. 10/838,116, filed on May 3, 2004, now abandoned, which is a continuation-in-part of application No. 10/384,288, filed on Mar. 7, 2003, now Pat. No. 6,765,144, which is a continuation of application No. 10/324,773, filed on Dec. 18, 2002, now Pat. No. 6,864,418, and a continuation of application No. 10/313,847, filed on Dec. 7, 2002, now Pat. No. 6,980,865, and a continuation of application No. 10/303,264, filed on Nov. 25, 2002, now Pat. No. 6,713,671, and a continuation of application No. 10/273,738, filed on Oct. 18, 2002, now Pat. No. 6,906,256, and a continuation of application No. 10/260,247, filed on Sep. 30, 2002, now Pat. No. 6,673,999, and a continuation of application No. 10/242,696, filed on Sep. 13, 2002, now abandoned, and a continuation of application No. 10/229,183, filed on Aug. 26, 2002, now Pat. No. 6,876,886, and a continuation of application No. 10/090,553, filed on Mar. 4, 2002, now Pat. No. 6,930,242, and a continuation of application No. 10/054,407, filed on Jan. 22, 2002, now Pat. No. 6,506,972.

(51) Int. Cl.
*H01B 11/06* (2006.01)
(52) U.S. Cl. ...................................................... 174/36
(58) Field of Classification Search ................... 174/36, 174/102 SC; 333/12; 606/194
See application file for complete search history.

(56) References Cited

U.S. PATENT DOCUMENTS

| 3,739,770 A | 6/1973 | Mori |
| 3,901,741 A | 8/1975 | Benz |
| 3,946,727 A | 3/1976 | Okada |
| 3,995,623 A | 12/1976 | Blake |
| 4,061,824 A | 12/1977 | Deffeyes |
| 4,166,263 A | 8/1979 | Harada |

(Continued)

*Primary Examiner*—Chau N Nguyen

(57) ABSTRACT

An assembly for shielding an implanted medical device from the effects of high-frequency radiation and for emitting magnetic resonance signals during magnetic resonance imaging. The assembly includes an implanted medical device and a magnetic shield comprised of nanomagnetic material disposed between the medical device and the high-frequency radiation. In one embodiment, the magnetic resonance signals are detected by a receiver, which is thus able to locate the implanted medical device within a biological organism.

11 Claims, 60 Drawing Sheets

U.S. PATENT DOCUMENTS

| | | |
|---|---|---|
| 4,168,481 A | 9/1979 | Harada |
| 4,169,998 A | 10/1979 | Harada |
| 4,180,600 A | 12/1979 | Feldstein |
| 4,241,521 A | 12/1980 | Dufresne |
| 4,246,586 A | 1/1981 | Henderson |
| 4,327,711 A | 5/1982 | Takagi |
| 4,449,097 A | 5/1984 | Young |
| 4,631,613 A | 12/1986 | French |
| 4,641,917 A | 2/1987 | Glodis |
| 4,646,723 A | 3/1987 | Arakawa |
| 4,671,292 A | 6/1987 | Matzuk |
| 4,705,353 A | 11/1987 | Wagoner |
| 4,705,613 A | 11/1987 | French |
| 4,731,239 A | 3/1988 | Gordon |
| 4,733,189 A | 3/1988 | Punchard |
| 4,738,880 A | 4/1988 | Asada |
| 4,741,953 A | 5/1988 | Katsuta |
| 4,749,560 A | 6/1988 | Elgavish |
| 4,770,183 A | 9/1988 | Groman |
| 4,778,714 A | 10/1988 | Woolley |
| 4,827,945 A | 5/1989 | Groman |
| 4,860,221 A | 8/1989 | Sato |
| 4,863,715 A | 9/1989 | Jacobsen |
| 4,868,015 A | 9/1989 | Shishido |
| 4,935,833 A | 6/1990 | Shiba |
| 4,939,610 A | 7/1990 | Narishige |
| 4,951,674 A | 8/1990 | Zanakis |
| 4,969,458 A | 11/1990 | Wiktor |
| 4,989,608 A | 2/1991 | Ratner |
| 5,003,975 A | 4/1991 | Hafelfinger |
| 5,005,585 A | 4/1991 | Mazza |
| 5,006,402 A | 4/1991 | Isayev |
| 5,013,717 A | 5/1991 | Solomon |
| 5,023,072 A | 6/1991 | Cheng |
| 5,041,083 A | 8/1991 | Tsuchida |
| 5,049,393 A | 9/1991 | Noon |
| 5,055,288 A | 10/1991 | Lewis |
| 5,058,567 A | 10/1991 | Takahashi |
| 5,069,216 A | 12/1991 | Groman |
| 5,098,737 A | 3/1992 | Collins |
| 5,142,017 A | 8/1992 | Sugimoto |
| 5,154,179 A | 10/1992 | Ratner |
| 5,161,030 A | 11/1992 | Song |
| 5,176,138 A | 1/1993 | Thacker |
| 5,178,739 A | 1/1993 | Barnes |
| 5,178,803 A | 1/1993 | Tsuchida |
| 5,184,074 A | 2/1993 | Arakawa |
| 5,211,183 A | 5/1993 | Wilson |
| 5,213,851 A | 5/1993 | Snyder |
| 5,228,438 A | 7/1993 | Buchanan |
| 5,260,132 A | 11/1993 | Nakazumi |
| 5,307,814 A | 5/1994 | Kressel |
| 5,315,365 A | 5/1994 | Hakimi |
| 5,329,232 A | 7/1994 | Gilderdale |
| 5,332,972 A | 7/1994 | Takenouchi |
| 5,335,663 A | 8/1994 | Oakley |
| 5,398,690 A | 3/1995 | Batten |
| 5,417,718 A | 5/1995 | Kleks |
| 5,431,691 A | 7/1995 | Snell |
| 5,437,283 A | 8/1995 | Ranalletta |
| 5,443,496 A | 8/1995 | Schwartz |
| 5,451,232 A | 9/1995 | Rhinehart |
| 5,452,726 A | 9/1995 | Burmeister |
| 5,456,692 A | 10/1995 | Smith |
| 5,460,187 A | 10/1995 | Daigle |
| 5,462,053 A | 10/1995 | Briggs |
| 5,476,095 A | 12/1995 | Schnall |
| 5,494,039 A | 2/1996 | Onik |
| 5,506,559 A | 4/1996 | Yamaguchi |
| 5,540,959 A | 7/1996 | Wang |
| 5,543,070 A | 8/1996 | Ishiyama |
| 5,567,673 A | 10/1996 | Face |
| 5,568,051 A | 10/1996 | Yamagata |
| 5,569,506 A | 10/1996 | Jahnes |
| 5,581,224 A | 12/1996 | Yamaguchi |
| 5,588,443 A | 12/1996 | Davidson |
| 5,643,670 A | 7/1997 | Chung |
| 5,645,910 A | 7/1997 | Burns |
| 5,658,470 A | 8/1997 | Schultz |
| 5,667,924 A | 9/1997 | Ziolo |
| 5,697,956 A | 12/1997 | Bornzin |
| 5,697,959 A | 12/1997 | Poore |
| 5,708,359 A | 1/1998 | Gregory |
| 5,714,136 A | 2/1998 | Yahagi |
| 5,731,045 A | 3/1998 | Dearnaley |
| 5,736,488 A | 4/1998 | Face |
| 5,744,958 A | 4/1998 | Werne |
| 5,768,123 A | 6/1998 | Maxemchuk |
| 5,779,637 A | 7/1998 | Palkovich |
| 5,783,570 A | 7/1998 | Yokota |
| 5,788,717 A | 8/1998 | Mann |
| 5,797,857 A | 8/1998 | Obitsu |
| 5,817,017 A | 10/1998 | Young |
| 5,824,761 A | 10/1998 | Bujanowski |
| 5,825,448 A | 10/1998 | Bos |
| 5,827,997 A | 10/1998 | Chung |
| 5,853,394 A | 12/1998 | Tolkoff |
| 5,867,027 A | 2/1999 | Kawamoto |
| 5,872,861 A | 2/1999 | Makram-Ebeid |
| 5,874,831 A | 2/1999 | Yi |
| 5,889,091 A | 3/1999 | Ziolo |
| 5,903,693 A | 5/1999 | Brown |
| 5,909,119 A | 6/1999 | Zhang |
| 5,913,005 A | 6/1999 | Terasawa |
| 5,938,623 A | 8/1999 | Quiachon |
| 5,946,439 A | 8/1999 | Terasawa |
| 5,964,730 A | 10/1999 | Williams |
| 5,964,757 A | 10/1999 | Ponzi |
| 5,967,223 A | 10/1999 | Kagan |
| 5,968,091 A | 10/1999 | Pinchuk |
| 5,984,005 A | 11/1999 | Hart |
| 6,001,068 A | 12/1999 | Uchino |
| 6,017,338 A | 1/2000 | Brucker |
| 6,019,736 A | 2/2000 | Avellanet |
| 6,019,737 A | 2/2000 | Murata |
| 6,037,016 A | 3/2000 | Devlin |
| 6,046,398 A | 4/2000 | Foote |
| 6,046,591 A | 4/2000 | King |
| 6,055,714 A | 5/2000 | Sproul |
| 6,082,760 A | 7/2000 | Ukai |
| 6,087,025 A | 7/2000 | Dearnaley |
| 6,093,157 A | 7/2000 | Chandrasekaran |
| 6,117,064 A | 9/2000 | Apple |
| 6,130,220 A | 10/2000 | Broka |
| 6,168,604 B1 | 1/2001 | Cano |
| 6,171,240 B1 | 1/2001 | Young |
| 6,171,295 B1 | 1/2001 | Garabedian |
| 6,175,655 B1 | 1/2001 | George |
| 6,181,232 B1 | 1/2001 | Kitamura |
| 6,190,379 B1 | 2/2001 | Heuser |
| 6,190,404 B1 | 2/2001 | Palmaz |
| 6,203,777 B1 | 3/2001 | Schroder |
| 6,203,864 B1 | 3/2001 | Zhang |
| 6,208,881 B1 | 3/2001 | Champeau |
| 6,235,024 B1 | 5/2001 | Tu |
| 6,238,408 B1 | 5/2001 | Kawabata |
| 6,245,053 B1 | 6/2001 | Benjamin |
| 6,248,092 B1 | 6/2001 | Miraki |
| 6,257,512 B1 | 7/2001 | Schoeck |
| 6,258,080 B1 | 7/2001 | Samson |
| 6,263,229 B1 | 7/2001 | Atalar |
| 6,265,466 B1 | 7/2001 | Glatkowski |
| 6,270,477 B1 | 8/2001 | Bagaoisan |
| 6,283,959 B1 | 9/2001 | Lalonde |

| | | |
|---|---|---|
| 6,305,436 B1 | 10/2001 | Andersen |
| 6,309,412 B1 | 10/2001 | Lau |
| 6,312,460 B2 | 11/2001 | Drasler |
| 6,315,794 B1 | 11/2001 | Richter |
| 6,324,427 B1 | 11/2001 | Florio |
| 6,342,068 B1 | 1/2002 | Thompson |
| 6,342,134 B1 | 1/2002 | Barber |
| 6,345,112 B1 | 2/2002 | Summers |
| 6,361,759 B1 | 3/2002 | Frayne |
| 6,361,861 B2 | 3/2002 | Gao |
| 6,375,330 B1 | 4/2002 | Mihalakis |
| 6,377,835 B1 | 4/2002 | Schoenberg |
| 6,390,443 B1 | 5/2002 | Katayama |
| 6,414,487 B1 | 7/2002 | Anand |
| 6,426,994 B1 | 7/2002 | Van Vaals |
| 6,438,229 B1 | 8/2002 | Overy |
| 6,445,006 B1 | 9/2002 | Brandes |
| 6,445,182 B1 | 9/2002 | Dean |
| 6,451,207 B1 | 9/2002 | Sterman |
| 6,454,910 B1 | 9/2002 | Zhurin |
| 6,457,350 B1 | 10/2002 | Mitchell |
| 6,459,922 B1 | 10/2002 | Zhang |
| 6,463,167 B1 | 10/2002 | Feldman |
| 6,486,671 B1 | 11/2002 | King |
| 6,506,972 B1 | 1/2003 | Wang |
| 6,765,144 B1 | 7/2004 | Wang |
| 2001/0016611 A1 | 8/2001 | Kashiwabara |
| 2002/0038135 A1 | 3/2002 | Connelly |
| 2002/0176822 A1 | 11/2002 | Frayne |

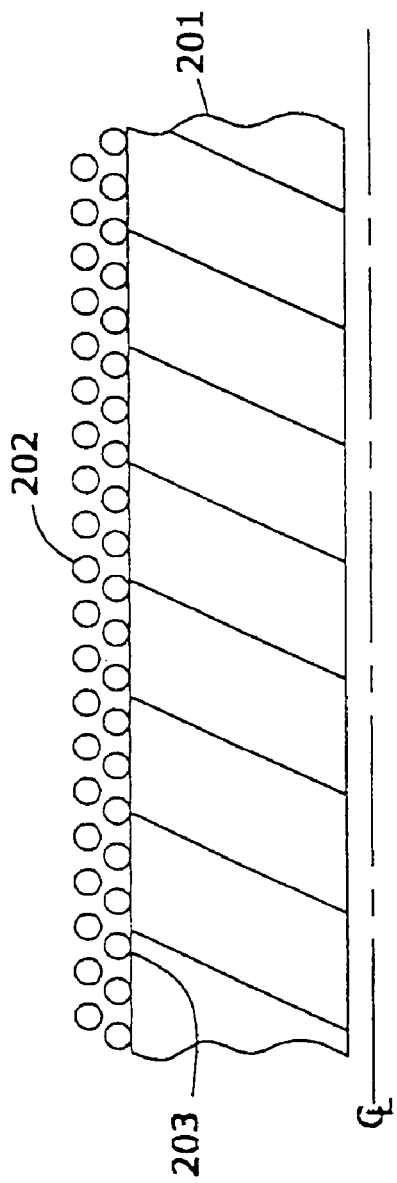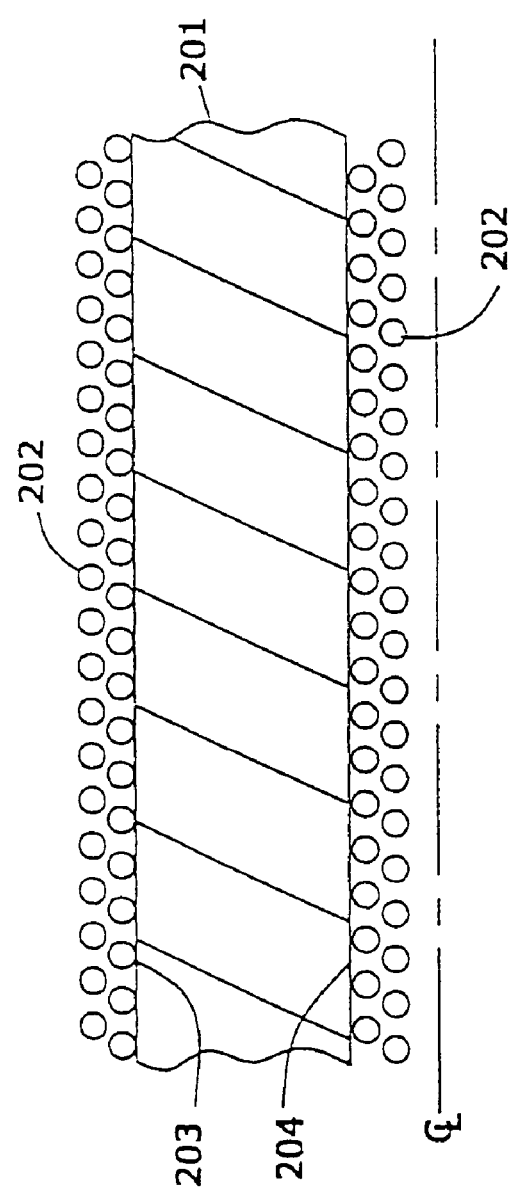

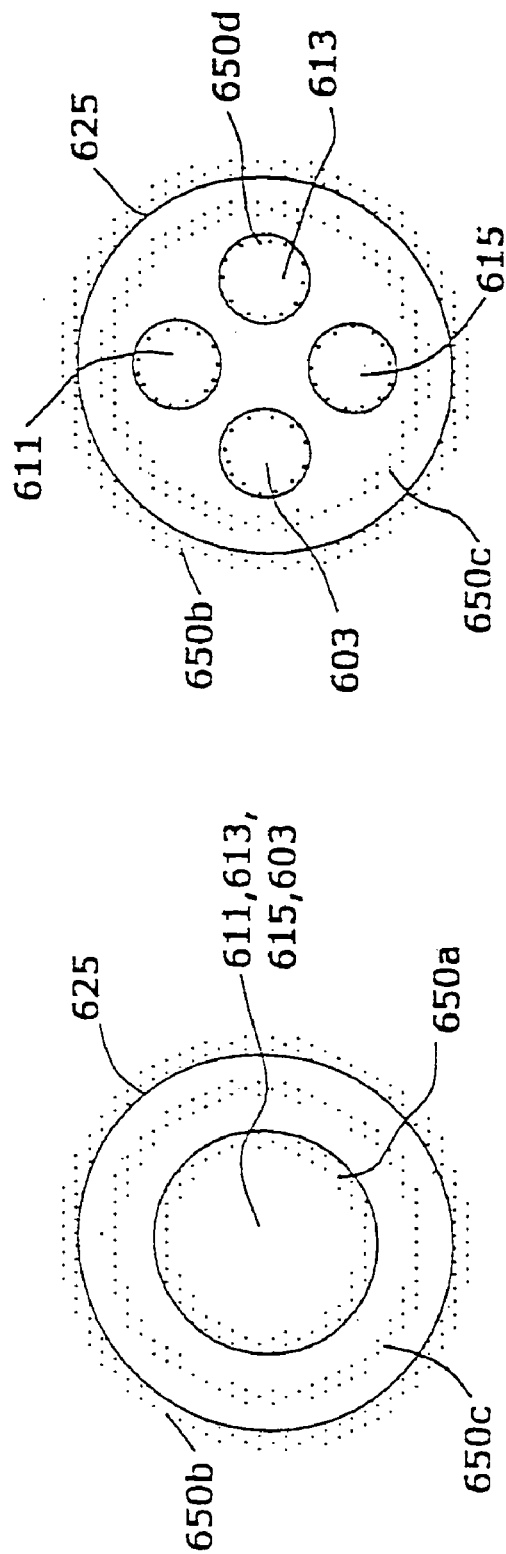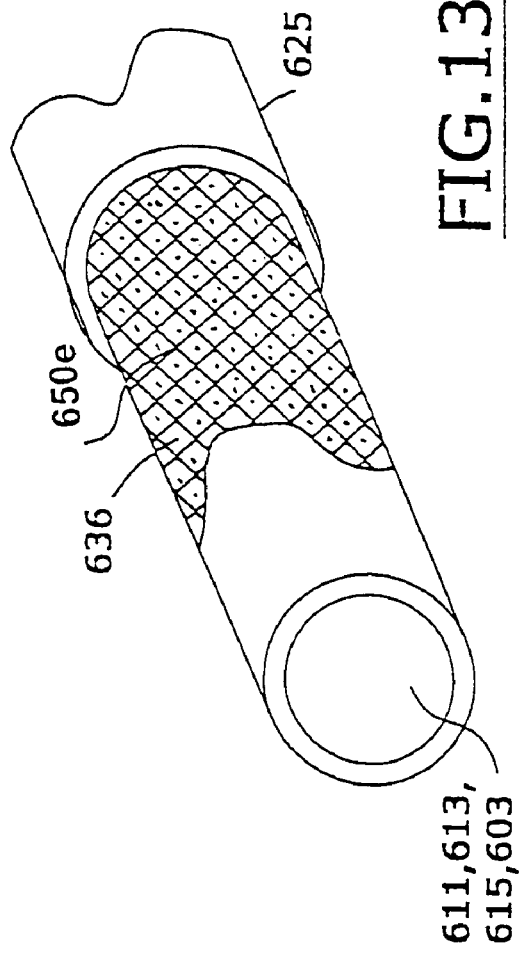
FIG.13A
FIG.13B
FIG.13C

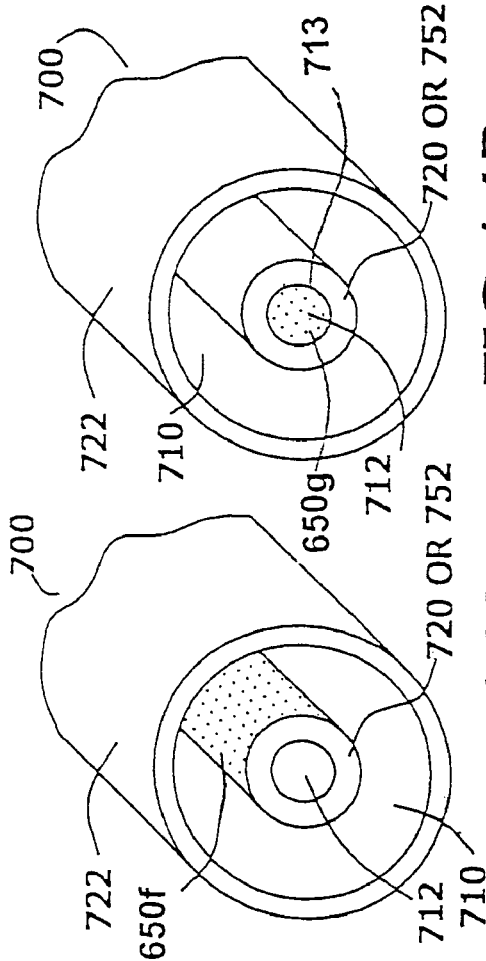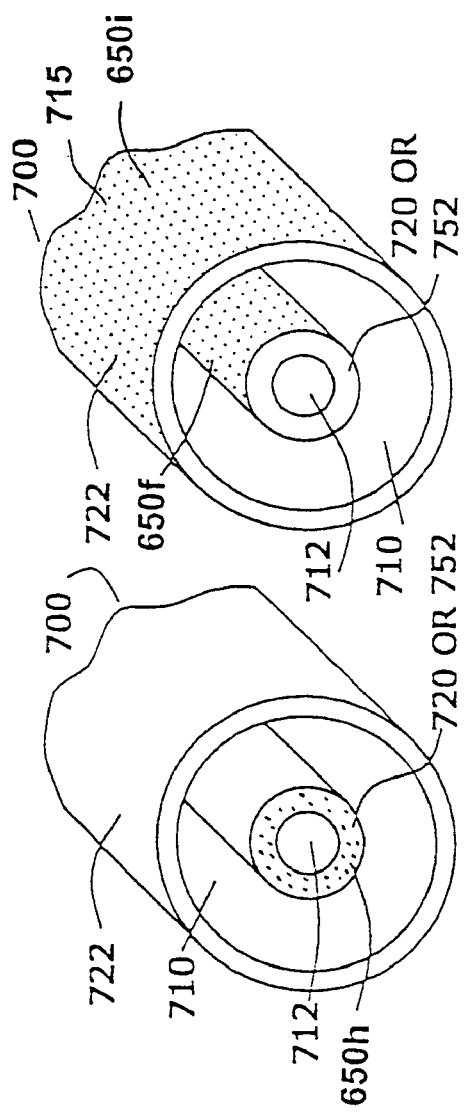

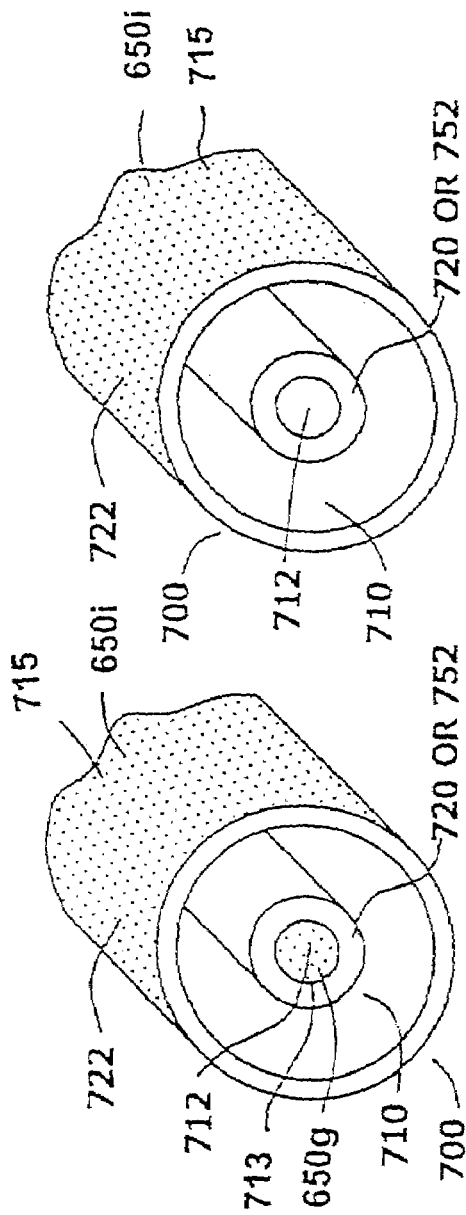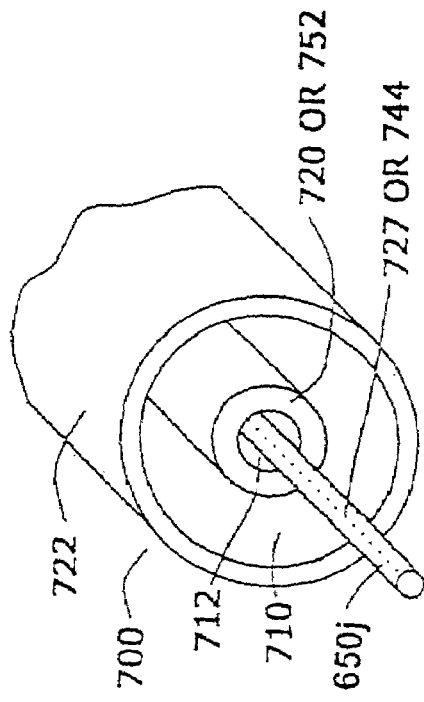

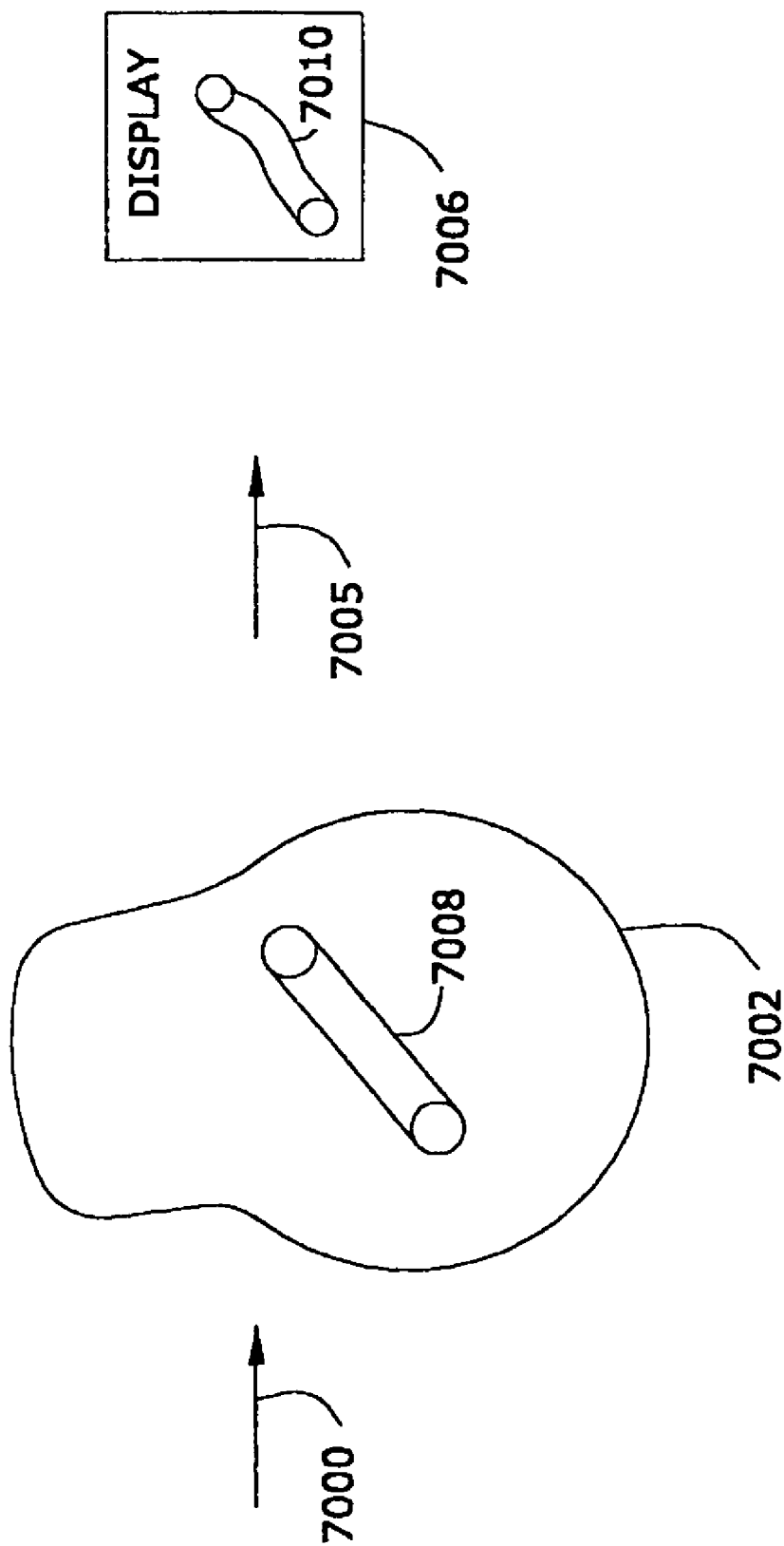

MAGNETIC RESONANCE IMAGING COATED ASSEMBLY

CROSS-REFERENCE TO RELATED PATENT APPLICATIONS

This application is a continuation of patent application Ser. No. 10/838,116 (filed May 3, 2004) which is a continuation-in-part of Ser. No. 10/384,288 (filed Mar. 7, 2003, now U.S. Pat. No. 6,765,144), which is a continuation of co-pending application Ser. No. 10/324,773 (filed Dec. 18, 2002), Ser. No. 10/313,847 (filed Dec. 7, 2002), Ser. No. 10/303,264 (filed Nov. 25, 2002, now U.S. Pat. No. 6,713,671), Ser. No. 10/273,738 (filed Oct. 18, 2002), Ser. No. 10/260,247 (filed Sep. 30, 2002, now U.S. Pat. No. 6,673,999), Ser. No. 10/242,969 (filed Sep. 13, 2002), Ser. No. 10/229,183 (filed Aug. 26, 2002), Ser. No. 10/090,553 (filed Mar. 4, 2002), and Ser. No. 10/054,407 (filed Jan. 22, 2002, now U.S. Pat. No. 6,506,972), all incorporated by reference as if fully written out below.

FIELD OF THE INVENTION

An assembly for imaging an implanted medical device, wherein the medical device is shielded by nanomagnetic material which, in addition to shielding the medical device from high-frequency electromagnetic radiation, emits high frequency electromagnetic radiation.

BACKGROUND OF THE INVENTION

Magnetic resonance imaging ("MRI") has been developed as an imaging technique adapted to obtain both images of anatomical features of human patients as well as some aspects of the functional activities and characteristics of biological tissue. These images have medical diagnostic value in determining the state of health of the tissue examined. Unlike the situation with fluoroscopic imaging, a patient undergoing magnetic resonance imaging procedure may remain in the active-imaging system for a significant amount of time, e.g. a half-hour or more, without suffering any adverse effects.

In an MRI process, a patient is typically aligned to place the portion of the patient's anatomy to be examined in the imaging volume of the MRI apparatus. Such an MRI apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). As is known to those skilled in the art, a magnetic field gradient ($\Delta B_0/\Delta x_i$) refers to the variation of the field with respect to each of the three principal Cartesian axes, $x_i$. The MRI apparatus also comprises one or more RF (radio frequency) coils which provide excitation and detection of the MRI signal. Additionally, or alternatively, detection coils may be designed into the distal end of a catheter to be inserted into a patient. When such catheters are employed, their proximal ends are connected to the receiving signal input channel of the magnetic resonance imaging device. The detected signal is transmitted along the length of the catheter from the receiving antenna and/or receiving coil in the distal end to the MRI input channel connected at the proximal end. Other components of an MRI system are the programmable logic unit and the various software programs which the programmable logic unit executes. Construction of an image from the received signals is performed by the software of the MRI system.

The insertion of metallic wires into a biological organism (such as, e.g., catheters and guidewires) while the organism is in a magnetic resonance imaging environment poses potentially deadly hazards to the organism through excessive heating of the wires. In some studies, heating to a temperature in excess of 74 degrees Centigrade has created such hazards; see, e.g., an article by M. K. Konings, et al., in "Catheters and Guidewires in Interventional MRI: Problems and Solutions", MEDICA MUNDI 45/1 March 2001.

The Konings et al. article lists three ways in which conductors may heat up in such environments: 1) eddy currents, 2) induction loops, and 3) resonating RF transverse electromagnetic (TEM) waves along the length of the conductors. It is disclosed in this article that: "Because of the risks associated with metal guidewires, and catheters with metal conductors, in the MRI environment, there is an urgent need for a non-metallic substitute, both for guidewires and for signal transfer." The authors further propose the use of " . . . a full-glass guidewire with a protective polymer coating . . . "

However, the use of such " . . . full glass guidewire . . . " presents its own problems. Many medical devices (such as, e.g., guides wires, stents, etc.) require some degree of strength and flexibility that is not afforded by glass guidewires and that typically require the use of metal or metal alloys in the device. The implementation of glass guidewires, optical fibers, etc., solutions would require substantial retooling of the, for example, catheter manufacturing industry and is not a suitable solution for other medical instruments that a physician may wish to employ, e.g. guidewires, stents, etc, during a medical procedure within an MRI system.

Compositions adapted to assist in visualizing medical devices in magnetic resonance imaging are well known. Reference may be had, e.g., to U.S. Pat. No. 6,361,759, the entire disclosure of which is hereby incorporated by reference into this specification. This patent describes and claims: "A coating for visualizing medical devices in magnetic resonance imaging, comprising a complex of formula (II): P-X-J-L-M$^{n+}$ (II), wherein P is a polymer, X is a surface functional group selected from the group consisting of an amino group and a carboxyl group, L is a chelate, M is a paramagnetic ion, n is an integer that is 2 or greater and J is the linker or spacer molecule and J is a lactam."

U.S. Pat. No. 4,731,239 discloses and claims: "A method for nuclear magnetic resonance (NMR) imaging of a patient comprising, prior to the NMR imaging of a patient, administering to said patient ferromagnetic, paramagnetic or diamagnetic particles effective to enhance an NMR image."

U.S. Pat. No. 4,989,608 discloses and claims: "A device which is specifically useful during magnetic resonance imaging of body tissue comprising: a flexible member of resinous material adapted to be inserted in the body tissue, the flexible member having ferromagnetic particles embedded therein at a concentration of about 0.001% to about 10% by weight of the material wherein, under magnetic resonance imaging, the flexible member exhibits characteristics which differ substantially from characteristics of the body tissue so that the visibility of the flexible member under magnetic resonance imaging is substantially enhanced, resulting in the flexible member being distinguishable from adjacent tissue as a dark area in brighter tissues and as a bright area in darker tissues, said member being free of elements which tend to degrade the overall quality of magnetic resonance images of the body tissue." At column 2 of this patent, it is disclosed that: "Ferromagnetic particles in general can cause magnetic field artifacts (MRI signal voids, with adjacent very bright signal bands, hereinafter called 'imaging artifacts' which are considerably larger than the size of the particle." The entire disclosure of this patent is hereby incorporated by reference into this specification.

U.S. Pat. No. 5,154,179 discloses and claims: "1. A catheter which is specifically useful during a magnetic resonance imaging of body tissue comprising: a contrast agent; a flexible tubular member having a first lumen with an additional lumen positioned therein, the additional lumen retaining the contrast agent therein; the flexible tubular member being made of resinous material and adapted to be inserted in the body tissue, the flexible tubular member having ferromagnetic particles embedded therein at a concentration of about 0.001% to about 10% by weight of the material wherein, under magnetic resonance imaging, the flexible member exhibits characteristics which differ substantially from characteristics of the body tissue so that the visibility of the flexible member under magnetic resonance is substantially enhanced, resulting in the flexible member being distinguishable from adjacent tissue as a dark area in brighter tissues and as a bright area in darker tissues, said member being free of elements which tend to degrade the overall quality of magnetic images of the body tissue." In the device of this patent, a ferromagnetic material was extruded into plastic as the plastic was being extruded to form the flexible tubular member. The entire disclosure of this United States patent is hereby incorporated by reference in to this specification.

U.S. Pat. No. 5,462,053 discloses and claims: "1. A contrast agent adapted for magnetic resonance imaging of a sample, said contrast agent comprising a suspension in a medium acceptable for magnetic resonance imaging of (a) coated particles of a contrast agent possessing paramagnetic characteristics and (b) coated particles of a contrast agent possessing diamagnetic characteristics, each of said coatings being selected from a group of materials which [I] renders said coated particles (a) and (b) substantially compatible with and substantially biologically and substantially chemically inert to each other and the environments to which said contrast agent is exposed during magnetic resonance imaging and [II] which substantially stabilizes said suspension; the nature of each of said coatings and the relative amounts of (a) and (b) in said suspension being such that the positive magnetic susceptibility of (a) substantially offsets the negative magnetic susceptibility of (b) and the resulting suspension has substantially zero magnetic susceptibility and, when employed in magnetic resonance imaging, results in the substantial elimination of imaging artifacts." The entire disclosure of this United States patent is hereby incorporated by reference into this specification. In column 1 of this patent, it is disclosed that: "It is well known to enhance NMR . . . images by . . . introducing into the sample to be imaged ferromagnetic, diamagnetic, or paramagnetic particles which shadow the image produced to intensity and contrast the image generated by the NMR sensitive nuclei. See, for example, the disclosures of U.S. Pat. Nos. 4,731,239; 4,863, 715; 4,749,560; 5,069,216; 5,055,288; 5,023,072; 4,951,674; 4,827,945; and 4,770,183 . . . ."

U.S. Pat. No. 5,744,958 discloses and claims: "A magnetic resonance imaging system, including: an imaging region and a means for generating a magnetic resonance image of a target object in the imaging region, said magnetic resonance image including an image of the target object, wherein the means for generating the magnetic resonance image includes means for producing an RF field having an RF frequency in the imaging region; and an instrument for use with the target object in the imaging region, said instrument including: an electrically non-conductive body, sized for use with the target object in the imaging region; and an electrically conductive, ultra-thin coating on at least part of the body, the coating being sufficiently thick to cause the instrument to be positively shown in the magnetic resonance image in response to presence of the instrument in the imaging region with the target object during generation of the magnetic resonance image, wherein the coating consists of material having a skin depth with respect to said RF frequency and the coating has a thickness less than the skin depth." At column 4 of this patent, it is disclosed that: "The present invention is based on the inventor's recognition that an electrically conductive, 'ultra-thin' coating (a coating whose thickness is less than or of the same order of magnitude as the coating's skin depth with respect to its electrical and magnetic properties and the frequency of the RF field in an MRI system) on an instrument can cause the instrument to create just enough artifact to be visible when imaged by an MRI system, but not so much artifact as to obscure or distort unacceptably the magnetic resonance imaging of a target (e.g., human tissue) also being imaged by the MRI system. In other words, the invention controls the artifact in such a way as to make the instrument visible but not appreciably distort the tissue structures being imaged by the MRI. An ultra-thin coating on an instrument embodying the invention typically has a thickness of on the order of hundreds or thousands of Angstroms." The entire disclosure of this United States patent is hereby incorporated by reference into this specification.

U.S. Pat. No. 6,203,777 describes and claims: "In a method of contrast enhanced nuclear magnetic resonance diagnostic imaging which comprises administering into the vascular system of a subject a contrast enhancing amount of a nuclear magnetic resonance imaging contrast agent and generating an image of said subject, the improvement comprising administering as said contrast agent composite particles comprising a biotolerable, biodegradable, non-immunogenic carbohydrate or carbohydrate derivative matrix material containing magnetically responsive particles, said magnetically responsive particles being of a material having a Curie temperature and said composite particles being no larger than one micrometer in size." The entire disclosure of this United States patent is hereby incorporated by reference into this specification.

United States published patent application 2002/0176822 discloses and claims: "A magnetic resonance imaging system, comprising: a magnetic resonance device for generating a magnetic resonance image of a target object in an imaging region; and an instrument for use with the target object in the imaging region, said instrument including a body sized for use in the target object and a polymeric-paramagnetic ion complex coating thereon in which said complex is represented by formula (I): P—X-L-M$^{n+}$ (I) wherein P is a polymer, X is a surface functional group, L is a chelate, M is a paramagnetic ion and n is an integer that is 2 or greater." The entire disclosure of this United States patent application is hereby incorporated by reference into this specification.

None of the prior art compositions or coatings appear to be adapted to both facilitate MRI imaging while simultaneously protecting biological tissue within a living organism from the adverse effects of the MRI electromagnetic wave. By way of illustration, some of the adverse effects include heating of tissue in contact with an implanted, conductive medical device, and voltages induced across tissue near or contiguous with leads of implanted medical devices.

It is an object of this invention to provide an assembly for protecting biological tissue from the adverse effects of heating during MRI scanning while simultaneously facilitating MRI imaging.

SUMMARY OF THE INVENTION

In accordance with this invention, there is provided an assembly for shielding an implanted medical device from the effects of high-frequency radiation and for emitting magnetic resonance signals during magnetic resonance imaging. The assembly includes an implanted medical device and a magnetic shield comprised of nanomagnetic material disposed between the medical device and the high-frequency radiation. In one embodiment, the magnetic resonance signals are detected by a remote receiver, which is thus able to locate the implanted medical device within a biological organism.

BRIEF DESCRIPTION OF THE DRAWINGS

The present invention will be more fully understood by reference to the following detailed thereof, when read in conjunction with the attached drawings, wherein like reference numerals refer to like elements, and wherein:

FIGS. 8A, 8B, 8C, and 8D are schematic sectional views of a substrate, such as one of the specific medical devices described in this application, coated with nanomagnetic particulate matter on its exterior surface;

FIGS. 13A, 13B, and 13C are schematic views of an implantable catheter coated with nanomagnetic particulate material;

FIGS. 14A through 14G are schematic views of an implantable, steerable catheter coated with nanomagnetic particulate material;

FIGS. 56A, 56B, and 56C are schematic illustrations of one preferred process of the invention.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

Figure 1:
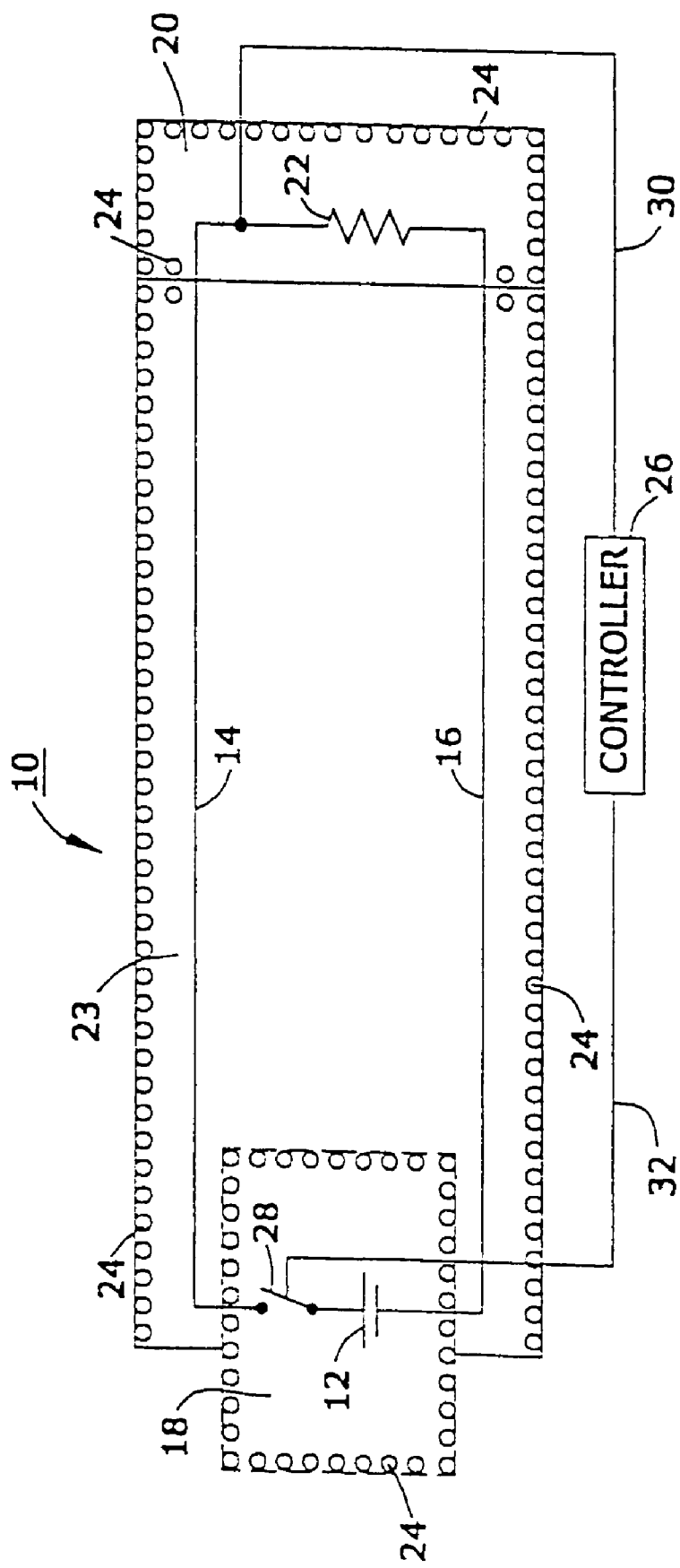
FIG. 1 is a schematic sectional view of a shielded implanted device comprised of one preferred conductor assembly of the invention.

FIG. 1 is a schematic sectional view of one preferred device 10 that is implanted in a living biological organism (not shown). Device 10 is comprised of a power source 12, a first conductor 14, a second conductor 16, a first insulative shield 18 disposed about power source 12, a second insulative shield 20 disposed about a load 22, a third insulative shield 23 disposed about a first conductor 14, and a second conductor 16, and a multiplicity of nanomagnetic particles 24 disposed on said first insulative shield 18 said second insulative shield 20, and said third insulative shield 23.

In one embodiment, the device 10 is a an implantable device used to monitor and maintain at least one physiologic function that is capable of operating in the presence of damaging electromagnetic interference; see, e.g., United States published patent application U.S. 2002/0038135, the entire disclosure of which is hereby incorporated by reference into this specification.

In one aspect of this embodiment, the device 10 is an implantable pacemaker. These pacemakers are well known to those skilled in the art. Reference may be had, e.g., to U.S. Pat. Nos. 5,697,959; 5,697,956 (implantable stimulation device having means for optimizing current drain); U.S. Pat. No. 5,456,692 (method for non-invasively altering the function of an implanted pacemaker); U.S. Pat. No. 5,431,691 (system for recording and displaying a sequential series of pacing events), U.S. Pat. No. 5,984,005 (multi-event bin heart rate histogram for use with an implantable pacemaker); U.S. Pat. Nos. 5,176,138; 5,003,975; 6,324,427; 5,788,717; 5,417,718; 5,228,438; and the like. The entire disclosure of each of these United States patents is hereby incorporated by reference into this specification.

In the embodiment depicted in FIG. 1, the power source 12 is a battery 12 that is operatively connected to a controller 26. Controller 26 is operatively connected to the load 22 and the switch 28. Depending upon the information furnished to controller 26, it may deliver no current, direct current, and/or current pulses to the load 22.

In one embodiment, not shown, some or all of the controller 26 and/or the wires 30 and 32 are shielded from magnetic radiation. In another embodiment, not shown, one or more connections between the controller 26 and the switch 28 and/or the load 22 are made by wireless means such as, e.g., telemetry means.

In one embodiment, the power source 12 provides a source of alternating current. In another embodiment, the power source 12 in conjunction with the controller 26 provides pulsed direct current.

The load 22 may, e.g., be any of the implanted devices known to those skilled in the art. Thus, e.g., as described hereinabove, the load 22 may be a pacemaker. Thus, e.g., load 22 may be an artificial heart. Thus, e.g., load 22 may be a heart-massaging device. Thus, e.g., load 22 may be a defibrillator.

The conductors 14 and 16 may comprise conductive material(s) that have a resistivity at 20 degrees Centigrade of from about 1 to about 100 microohm-centimeters. Thus, e.g., the conductive material(s) may be silver, copper, aluminum, alloys thereof, mixtures thereof, etc.

In one embodiment, the conductors 14 and 16 consist essentially of such conductive material. Thus, e.g., in one embodiment it is preferred not to use, e.g., copper wire coated with enamel.

Figure 1A:
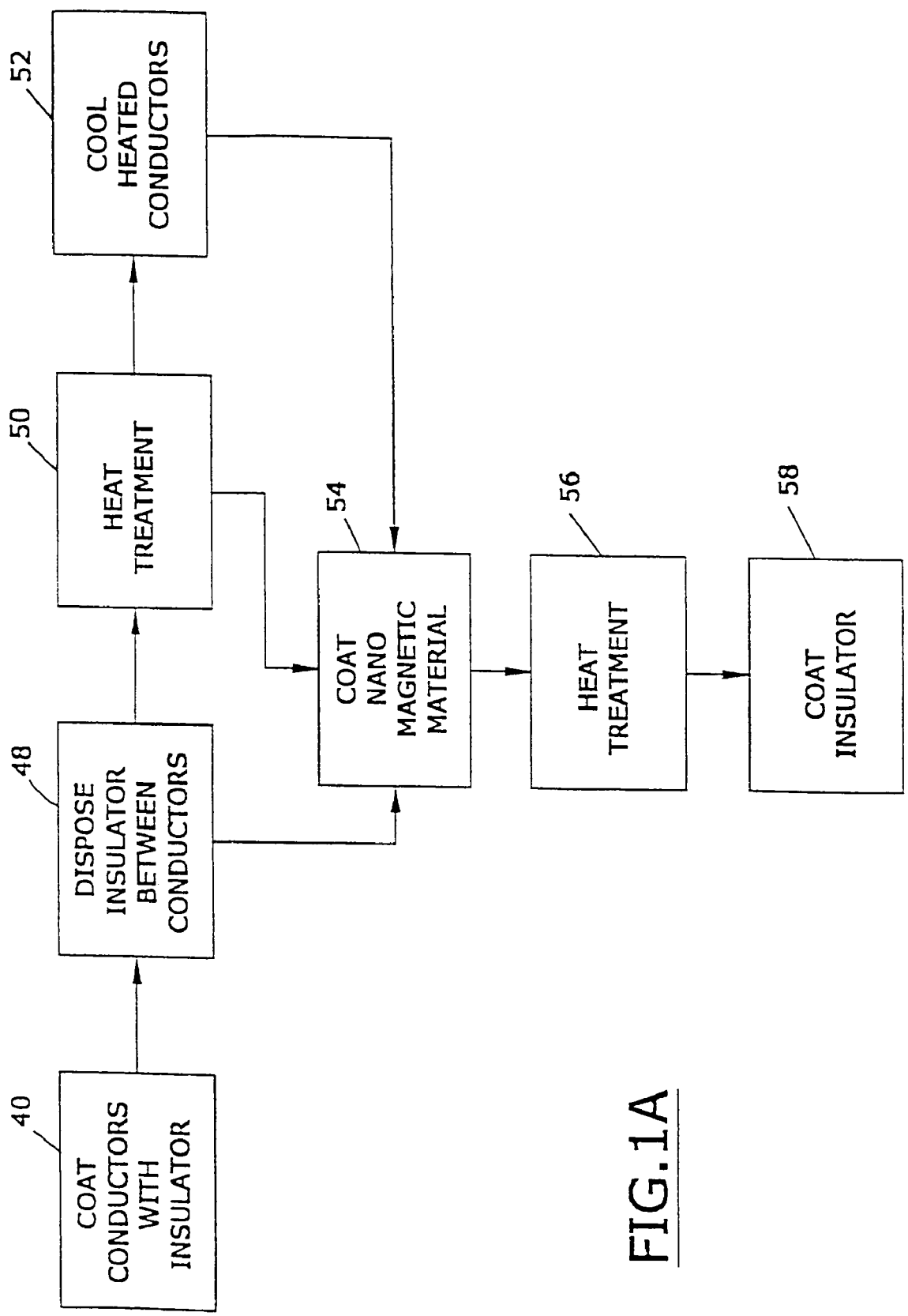
FIG. 1A is a flow diagram of a preferred process of the invention.

In the first step of one embodiment of the process of this invention, and referring to FIG. 1A and step 40, the conductive wires 14 and 16 (see FIG. 1) are coated with electrically insulative material. Suitable insulative materials include nano-sized silicon dioxide, aluminum oxide, cerium oxide, yttrium-stabilized zirconia, silicon carbide, silicon nitride, aluminum nitride, and the like. In general, these nano-sized particles will preferably have a particle size distribution such that at least about 90 weight percent of the particles have a maximum dimension in the range of from about 10 to about 100 nanometers.

The coated conductors 14 and 16 may be prepared by conventional means such as, e.g., the process described in U.S. Pat. No. 5,540,959, the entire disclosure of which is hereby incorporated by reference into this specification. This patent describes and claims a process for preparing a coated substrate, comprising the steps of: (a) creating mist particles from a liquid, wherein: said liquid is selected from the group consisting of a solution, a slurry, and mixtures thereof, said liquid is comprised of solvent and from 0.1 to 75 grams of solid material per liter of solvent, at least 95 volume percent of said mist particles have a maximum dimension less than 100 microns, and said mist particles are created from said first liquid at a rate of from 0.1 to 30 milliliters of liquid per minute; (b) contacting said mist particles with a carrier gas at a pressure of from 761 to 810 millimeters of mercury; (c) thereafter contacting said mist particles with alternating current radio frequency energy with a frequency of at least 1 megahertz and a power of at least 3 kilowatts while heating said mist particles to a temperature of at least about 100 degrees centigrade, thereby producing a heated vapor; (d) depositing said heated vapor onto a substrate, thereby producing a coated substrate; and (e) subjecting said coated substrate to a temperature of from about 450 to about 1,400 degrees centigrade for at least about 10 minutes.

By way of further illustration, one may coat conductors 14 and 16 by means of the processes disclosed in a text by D. Satas entitled "Coatings Technology Handbook" (Marcel Dekker, Inc., New York, N.Y., 1991). As is disclosed in such text, one may use cathodic arc plasma deposition (see pages 229 et seq.), chemical vapor deposition (see pages 257 et seq.), sol-gel coatings (see pages 655 et seq.), and the like. One may also use one or more of the processes disclosed in this book for preparing other coated members such as, e.g., sheath 4034 (see FIGS. 35 and 36).

Figure 2:
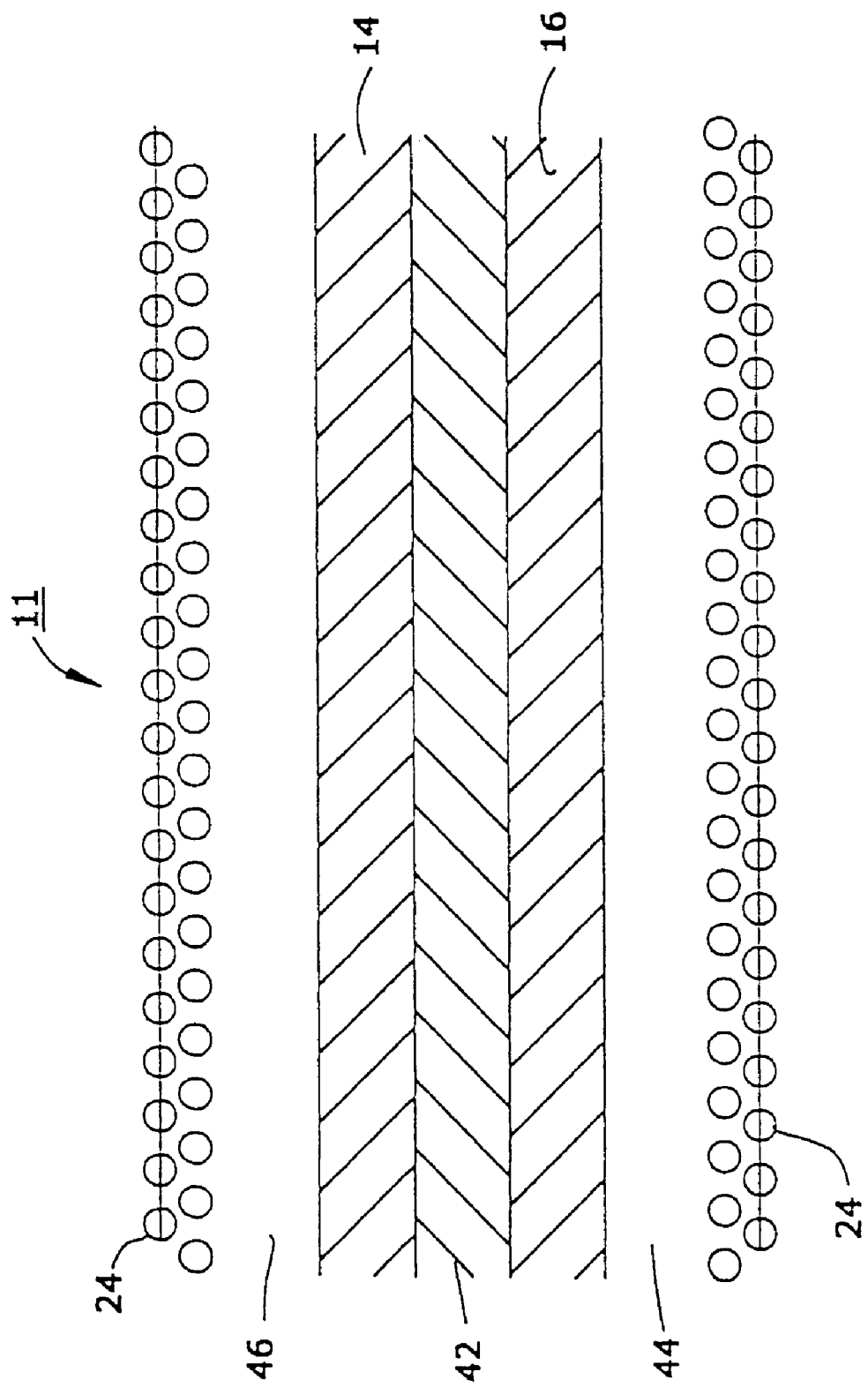
FIG. 2 is an enlarged sectional view of a portion of the conductor assembly of FIG. 1.

FIG. 2 is a sectional view of the coated conductors 14/16 of the device of FIG. 1. Referring to FIG. 2, and in the preferred embodiment depicted therein, it will be seen that conductors 14 and 16 are separated by insulating material 42. In order to obtain the structure depicted in FIG. 2, one may simultaneously coat conductors 14 and 16 with the insulating material so that such insulators both coat the conductors 14 and 16 and fill in the distance between them with insulation.

Referring again to FIG. 2, the insulating material 42 that is disposed between conductors 14/16 may be the same as the insulating material 44/46 that is disposed above conductor 14 and below conductor 16. Alternatively, and as dictated by the choice of processing steps and materials, the insulating material 42 may be different from the insulating material 44 and/or the insulating material 46. Thus, step 48 (see FIG. 1A) of the process describes disposing insulating material between the coated conductors 14 and 16. This step may be done simultaneously with step 40 (see FIG. 1A); and it may be done thereafter.

The insulating material 42, the insulating material 44, and the insulating material 46 each generally has a resistivity of from about $1 \times 10^9$ to about $1 \times 10^{13}$ ohm-centimeters.

Referring again to FIG. 1A, after the insulating material 42/44/46 (see FIG. 2) has been deposited, and in one embodiment, the coated conductor assembly is preferably heat treated in step 50. This heat treatment often is used in conjunction with coating processes in which the heat is required to bond the insulative material to the conductors 14/16 (see FIG. 2).

The heat-treatment step may be conducted after the deposition of the insulating material 42/44/46, or it may be conducted simultaneously therewith. In either event, and when it is used, it is preferred to heat the coated conductors 14/16 (see FIG. 2) to a temperature of from about 200 to about 600 degrees Centigrade for from about 1 minute to about 10 minutes.

Referring again to FIG. 1A, and in step 52 of the process, after the coated conductors 14/16 (see FIG. 2) have been subjected to heat treatment step 50, they are allowed to cool to a temperature of from about 30 to about 100 degrees Centigrade over a period of time of from about 3 to about 15 minutes.

One need not invariably heat treat and/or cool. Thus, referring to FIG. 1A, one may immediately coat nanomagnetic particles onto to the coated conductors 14/16 in step 54 either after step 48 and/or after step 50 and/or after step 52.

Referring again to FIG. 1A, in step 54, nanomagnetic materials are coated onto the previously coated conductors 14 and 16. This is best shown in FIG. 2, wherein the nanomagnetic particles are identified as particles 24.

In general, and as is known to those skilled in the art, nanomagnetic material is magnetic material which has an average particle size less than 100 nanometers and, preferably, in the range of from about 2 to 50 nanometers. Reference may be had, e.g., to U.S. Pat. No. 5,889,091 (rotationally free nanomagnetic material), U.S. Pat. Nos. 5,714,136; 5,667,924; and the like. The entire disclosure of each of these United States patents is hereby incorporated by reference, into this specification.

The nanomagnetic materials may be, e.g., nano-sized ferrites such as, e.g., the nanomagnetic ferrites disclosed in U.S. Pat. No. 5,213,851, the entire disclosure of which is hereby incorporated by reference into this specification. This patent claims a process for coating a layer of ferritic material with a thickness of from about 0.1 to about 500 microns onto a substrate at a deposition rate of from about 0.01 to about 10 microns per minute per 35 square centimeters of substrate surface, comprising the steps of: (a) providing a solution comprised of a first compound and a second compound, wherein said first compound is an iron compound and said second compound is selected from the group consisting of compounds of nickel, zinc, magnesium, strontium, barium, manganese, lithium, lanthanum, yttrium, scandium, samarium, europium, terbium, dysprosium, holmium, erbium, ytterbium, lutetium, cerium, praseodymium, thulium, neodymium, gadolinium, aluminum, iridium, lead, chromium, gallium, indium, samarium, cobalt, titanium, and mixtures thereof, and wherein said solution is comprised of from about 0.01 to about 1,000 grams of a mixture consisting essentially of said compounds per liter of said solution; (b) subjecting said solution to ultrasonic sound waves at a frequency in excess of 20,000 hertz, and to an atmospheric pressure of at least about 600 millimeters of mercury, thereby causing said solution to form into an aerosol; (c) providing a radio frequency plasma reactor comprised of a top section, a bottom section, and a radio-frequency coil; (d) generating a hot plasma gas within said radio frequency plasma reactor, thereby producing a plasma region; (e) providing a flame region disposed above said top section of said radio frequency plasma reactor; (f) contacting said aerosol with said hot plasma gas within said plasma reactor while subjecting said aerosol to an atmospheric pressure of at least about 600 millimeters of mercury and to a radio frequency alternating current at a frequency of from about 100 kilohertz to about 30 megahertz, thereby forming a vapor; (g) providing a substrate disposed above said flame region; and (h) contacting said vapor with said substrate, thereby forming said layer of ferritic material.

By way of further illustration, one may use the techniques described in an article by M. DeMarco, X. W. Wang, et al. on "Mossbauer and magnetization studies of nickel ferrites" published in the Journal of Applied Physics 73(10), May 15, 1993, at pages 6287-6289.

In general, the thickness of the layer of nanomagnetic material deposited onto the coated conductors 14/16 is less than about 5 microns and generally from about 0.1 to about 3 microns.

After the nanomagnetic material is coated in step 54 of FIG. 1A, the coated assembly may be optionally heat-treated in step 56. In this optional step 56, it is preferred to subject the coated conductors 14/16 to a temperature of from about 200 to about 600 degrees Centigrade for from about 1 to about 10 minutes.

Figure 3:
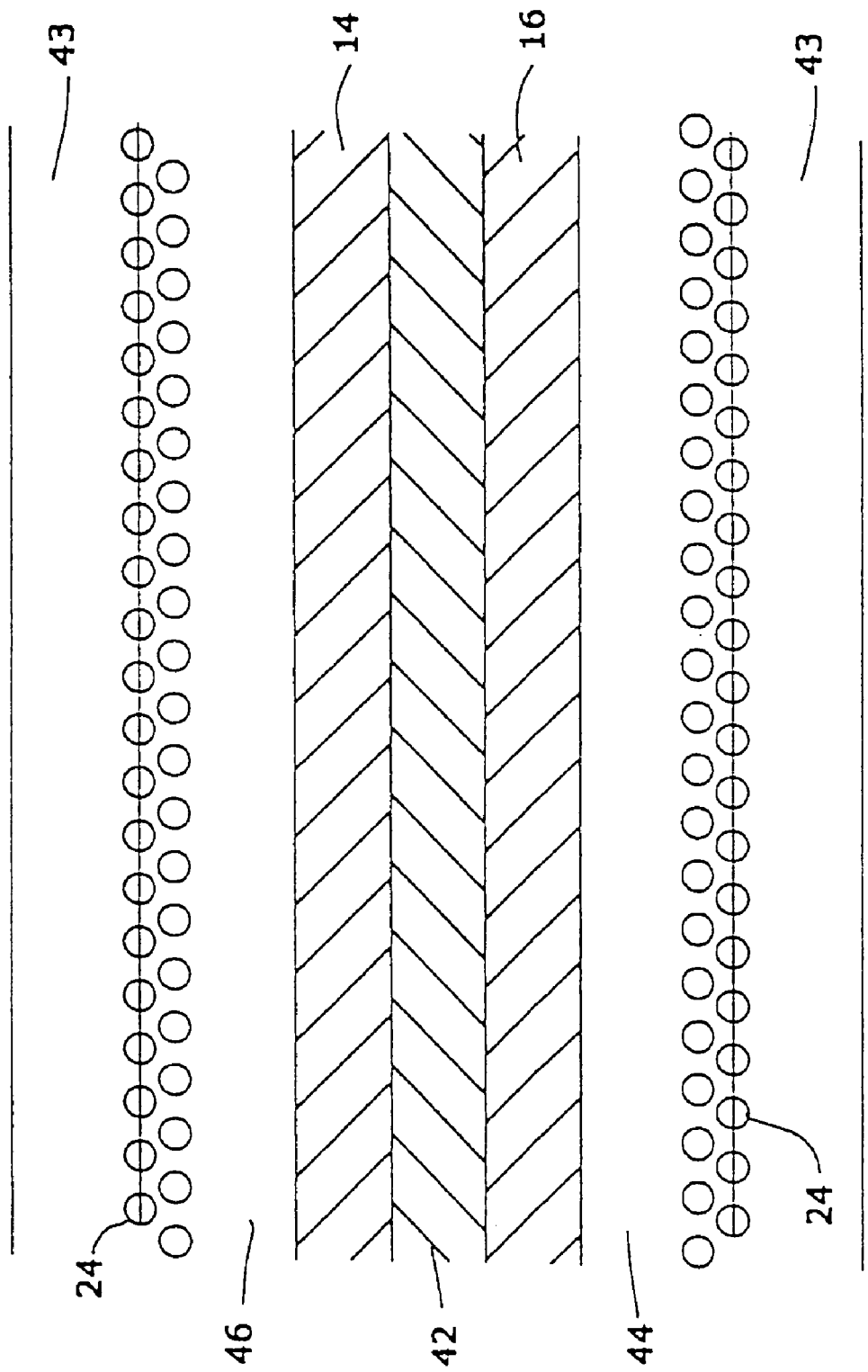
FIG. 3 is a sectional view of another conductor assembly of this invention.

In one embodiment, illustrated in FIG. 3, one or more additional insulating layers 43 are coated onto the assembly depicted in FIG. 2, by one or more of the processes disclosed hereinabove. This is conducted in optional step 58 (see FIG. 1A).

Figure 4:
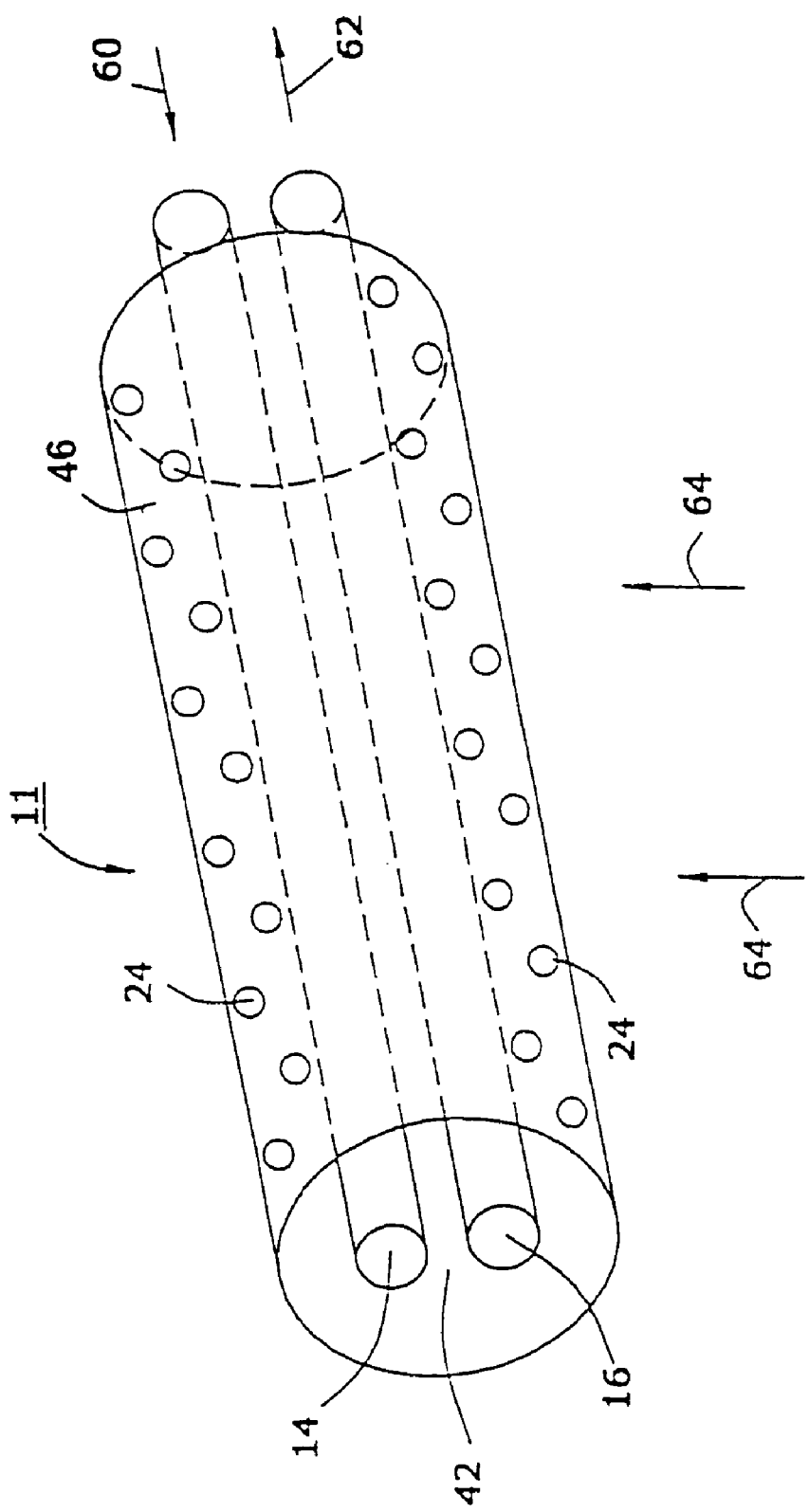
FIG. 4 is a schematic view of the conductor assembly of FIG. 2.

FIG. 4 is a partial schematic view of the assembly 11 of FIG. 2, illustrating the current flow in such assembly. Referring to FIG. 4, it will be seen that current flows into conductor 14 in the direction of arrow 60, and it flows out of conductor 16 in the direction of arrow 62. The net current flow through the assembly 11 is zero; and the net Lorentz force in the assembly 11 is thus zero when placed in an external magnetic field (not shown). Consequently, even high current flows in the assembly 11 do not cause such assembly to move.

In the embodiment depicted in FIG. 4, conductors 14 and 16 are substantially parallel to each other. As will be apparent, without such parallel orientation, there may be some net current and some net Lorentz effect.

In the embodiment depicted in FIG. 4, and in one preferred aspect thereof, the conductors 14 and 16 preferably have the same diameters and/or the same compositions and/or the same length.

Referring again to FIG. 4, the nanomagnetic particles 24 are present in a density sufficient so as to provide shielding from magnetic flux lines 64. Without wishing to be bound to any particular theory, applicant believes that the nanomagnetic particles 24 trap and pin the magnetic lines of flux 64.

In order to function optimally, the nanomagnetic particles 24 have a specified magnetization. As is known to those skilled in the art, magnetization is the magnetic moment per unit volume of a substance. Reference may be had, e.g., to U.S. Pat. Nos. 4,169,998; 4,168,481; 4,166,263; 5,260,132; 4,778,714; and the like. The entire disclosure of each of these United States patents is hereby incorporated by reference into this specification.

Referring again to FIG. 4, the layer of nanomagnetic particles 24 preferably has a saturation magnetization, at 25 degrees Centigrade, of from about 1 to about 36,000 Gauss, or higher. In one embodiment, the saturation magnetization at room temperature of the nanomagnetic particles is from about 500 to about 10,000 Gauss. For a discussion of the saturation magnetization of various materials, reference may be had, e.g., to U.S. Pat. Nos. 4,705,613; 4,631,613; 5,543,070; 3,901,741 (cobalt, samarium, and gadolinium alloys), and the like. The entire disclosure of each of these United States patents is hereby incorporated by reference into this specification. As will be apparent to those skilled in the art, especially upon studying the aforementioned patents, the saturation magnetization of thin films is often higher than the saturation magnetization of bulk objects.

In one embodiment, it is preferred to utilize a thin film with a thickness of less than about 2 microns and a saturation magnetization in excess of 20,000 Gauss. The thickness of the layer of nanomagnetic material is measured from the bottom surface of the layer that contains such material to the top surface of such layer that contains such material; and such bottom surface and/or such top surface may be contiguous with other layers of material (such as insulating material) that do not contain nanomagnetic particles.

Thus, e.g., one may make a thin film in accordance with the procedure described at page 156 of Nature, Volume 407, Sep. 14, 2000, that describes a multilayer thin film that has a saturation magnetization of 24,000 Gauss.

By the appropriate selection of nanomagnetic particles, and the thickness of the films deposited, one may obtain saturation magnetizations of as high as at least about 36,000 Gauss.

In the preferred embodiment depicted in FIG. 4, the nanomagnetic particles 24 are disposed within an insulating matrix so that any heat produced by such particles will be slowly dispersed within such matrix. Such matrix, as indicated hereinabove, may be made from ceria, calcium oxide, silica, alumina, and the like. In general, the insulating material 42 preferably has a thermal conductivity of less than about 20 (calories-centimeters/square centimeters–degree second)×10,000. See, e.g., page E-6 of the $63^{rd}$ Edition of the "Handbook of Chemistry and Physics" (CRC Press, Inc., Boca Raton, Fla., 1982).

The nanomagnetic materials 24 typically comprise one or more of iron, cobalt, nickel, gadolinium, and samarium atoms. Thus, e.g., typical nanomagnetic materials include alloys of iron and nickel (permalloy), cobalt, niobium, and zirconium (CNZ), iron, boron, and nitrogen, cobalt, iron, boron, and silica, iron, cobalt, boron, and fluoride, and the like. These and other materials are descried in a book by J. Douglas Adam et al. entitled "Handbook of Thin Film Devices" (Academic Press, San Diego, Calif., 2000). Chapter 5 of this book beginning at page 185, describes "magnetic films for planar inductive components and devices;" and Tables 5.1 and 5.2 in this chapter describe many magnetic materials.

Figure 5:
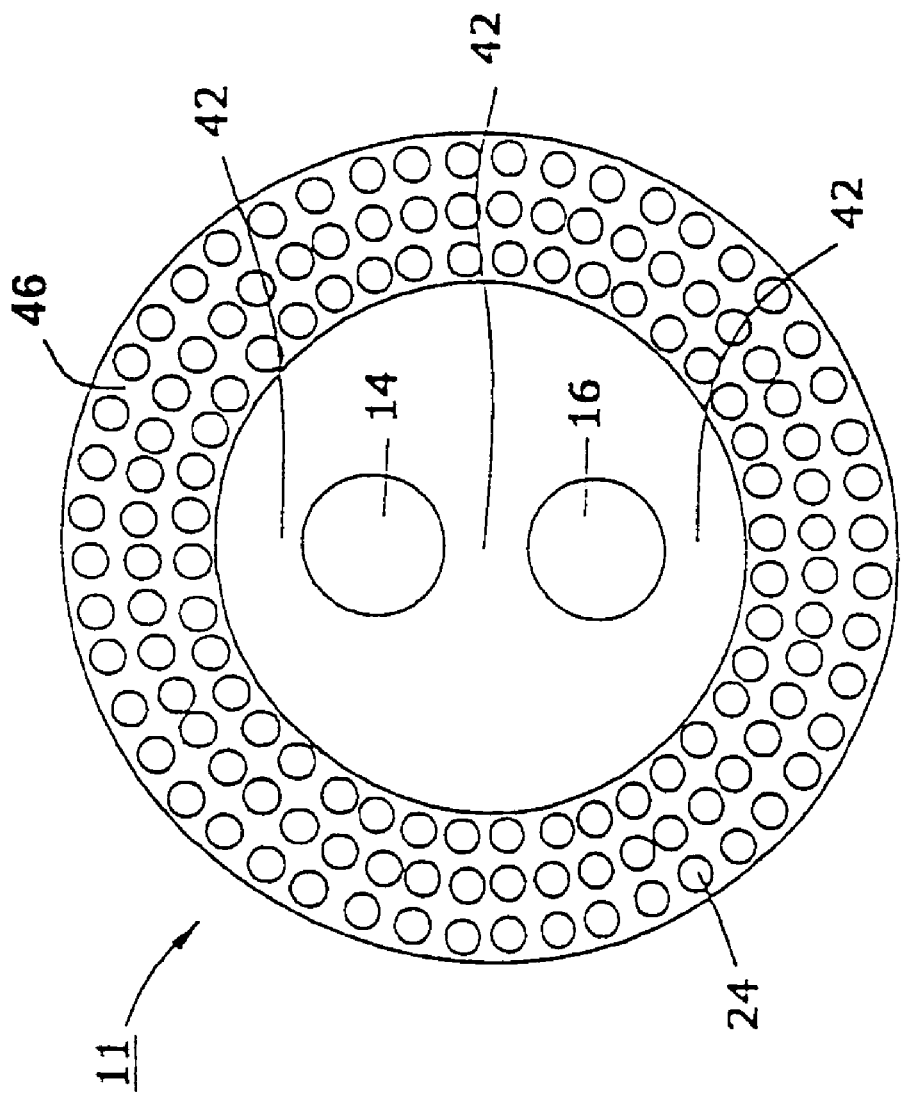
FIG. 5 is a sectional view of the conductor assembly of FIG. 2.

FIG. 5 is a sectional view of the assembly 11 of FIG. 2. The device of FIG. 5, and of the other Figures of this application, is preferably substantially flexible. As used in this specification, the term flexible refers to an assembly that can be bent to form a circle with a radius of less than 2 centimeters without breaking. Put another way, the bend radius of the coated assembly 11 can be less than 2 centimeters. Reference may be had, e.g., to U.S. Pat. Nos. 4,705,353; 5,946,439; 5,315,365; 4,641,917; 5,913,005; and the like. The entire disclosure of each of these United States patents is hereby incorporated by reference into this specification.

In another embodiment, not shown, the shield is not flexible. Thus, in one aspect of this embodiment, the shield is a rigid, removable sheath that can be placed over an endoscope or a biopsy probe used inter-operatively with magnetic resonance imaging.

In another embodiment of the invention, there is provided a magnetically shielded conductor assembly comprised of a conductor and a film of nanomagnetic material disposed above said conductor. In this embodiment, the conductor has a resistivity at 20 degrees Centigrade of from about 1 to about 2,000 microohm-centimeters and is comprised of a first surface exposed to electromagnetic radiation. In this embodiment, the film of nanomagnetic material has a thickness of from about 100 nanometers to about 10 micrometers and a mass density of at least about 1 gram per cubic centimeter, wherein the film of nanomagnetic material is disposed above at least about 50 percent of said first surface exposed to electromagnetic radiation, and the film of nanomagnetic material has a saturation magnetization of from about 1 to about 36,000 Gauss, a coercive force of from about 0.01 to about 5,000 Oersteds, a relative magnetic permeability of from about 1 to about 500,000, and a magnetic shielding factor of at least about 0.5. In this embodiment, the nanomagnetic material has an average particle size of less than about 100 nanometers.

Figure 6:
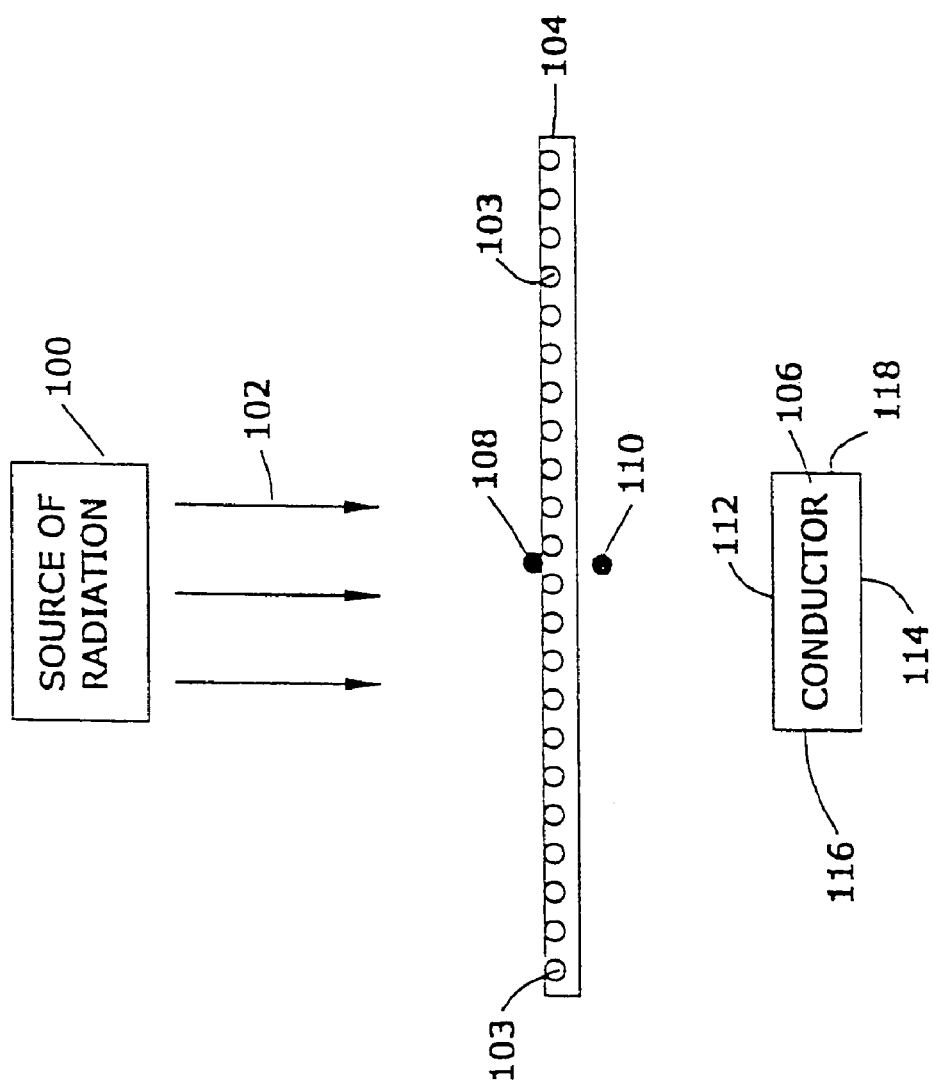
FIG. 6 is a schematic of another preferred shielded conductor assembly.

In one preferred embodiment of this invention, a film of nanomagnetic particles is disposed above at least one surface of a conductor. Referring to FIG. 6, and in the schematic diagram depicted therein, a source of electromagnetic radiation 100 emits radiation 102 in the direction of film 104. Film 104 is disposed above conductor 106, i.e., it is disposed between conductor 106 and the electromagnetic radiation 102.

The film 104 is adapted to reduce the magnetic field strength at point 110 relative to the field strength at point 108 (which is disposed less than 1 centimeter above film 104) by at least about 50 percent. Thus, if one were to measure the magnetic field strength at point 108, and thereafter measure the magnetic field strength at point 110 (which is disposed less than 1 centimeter below film 104), the latter magnetic field strength would be no more than about 50 percent of the former magnetic field strength. Put another way, the film 104 has a magnetic shielding factor of at least about 0.5.

In one embodiment, the film 104 has a magnetic shielding factor of at least about 0.9, i.e., the magnetic field strength at point 110 is no greater than about 10 percent of the magnetic field strength at point 108. Thus, e.g., the static magnetic field strength at point 108 can be, e.g., one Tesla, whereas the static magnetic field strength at point 110 can be, e.g., 0.1 Tesla. Furthermore, the time-varying magnetic field strength of 100 milliTesla would be reduced to about 10 milliTesla of the time-varying field.

Referring again to FIG. 6, the nanomagnetic material 103 in film 104 has a saturation magnetization of form about 1 to about 36,000 Gauss. This property has been discussed elsewhere in this specification. In one embodiment, the nanomagnetic material 103 has a saturation magnetization of from about 200 to about 26,000 Gauss.

The nanomagnetic material 103 in film 104 also has a coercive force of from about 0.01 to about 5,000 Oersteds. The term coercive force refers to the magnetic field, H, which must be applied to a magnetic material in a symmetrical, cyclically magnetized fashion, to make the magnetic induction, B, vanish; this term often is referred to as magnetic coercive force. Reference may be had, e.g., to U.S. Pat. Nos. 4,061,824; 6,257,512; 5,967,223; 4,939,610; 4,741,953; and the like. The entire disclosure of each of these United States patents is hereby incorporated by reference into this specification.

In one embodiment, the nanomagnetic material 103 has a coercive force of from about 0.01 to about 3,000 Oersteds. In yet another embodiment, the nanomagnetic material 103 has a coercive force of from about 0.1 to about 10 Oersted.

Referring again to FIG. 6, the nanomagnetic material 103 in film 104 preferably has a relative magnetic permeability of from about 1 to about 500,000; in one embodiment, such material 103 has a relative magnetic permeability of from about 1.5 to about 260,000. As used in this specification, the term relative magnetic permeability is equal to B/H, and is also equal to the slope of a section of the magnetization curve of the film. Reference may be had, e.g., to page 4-28 of E. U. Condon et al.'s "Handbook of Physics" (McGraw-Hill Book Company, Inc., New York, 1958).

Reference also may be had to page 1399 of Sybil P. Parker's "McGraw-Hill Dictionary of Scientific and Technical Terms," Fourth Edition (McGraw Hill Book Company, New York, 1989). As is disclosed on page 1399, permeability is " . . . a factor, characteristic of a material, that is proportional to the magnetic induction produced in a material divided by the magnetic field strength; it is a tensor when these quantities are not parallel . . . ." Relative permeability is the permeability of the material divided by the permeability of free space.

Reference also may be had, e.g., to U.S. Pat. Nos. 6,181,232; 5,581,224; 5,506,559; 4,246,586; 6,390,443; and the like. The entire disclosure of each of these United States patents is hereby incorporated by reference into this specification.

In one embodiment, the nanomagnetic material 103 in film 104 has a relative magnetic permeability of from about 1.5 to about 2,000.

Referring again to FIG. 6, the nanomagnetic material 103 in film 104 preferably has a mass density of at least about 0.001 grams per cubic centimeter; in one embodiment, such mass density is at least about 1 gram per cubic centimeter. As used in this specification, the term mass density refers to the mass of a give substance per unit volume. See, e.g., page 510 of the aforementioned "McGraw-Hill Dictionary of Scientific and Technical Terms." In one embodiment, the film 104 has a mass density of at least about 3 grams per cubic centimeter. In another embodiment, the nanomagnetic material 103 has a mass density of at least about 4 grams per cubic centimeter.

In the embodiment depicted in FIG. 6, the film 104 is disposed above 100 percent of the surfaces 112, 114, 116, and 118 of the conductor 106. In the embodiment depicted in FIG. 2, by comparison, the nanomagnetic film is disposed around the conductor.

Figure 7:
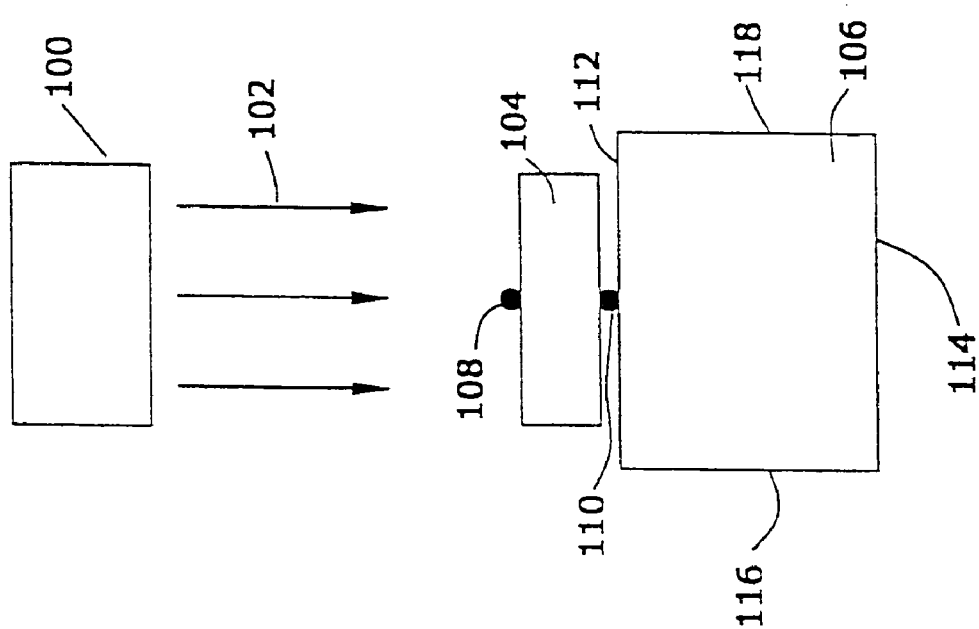
FIG. 7 is a schematic of yet another configuration of a shielded conductor assembly.

Yet another embodiment is depicted in FIG. 7. In the embodiment depicted in FIG. 7, the film 104 is not disposed in front of either surface 114, or 116, or 118 of the conductor 106. Inasmuch as radiation is not directed towards these surfaces, this is possible.

What is essential in this embodiment, however, is that the film 104 be interposed between the radiation 102 and surface 112. It is preferred that film 104 be disposed above at least about 50 percent of surface 112. In one embodiment, film 104 is disposed above at least about 90 percent of surface 112.

Many implanted medical devices have been developed to help medical practitioners treat a variety of medical conditions by introducing an implantable medical device, partly or completely, temporarily or permanently, into the esophagus, trachea, colon, biliary tract, urinary tract, vascular system or other location within a human or veterinary patient. For example, many treatments of the vascular system entail the introduction of a device such as a guidewire, catheter, stent, arteriovenous shunt, angioplasty balloon, a cannula or the like. Other examples of implantable medical devices include, e.g., endoscopes, biopsy probes, wound drains, laparoscopic equipment, urethral inserts, and implants. Most such implantable medical devices are made in whole or in part of metal, and are not part of an electrical circuit.

When a patient with one of these implanted devices is subjected to high intensity magnetic fields, such as during magnetic resonance imaging (MRI), electrical currents are induced in the metallic portions of the implanted devices. The electrical currents so induced often create substantial amounts of heat. The heat can cause extensive damage to the tissue surrounding the implantable medical device.

Furthermore, when a patient with one of these implanted devices undergoes magnetic resonance imaging (MRI), signal loss and disruption of the diagnostic image often occur as a result of the presence of a metallic object, which causes a disruption of the local magnetic field. This disruption of the local magnetic field alters the relationship between position and frequency, which are crucial for proper image reconstruction. Therefore, patients with implantable medical devices are generally advised not to undergo MRI procedures. In many cases, the presence of such a device is a strict contraindication for MRI (See Shellock, F. G., Magnetic Resonance Procedures: Health Effects and Safety, 2001 Edition, CRC Press, Boca Raton, Fla.; also see Food and Drug Administration, Magnetic Resonance Diagnostic Device: Panel Recommendation and Report on Petitions for MR Reclassification, Federal register, 1988, 53, 7575-7579). Any contraindication such as this, whether a strict or relative contraindication, is a serious problem since it deprives the patient from undergoing an MRI examination, or even using MRI to guide other therapies, such as proper placement of diagnostic and/or therapeutics devices including angioplasty balloons, radio frequency ablation catheters for treatment of cardiac arrythmias, sensors to assess the status of pharmacological treatment of tumors, or verification of proper placement of other permanently implanted medical devices. The rapidly growing capabilities and use of MRI in these and other areas prevent an increasingly large group of patients from benefiting from this powerful diagnostic and intra-operative tool.

The use of implantable medical devices is well known in the prior art. Thus, e.g., U.S. Pat. No. 4,180,600 discloses and claims an implantable medical device comprising a shielded conductor wire consisting of a conductive copper core and a magnetically soft alloy metallic sheath metallurgically secured to the conductive core, wherein the sheath consists essentially of from 2 to 5 weight percent of molybdenum, from about 15 to about 23 weight percent of iron, and from about 75 to about 85 weight percent of nickel. Although the device of this patent does provide magnetic shielding, it still creates heat when it interacts with strong magnetic fields, and it can still disrupt and distort magnetic resonance images.

U.S. Pat. No. 5,817,017 discloses and claims an implantable medical device having enhanced magnetic image visibility. The magnetic images are produced by known magnetic imaging techniques, such as MRI. The invention disclosed in the '017 patent is useful for modifying conventional catheters, stents, guidewires and other implantable devices, as well as interventional devices, such as for suturing, biopsy, which devices may be temporarily inserted into the body lumen or tissue; and it is also useful for permanently implantable devices. The entire disclosure of this United States patent is hereby incorporated by reference into this specification.

In the process disclosed in the '017 patent, paramagnetic ionic particles are fixedly incorporated and dispersed in selective portions of an implantable medical device such as, e.g., a catheter. When the catheter coated with paramagnetic ionic particles is inserted into a patient undergoing magnetic resonance imaging, the image signal produced by the catheter is of higher intensity. However, paramagnetic implants, although less susceptible to magnetization than ferromagnetic implants, can produce image artifacts in the presence of a strong magnetic field, such as that of a magnetic resonant imaging coil, due to eddy currents generated in the implants by time-varying electromagnetic fields that, in turn, disrupt the local magnetic field and disrupt the image.

Any electrically conductive material, even a non-metallic material (and even one not in an electrical circuit) will develop eddy currents and thus produce electrical potential and thermal heating in the presence of a time-varying electromagnetic field or a radio frequency field.

Thus, there is a need to provide an implantable medical device, which is shielded from strong electromagnetic fields, which does not create large amounts of heat in the presence of such fields, and which does not produce image artifacts when subjected to such fields. It is one object of the present invention to provide such a device, including a shielding device that can be reversibly attached to an implantable medical device.

FIGS. 8A, 8B, 8C, and 8D are schematic sectional views of a substrate 201, which is preferably a part of an implantable medical device.

Referring to FIG. 8A, it will be seen that substrate 201 is coated with nanomagnetic particles 202 on the exterior surface 203 of the substrate.

Referring to FIG. 8B, and in the embodiment depicted therein, the substrate 201 is coated with nanomagnetic particulate 202 on both the exterior surface 203 and the interior surface 204.

Figure 8C:
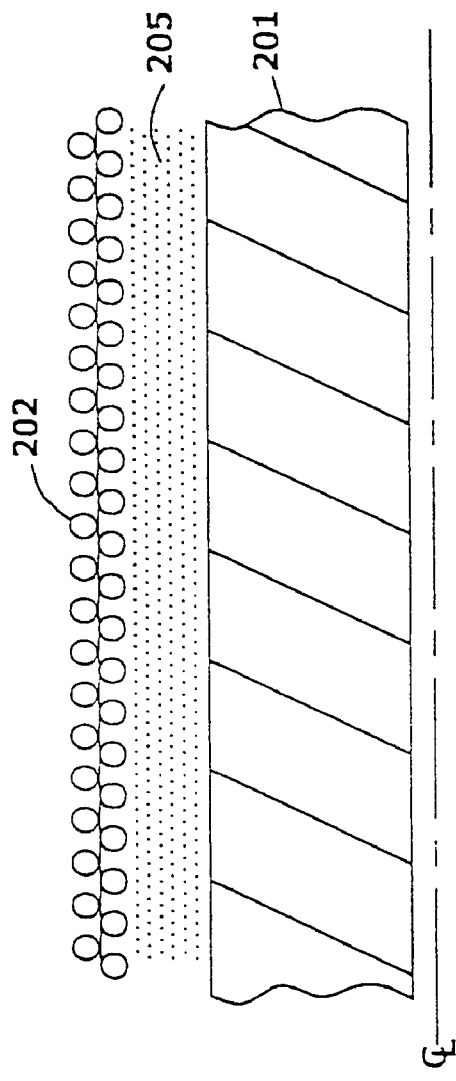

Referring to FIG. 8C, and in the preferred embodiment depicted therein, a layer of insulating material 205 separates substrate 201 and the layer of nanomagnetic coating 202.

Figure 8D:
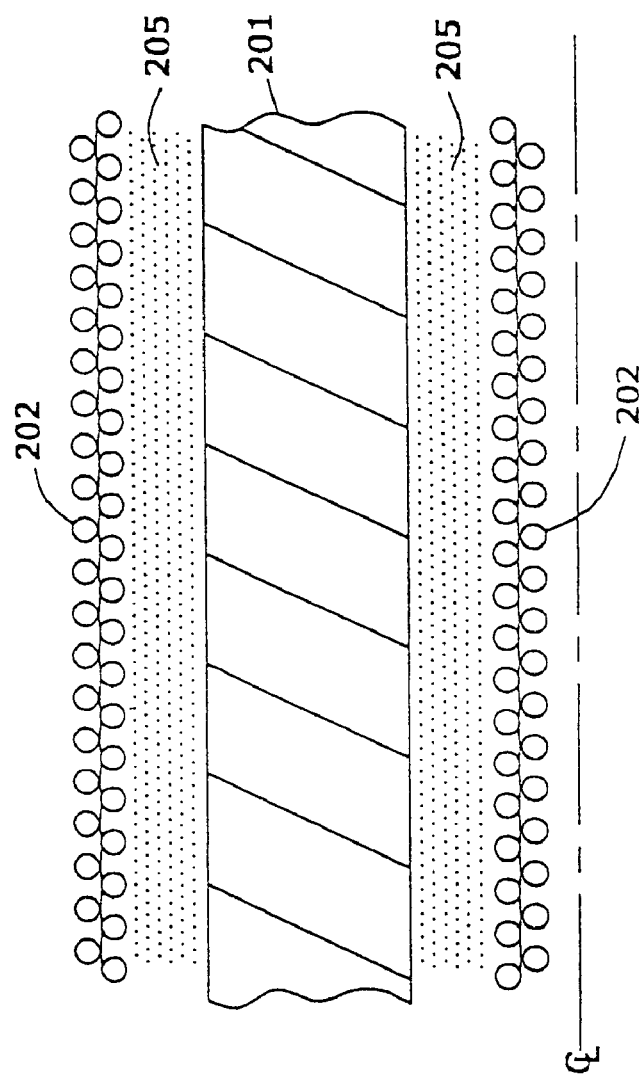

Referring to FIG. 8D, it will be seen that one or more layers of insulating material 205 separate the inside and outside surfaces of substrate 201 from respective layers of nanomagnetic coating 202.

Figure 9:
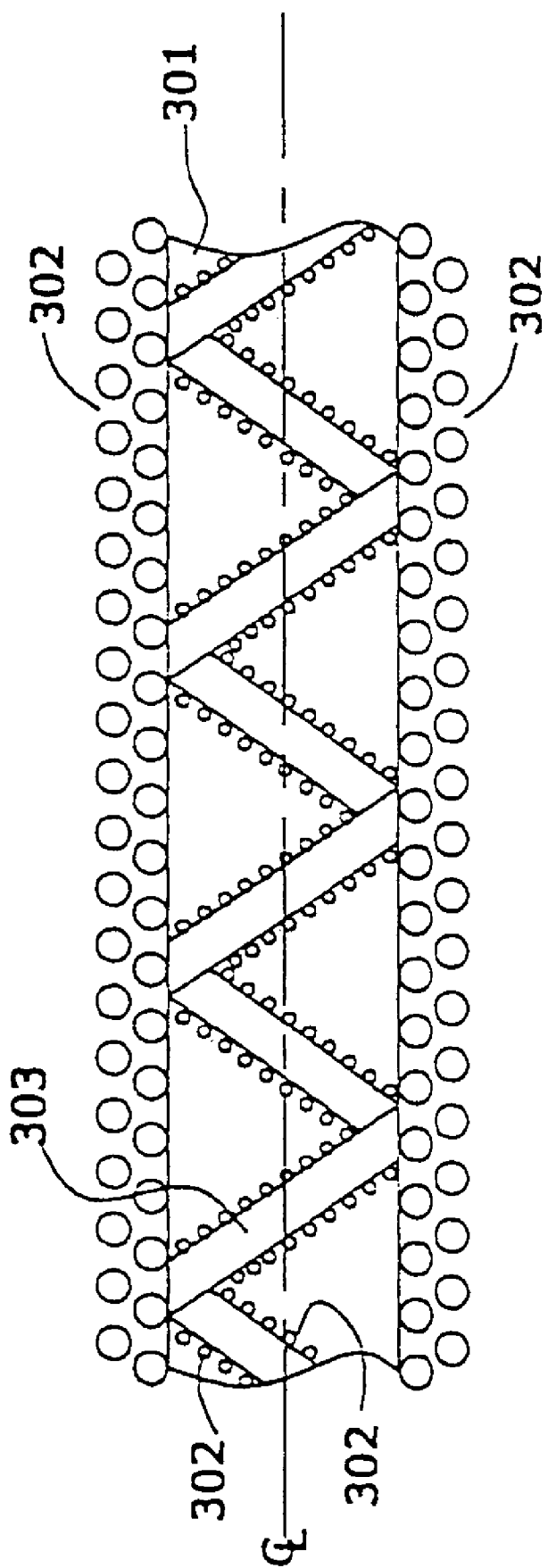
FIG. 9 is a schematic sectional view of an elongated cylinder, similar to the specific medical devices described in this application, coated with nanomagnetic particulate (the cylinder encloses a flexible, expandable helical member, which is also coated with nanomagnetic particulate material)

FIG. 9 is a schematic sectional view of a substrate 301 which is part of an implantable medical device (not shown). Referring to FIG. 9, and in the embodiment depicted therein, it will be seen that substrate 301 is coated with nanomagnetic material 302, which may differ from nanomagnetic material 202 (see FIG. 8A).

In one embodiment, the substrate 301 is in the shape of a cylinder, such as an enclosure for a medical catheter, stent, guidewire, and the like. In one aspect of this embodiment, the cylindrical substrate 301 encloses a helical member 303, which is also coated with nanomagnetic particulate material 302.

In another embodiment (not shown), the cylindrical substrate 301 depicted in FIG. 9 is coated with multiple layers of nanomagnetic materials. In one aspect of this embodiment, the multiple layers of nanomagnetic particulate are insulated from each other. In another aspect of this embodiment, each of such multiple layers is comprised of nanomagnetic particles of different sizes and/or densities and/or chemical densities. In one aspect of this embodiment, not shown, each of such multiple layers may have different thickness. In another aspect of this embodiment, the frequency response and degree of shielding of each such layer differ from that of one or more of the other such layers.

Figure 10:
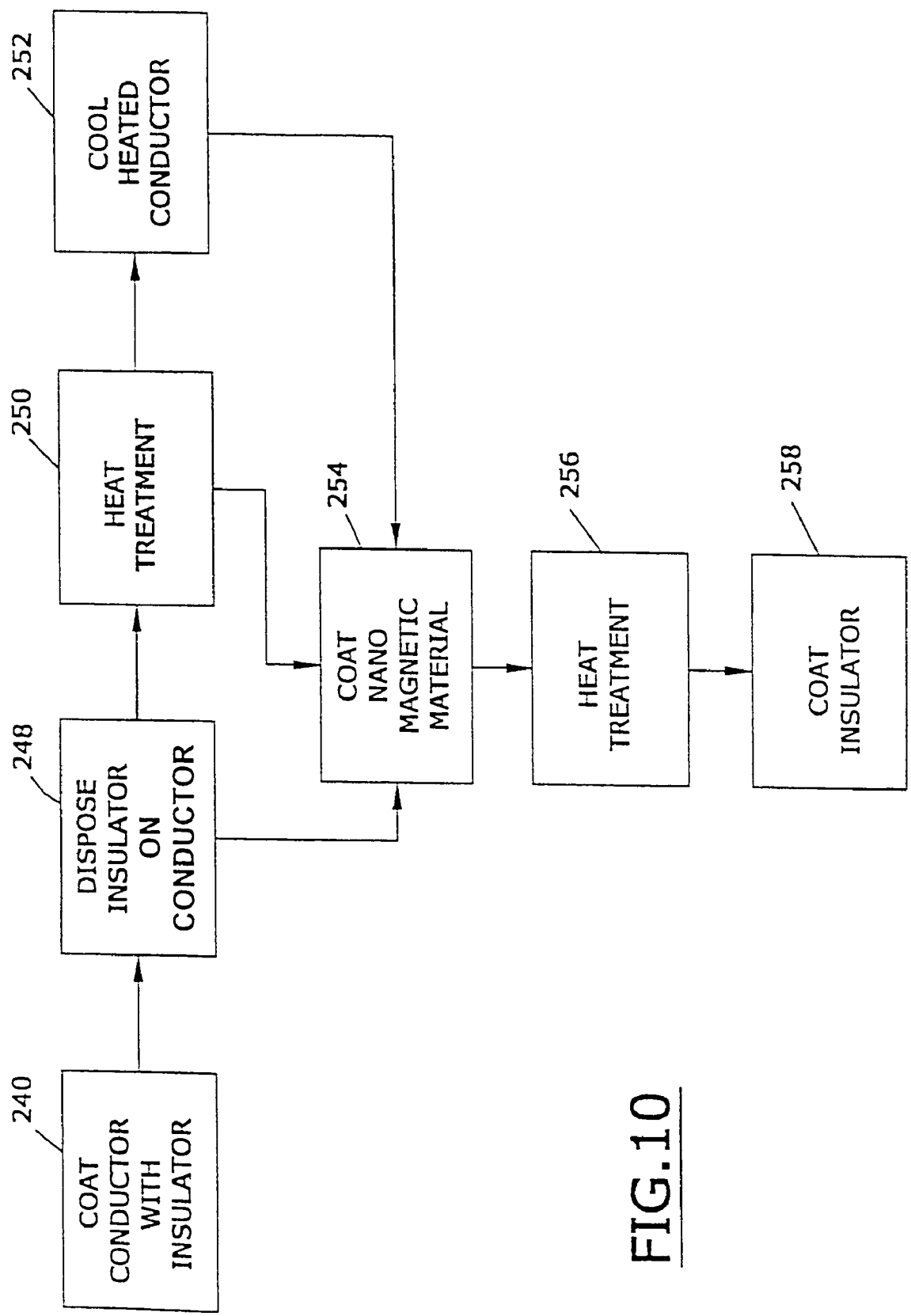
FIG. 10 is a flow diagram of a preferred process of the invention.

FIG. 10 is a flow diagram of a preferred process of the invention. In FIG. 1A, reference is made to one or more conductors as being the substrate(s); it is to be understood, however, that other substrate(s) material(s) and/or configurations also may be used.

In the first step of this process depicted in FIG. 10, step 240, the substrate 201 (see FIG. 8A) is coated with electrical insulative material. Suitable insulative materials include nano-sized silicon dioxide, aluminum oxide, cerium oxide, yttrium-stabilized zirconium, silicon carbide, silicon nitride, aluminum nitride, and the like. In general, these nano-sized particles will have a particle distribution such that at least 90 weight percent of the particles have a dimension in the range of from about 10 to about 100 nanometers.

The coated substrate 201 may be prepared by conventional means such as, e.g., the process described in U.S. Pat. No. 5,540,959.

Referring again to FIGS. 8C and 8D, and by way of illustration and not limitation, these Figures are sectional views of the coated substrate 201. It will be seen that, in the embodiments depicted, insulating material 205 separates the substrate and the layer of nanomagnetic material 202. In order to obtain the structure depicted in FIGS. 8C and 8D, one may first coat the substrate with insulating material 205, and then apply a coat of nanomagnetic material 202 on top of the insulating material 205; see, e.g., step 248 of FIG. 10.

The insulating material 205 that is disposed between substrate 201 and the layer of nanomagnetic coating 202 preferably has an electrical resistivity of from about $1 \times 10^9$ to about $1 \times 10^{13}$ ohm-centimeter.

After the insulating material 205 has been deposited, and in one preferred embodiment, the coated substrate is heat-treated in step 250 of FIG. 10. The heat treatment often is preferably used in conjunction with coating processes in which heat is required to bond the insulative material to the substrate 201.

The heat-treatment step 250 may be conducted after the deposition of the insulating material 205, or it may be conducted simultaneously therewith. In either event, and when it is used, it is preferred to heat the coated substrate 201 to a temperature of from about 200 to about 600 degree Centigrade for about 1 minute to about 10 minutes.

Referring again to FIG. 10, and in step 252 of the process, after the coated substrate 201 has been subjected to heat treatment step 250, the substrate is allowed to cool to a temperature of from about 30 to about 100 degree Centigrade over a period of time of from about 3 to about 15 minutes.

One need not invariably heat-treat and/or cool. Thus, referring to FIG. 10, one may immediately coat nanomagnetic particulate onto the coated substrate in step 254, after step 248 and/or after step 250 and/or after step 252.

In step 254, nanomagnetic material(s) are coated onto the previously coated substrate 201. This is best shown in FIGS. 8C and 8D, wherein the nanomagnetic materials are identified as 202.

In general, the thickness of the layer of nanomagnetic material deposited onto the coated substrate 201 is from about 100 nanometers to about 10 micrometers and, more preferably, from about 0.1 to 3 microns.

Referring again to FIG. 10, after the nanomagnetic material is coated in step 254, the coated substrate may be heat-treated in step 256. In this optional step 256, it is preferred to subject the coated substrate 201 to a temperature of from about 200 to about 600 degree Centigrade for from about 1 to about 10 minutes.

In one embodiment (not shown) additional insulating layers may be coated onto the substrate 201, by one or more of the processes disclosed hereinabove; see, e.g., optional step 258 of FIG. 10.

Without wishing to be bound to any particular theory, the applicants believe that the nanomagnetic particles 202 trap and pin magnetic lines of flux impinging on substrate 201, while at the same time minimizing or eliminating the flow of electrical currents through the coating and/or substrate.

Referring again to FIGS. 8A, 8B, 8C, and 8D, the layer of nanomagnetic particles 202 preferably has a saturation magnetization, at 25 degree Centigrade, of from about 1 to about 36,000 Gauss. In one embodiment, such saturation magnetization is from about 1 to about 26,000 Gauss. In another embodiment, the saturation magnetization at room temperature of the nanomagnetic particles is from about 500 to about 10,000 Gauss.

In one embodiment, it is preferred to utilize a thin film with a thickness of less than about 2 microns and a saturation magnetization in excess of 20,000 Gauss. The thickness of the layer of nanomagnetic material is measured from the bottom surface of such layer that contains such material to the top surface of such layer that contains such material; and such bottom surface and/or such top surface may be contiguous with other layers of material (such as insulating material) that do not contain nanomagnetic particles. Thus, e.g., one may make a thin film in accordance with the procedure described at page 156 of Nature, Volume 407, Sep. 14, 2000, that describes a multilayer thin film that has a saturation magnetization of 24,000 Gauss.

As will be apparent, even when the magnetic insulating properties of the assembly of this invention are not absolutely effective, the assembly still reduces the amount of electromagnetic energy that is transferred to the coated substrate, prevents the rapid dissipation of heat to bodily tissue, and minimization of disruption to the magnetic resonance image.

Figure 11:
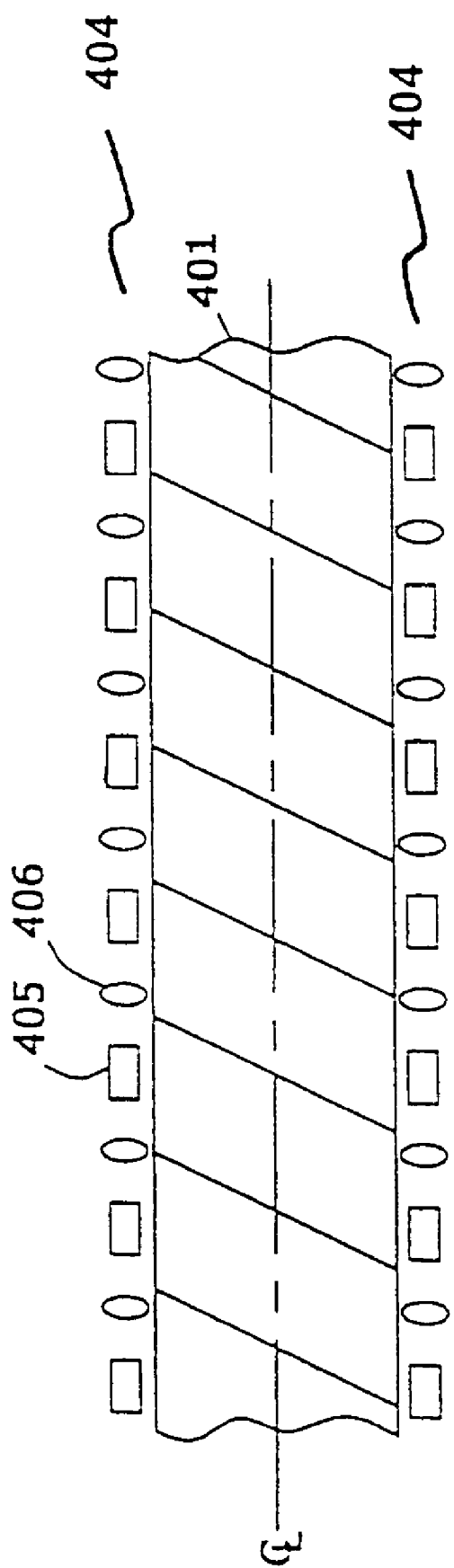
FIG. 11 is a schematic sectional view of a substrate, similar to the specific medical devices described in this application, coated with two different populations of elongated nanomagnetic particulate material.

FIG. 11 is a schematic sectional view of a substrate 401, which is part of an implantable medical device (not shown). Referring to FIG. 11, and in the preferred embodiment depicted therein, it will be seen that substrate 401 is coated with a layer 404 of nanomagnetic material(s). The layer 404, in the embodiment depicted, is comprised of nanomagnetic particulate 405 and nanomagnetic particulate 406. Each of the nanomagnetic particulate 405 and nanomagnetic particulate 406 preferably has an elongated shape, with a length that is greater than its diameter. In one aspect of this embodiment, nanomagnetic particles 405 have a different size than nanomagnetic particles 406. In another aspect of this embodiment, nanomagnetic particles 405 have different magnetic properties than nanomagnetic particles 406.

Referring again to FIG. 11, and in the preferred embodiment depicted therein, nanomagnetic particulate material 405 and nanomagnetic particulate material 406 are designed to respond to static or time-varying electromagnetic fields or effects in a manner similar to that of liquid crystal display (LCD) materials. More specifically, these nanomagnetic particulate materials 405 and nanomagnetic particulate materials 406 are designed to shift alignment and to effect switching from a magnetic shielding orientation to a non-magnetic shielding orientation. As will be apparent, the magnetic shield provided by layer 404, can be turned "ON" and "OFF" upon demand. In yet another embodiment (not shown), the magnetic shield is turned on when heating of the shielded object is detected.

Reference may be had to an article by Neil Mathur et al. entitled "Mesoscopic Texture in Magnanites" (January, 2003, Physics Today) for a discussion of the fact that " . . . in cetain oxides of manganese, a spectacularly diverse range of exotic electronic and magnetic phases can coexist at different locations within a single crystal. This striking behavior arises in manganites because their magnetic, electronic, and crystal structures interact strongly with one another. For example, a ferromagnetic metal can coexist with an insulator in which their electrons and their spins adopt intricate patterns."

Figure 12:
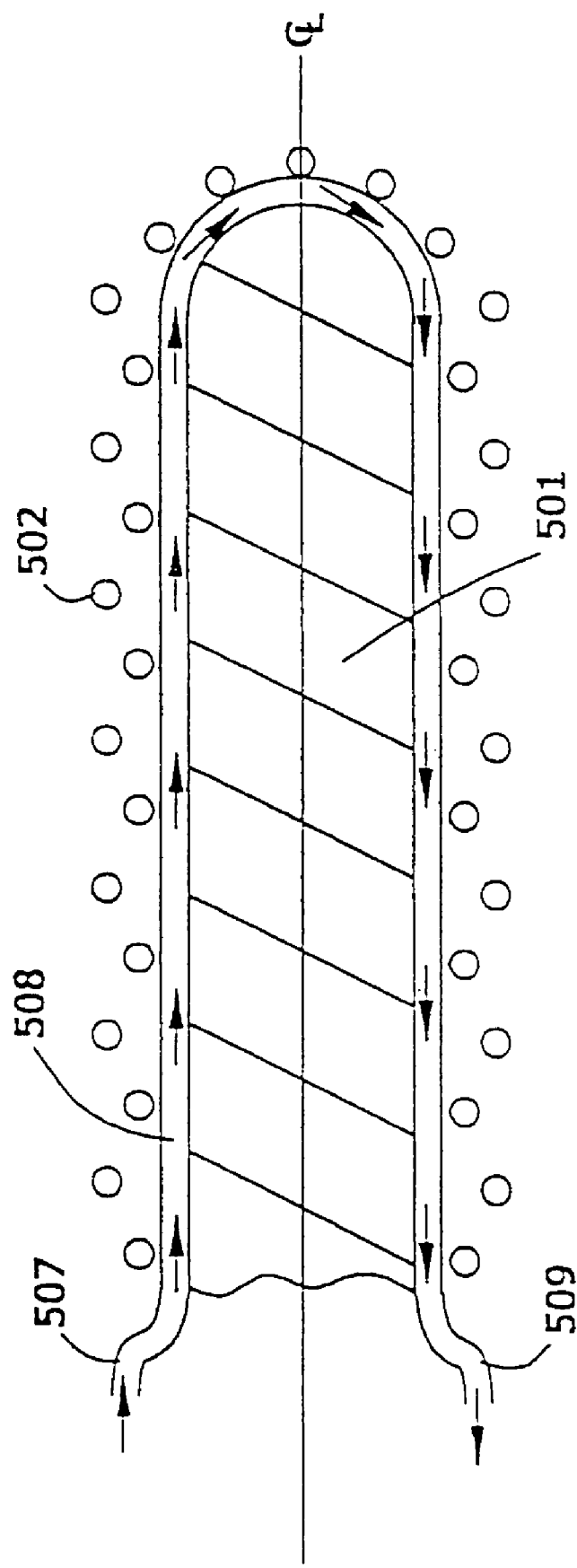
FIG. 12 is a schematic sectional view of an elongated cylinder, similar to the specific medical devices described in this application, coated with nanomagnetic particulate, wherein the cylinder includes a channel for active circulation of a heat dissipation fluid.

FIG. 12 is a schematic sectional view of substrate 501, which is part of an implantable medical device (not shown). Referring to FIG. 12, and to the embodiment depicted therein, it will be seen that substrate 501 is coated with nanomagnetic particulate material 502 which may differ from particulate material 202 (see FIGS. 8A through 8D) and/or particulate material 302 (see FIG. 9) and/or materials 405 or 406 (see FIG. 11). In the embodiment depicted in FIG. 12, the substrate 501 may be a cylinder, such as an enclosure for a catheter, medical stent, guidewire, and the like. The assembly depicted in FIG. 12 includes a channel 508 located on the periphery of the medical device. An actively circulating, heat-dissipating fluid (not shown) can be pumped into channel 508 through port 507, and exit channel 508 through port 509. The heat-dissipation fluid (not shown) will draw heat to another region of the device, including regions located outside of the body where the heat can be dissipated at a faster rate. In the embodiment depicted, the heat-dissipating fluid flows internally to the layer of nanomagnetic particles 502.

In another embodiment, not shown, the heat dissipating fluid flows externally to the layer of nanomagnetic particulate material 502.

In another embodiment (not shown), one or more additional polymer layers (not shown) are coated on top of the layer of nanomagnetic particulate 502. In one aspect of this embodiment, a high thermal conductivity polymer layer is coated immediately over the layer of nanomagnetic particulate 502; and a low thermal conductivity polymer layer is coated over the high thermal conductivity polymer layer. It is preferred that neither the high thermal conductivity polymer layer nor the low thermal conductivity polymer layer be electrically or magnetically conductive. In the event of the occurrence of "hot spots" on the surface of the medical device, heat from the localized "hot spots" will be conducted along the entire length of the device before moving radially outward through the insulating outer layer. Thus, heat is distributed more uniformly.

Many different devices advantageously incorporate the nanomagnetic film of this invention. In the following section of the specification, various additional devices that incorporate such film are described.

The disclosure in the following section of the specification relates generally to an implantable medical device that is immune or hardened to electromagnetic insult or interference. More particularly, the invention is directed to implantable medical devices that utilize shielding to harden or make these devices immune from electromagnetic insult (i.e. minimize or eliminate the amount of electromagnetic energy transferred to the device), namely magnetic resonance imaging (MRI) insult.

Magnetic resonance imaging (MRI) has been developed as an imaging technique to obtain images of anatomical features of human patients as well as some aspects of the functional activities of biological tissue; reference may be had, e.g., to John D. Enderle's "Introduction to Biomedical Engineering", Academic Press, San Diego, Calif., 2000 and, in particular, pages 783-841 thereof. Reference may also be had to Joseph D. Bronzino's "The Biomedical Engineering Handbook", CRC Press, Boca Raton, Fla., 1995, and in particular pages 1006-1045 thereof. These images have medical diagnostic value in determining the state of the health of the tissue examined.

In an MRI process, a patient is typically aligned to place the portion of the patient's anatomy to be examined in the imaging volume of the MRI apparatus. Such a MRI apparatus typically comprises a primary magnet for supplying a constant magnetic field, $B_0$, which is typically of from about 0.5 to about 10.0 Tesla, and by convention, is along the z-axis and is substantially homogenous over the imaging volume, and secondary magnets that can provide magnetic field gradients along each of the three principal Cartesian axis in space (generally x, y, and z or $x_1$, $x_2$, and $X_3$, respectively). A magnetic field gradient refers to the variation of the field along the direction parallel to $B_0$ with respect to each of the three principal Cartesian Axis. The apparatus also comprises one or more radio frequency (RF) coils, which provide excitation for and detection of the MRI signal. The RF excitation signal is an electromagnetic wave with an electrical field E and magnetic field $B_1$, and is typically transmitted at frequencies of 3-100 megahertz.

The use of the MRI process with patients who have implanted medical assist devices, such as guidewires, catheters, or stents, often presents problems. These implantable devices are sensitive to a variety of forms of electromagnetic interference (EMI), because the aforementioned devices contain metallic parts that can receive energy from the very intensive EMI fields used in magnetic resonance imaging. The above-mentioned devices may also contain sensing and logic and control systems that respond to low-level electrical signals emanating from the monitored tissue region of the patient. Since these implanted devices are responsive to changes in local electromagnetic fields, the implanted devices are vulnerable to sources of electromagnetic noise. The implanted devices interact with the time-varying radio-frequency (RF) magnetic field ($B_1$), which are emitted during the MRI procedure. This interaction can result in damage to the implantable device, or it can result in heating of the device, which in turn can harm the patient or physician using the device. This interaction can also result in degradation of the quality of the image obtained by the MRI process.

Signal loss and disruption of a magnetic resonance image can be caused by disruption of the local magnetic field, which perturbs the relationship between position and image, which are crucial for proper image reconstruction. More specifically, the spatial encoding of the MRI signal provided by the linear magnetic field can be disrupted, making image reconstruction difficult or impossible. The relative amount of artifact seen on an MR image due to signal disruption is dependent upon such factors as the magnetic susceptibility of the materials used in the implantable medical device, as well as the shape, orientation, and position of the medical device within the body of the patient, which is very often difficult to control.

All non-permanently magnetized materials have non-zero magnetic susceptibilities and are to some extent magnetic. Materials with positive magnetic susceptibilities less than approximately 0.01 are referred to as paramagnetic and are not overly responsive to an applied magnetic field. They are often considered non-magnetic. Materials with magnetic susceptibilities greater than 0.01 are referred to as ferromagnetic. These materials can respond very strongly to an applied magnetic field and are also referred as soft magnets as their properties do not manifest until exposed to an external magnetic field.

Paramagnetic materials (e.g. titanium), are frequently used to encapsulate and shield and protect implantable medical devices due to their low magnetic susceptibilities. These enclosures operate by deflecting electromagnetic fields. However, although paramagnetic materials are less susceptible to magnetization than ferromagnetic materials, they can also produce image artifacts due to eddy currents generated in the implanted medical device by externally applied magnetic fields, such as the radio frequency fields used in the MRI procedures. These eddy currents produce localized magnetic fields, which disrupt and distort the magnetic resonance image. Furthermore, the implanted medical device shape, orientation, and position within the body make it difficult to control image distortion due to eddy currents induced by the RF fields during MRI procedures. Also, since the paramagnetic materials are electrically conductive, the eddy currents produced in them can result in ohmic heating and injury to the patient. The voltages induced in the paramagnetic materials can also damage the medical device, by adversely interacting with the operation of the device. Typical adverse effects can include improper stimulation of internal tissues and organs, damage to the medical device (melting of implantable catheters while in the MRI coil have been reported in the literature), and/or injury to the patient.

Thus, it is desirable to provide protection against electromagnetic interference, and to also provide fail-safe protection against radiation produced by magnetic-resonance imaging procedures. Moreover, it is desirable to provide devices that prevent the possible damage that can be done at the tissue interface due to induced electrical signals and due to thermal tissue damage. Furthermore, it is desirable to provide devices that do not interact with RF fields which are emitted during magnetic-resonance imaging procedures and which result in degradation of the quality of the images obtained during the MRI process.

In one embodiment, there is provided a coating of nanomagnetic particles that consists of a mixture of aluminum oxide, iron, and other particles that have the ability to deflect electromagnetic fields while remaining electrically non-conductive. Preferably the particle size in such a coating is approximately 10 nanometers. Preferably the particle packing density is relatively low so as to minimize electrical conductivity. Such a coating when placed on a fully or partially metallic object (such as a guidewire, catheter, stent, and the like) is capable of deflecting electromagnetic fields, thereby protecting sensitive internal components, while also preventing the formation of eddy currents in the metallic object or coating. The absence of eddy currents in a metallic medical device provides several advantages, to wit: (1) reduction or elimination of heating, (2) reduction or elimination of electrical voltages which can damage the device and/or inappropriately stimulate internal tissues and organs, and (3) reduction or elimination of disruption and distortion of a magnetic-resonance image.

FIGS. 13A, 13B, and 13C are schematic views of a catheter assembly similar to the assembly depicted in FIG. 2 of U.S. Pat. No. 3,995,623; the entire disclosure of such patent is hereby incorporated by reference into this specification. Referring to FIG. 6 of such patent, and also to FIGS. 13A, 13B, and 13C, it will be seen that catheter tube 625 contains multiple lumens 603, 611, 613, and 615, which can be used for various functions such as inflating balloons, enabling electrical conductors to communicate with the distal end of the catheter, etc. While four such lumens are shown, it is to be understood that this invention applies to a catheter with any number of lumens.

The similar catheter disclosed and claimed in U.S. Pat. No. 3,995,623 may be shielded by coating it in whole or in part with a coating of nanomagnetic particulate.

In the embodiment depicted in FIG. 13A, interior nanomagnetic material 650a is applied to the interior wall of catheter 625, or exterior nanomagnetic material 650b is applied to the exterior wall of catheter 625, or imbibed nanomagnetic material 650c my be imbibed into the walls of catheter 625, or any combination of these locations.

In the embodiment depicted in FIG. 13B, internal nanomagnetic material 650d is applied to the interior walls of multiple lumens 603/611/613/615 within a single catheter 625. Additionally, nonmagnetic materials 650b and 650c are located on the external wall of catheter 625 or imbibed into the common wall.

In the embodiment depicted in FIG. 13C, a nanomagnetic material 650e is applied to the mesh-like material 636 used within the wall of catheter 625 to give it desired mechanical properties.

In another embodiment (not shown) a sheath coated with nanomagnetic material on its internal surface, exterior surface, or imbibed into the wall of such sheath, is placed over a catheter to shield it from electromagnetic interference. In this manner, existing catheters can be made MRI safe and compatible. The modified catheter assembly thus produced is resistant to electromagnetic radiation.

FIGS. 14A through 14G are schematic views of a catheter assembly 700 consisting of multiple concentric elements. While two elements are shown; 720 and 722, it is to be understood that any number of overlapping elements may be used, either concentrically or planarly positioned with respect to each other.

Referring to FIGS. 14A through 14G, and in the preferred embodiment depicted therein, it will be seen that catheter assembly 700 comprises an elongated tubular construction having a single, central or axial lumen 710. The exterior catheter body 722 and concentrically positioned internal catheter body 720 with internal lumen 712 are preferably flexible, i.e., bendable, but substantially non-compressible along its length. The catheter bodies 720 and 722 may be made of any suitable material. A presently preferred construction comprises an outer wall 722 and inner wall 720 made of a polyurethane, silicone, or nylon. The outer wall 722 preferably comprises an imbedded braided mesh of stainless steel or the like to increase torsional stiffness of the catheter assembly 700 so that, when a control handle, not shown, is rotated, the tip sectionally of the catheter will rotate in corresponding manner. The catheter assembly 700 may be shielded by coating it in whole or in part with a coating of nanomagnetic particulate, in any one or more of the following manners:

Referring to FIG. 14A, a nanomagnetic material 650f may be coated on the outside surface of the inner concentrically positioned catheter body 720.

Referring to FIG. 14B, a nanomagnetic material 650g may be coated on the inside surface 713 of the inner concentrically positioned catheter body 720.

Referring to FIG. 14C, a nanomagnetic material 650h may be imbibed into the walls of the inner concentrically positioned catheter body 720 and externally positioned catheter body 722. Although not shown, a nanomagnetic material may be imbibed solely into either inner concentrically positioned catheter body 720 or externally positioned catheter body 722.

Referring to FIG. 14D, a nancmagnetic material 650f may be coated onto the exterior wall of the inner concentrically positioned catheter body 720 and external wall 715 (see element 650i). Referring to FIG. 14E, a nanomagnetic material 650g may be coated onto the interior wall 713 of the inner concentrically positioned catheter body 720 and the external wall 715 of externally positioned catheter body 722.

Referring to FIG. 14F, a nanomagnetic material 650i may be coated on the outside surface 715 of the externally positioned catheter body 722.

Referring to FIG. 14G, a nanomagnetic material 650j may be coated onto the exterior surface of an internally positioned solid element 727.

By way of further illustration, one may apply nanomagnetic particulate material to one or more of the catheter assemblies disclosed and claimed in U.S. Pat. Nos. 5,178, 803; 5,041,083; 6,283,959; 6,270,477; 6,258,080; 6,248,092; 6,238,408; 6,208,881; 6,190,379; 6,171,295; 6,117,064; 6,019,736; 6,017,338; 5,964,757; 5,853,394; and 6,235,024; the entire disclosure of which is hereby incorporated by reference into this specification. The catheters assemblies disclosed and claimed in the above-mentioned United States patents may be shielded by coating them in whole or in part with a coating of nanomagmetic particulate. The modified catheter assemblies thus produced are resistant to electromagnetic radiation.

Figure 15A:
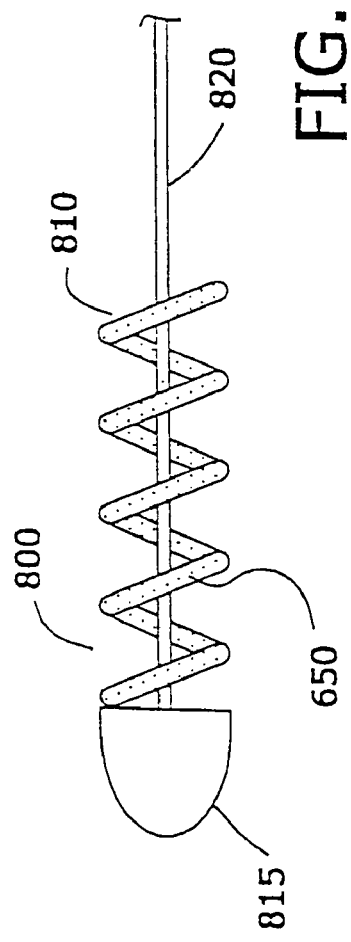
FIGS. 15A, 15B and 15C are schematic views of an implantable guidewire coated with nanomagnetic particulate material.
Figure 15B:
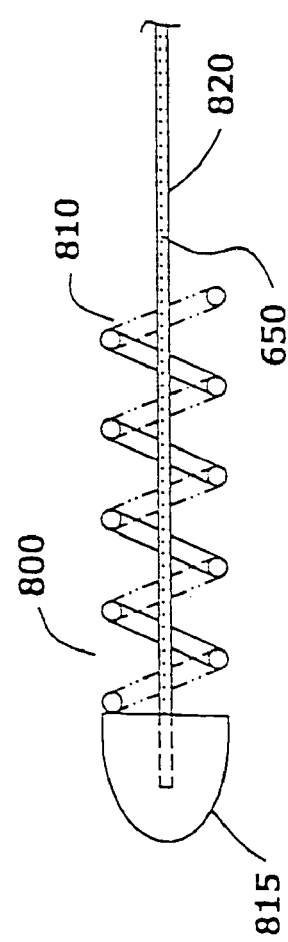
Figure 15C:
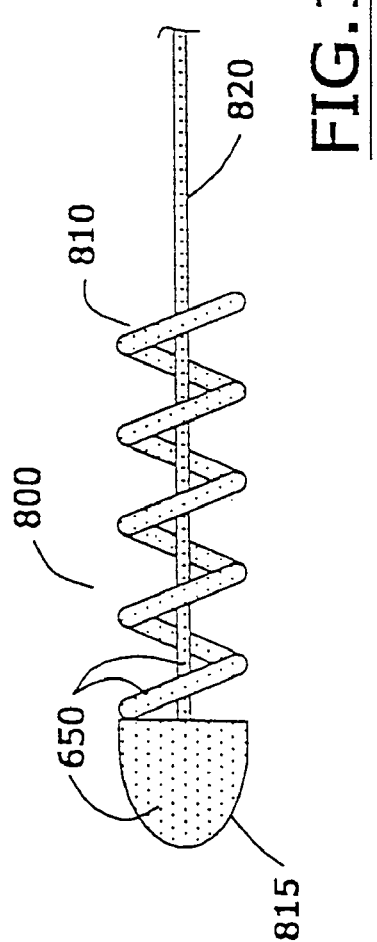

FIGS. 15A, 15B, and 15C are schematic views of a guidewire assembly 800 for insertion into vascular vessel (not shown), and it is similar to the assembly depicted in U.S. Pat. No. 5,460,187; the entire disclosure of such patent is incorporated by reference into this specification. Referring to FIG. 15A, a coiled guidewire 810 is formed of a proximal section (not shown) and central support wire 820 which terminates in hemispherical shaped tip 815. The proximal end has a retaining device (not shown) enables the person operating the guidewire to turn and orient the guidewire within the vascular conduit.

The guidewire assembly may be shielded by coating it in whole or in part with a coating of nanomagnetic particulate.

In the embodiment depicted in FIG. 15A; the nanomagnetic material 650 is coated on the exterior surface of the coiled guidewire 810. In the embodiment depicted in FIG. 15B; the nanomagnetic material 650 is coated on the exterior surface of the central support wire 820. In the embodiment depicted in FIG. 15C; the nanomagnetic material 650 is coated on all guidewire assembly components including coiled guidewire 810, tip 815, and central support wire 820. The modified guidewire assembly thus produced is resistant to electromagnetic radiation.

By way of further illustration, one may coat with nanomagnetic particulate matter the guidewire assemblies disclosed and claimed in U.S. Pat. Nos. 5,211,183; 6,168,604; 6,093, 157; 6,019,737; 6,001,068; 5,938,623; 5,797,857; 5,588,443; and 5,452,726; the entire disclosure of which is hereby incorporated by reference into this specification. The modified guidewire assemblies thus produced are resistant to electromagnetic radiation.

Figure 16A:
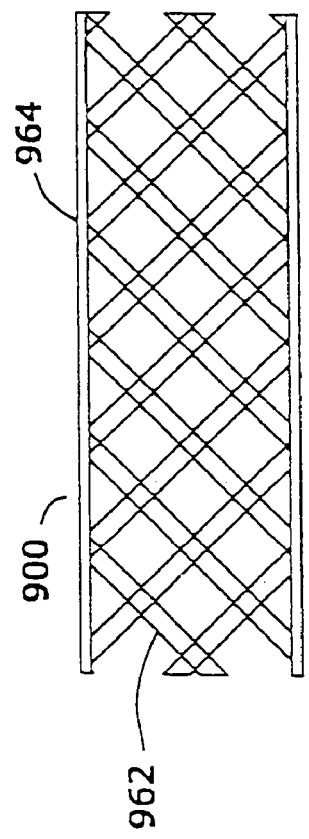
FIGS. 16A and 16B are schematic views of an implantable stent coated with nanomagnetic particulate material.
Figure 16B:
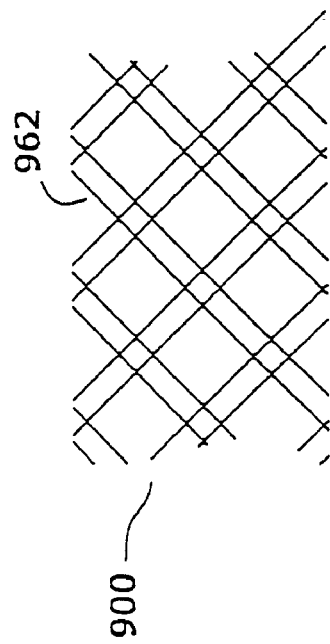

FIGS. 16A and 16B are schematic views of a medical stent assembly 900 similar to the assembly depicted in FIG. 15 of U.S. Pat. No. 5,443,496; the entire disclosure of such patent is hereby incorporated by reference into this specification.

Referring to FIG. 16A, a self-expanding stent 900 comprising joined metal stent elements 962 is shown. The stent 960 also comprises a flexible film 964. The flexible film 964 can be applied as a sheath to the metal stent elements 962 after which the stent 900 can be compressed, attached to a catheter, and delivered through a body lumen to a desired location. Once in the desired location, the stent 900 can be released from the catheter and expanded into contact with the body lumen, where it can conform to the curvature of the body lumen. The flexible film 964 is able to form folds, which allow the stent elements to readily adapt to the curvature of the body lumen. The medical stent assembly disclosed and claimed in U.S. Pat. No. 5,443,496 may be shielded by coating it in whole or in part with a nanomagnetic coating.

In the embodiment depicted in FIG. 16A, flexible film 964 is coated with a nanomagnetic coating on its inside or outside surfaces, or within the film itself.

In one embodiment, a stent (not shown) is coated with a nanomagnetic material.

It is to be understood that any one of the above embodiments may be used independently or in conjunction with one another within a single device.

In yet another embodiment (not shown), a sheath (not shown), coated or imbibed with a nanomagnetic material is placed over the stent, particularly the flexible film 964, to shield it from electromagnetic interference. In this manner, existing stents can be made MRI safe and compatible.

By way of further illustration, one may coat one or more of the medical stent assemblies disclosed and claimed in U.S. Pat. Nos. 6,315,794; 6,190,404; 5,968,091; 4,969,458; 6,342,068; 6,312,460; 6,309,412; and 6,305,436; the entire disclosure of each of which is hereby incorporated by reference into this specification. The medical stent assemblies disclosed and claimed in the above-mentioned United States patents may be shielded by coating them in whole or in part with a coating of nanomagmetic particulate, as described above. The modified medical stent assemblies thus produced are resistant to electromagnetic radiation.

Figure 17:
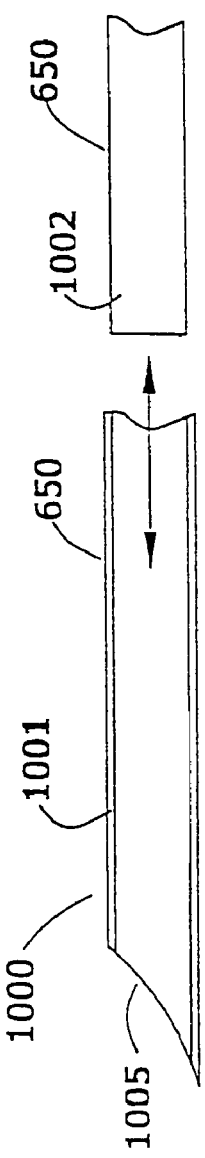
FIG. 17 is a schematic view of a biopsy probe coated with nanomagnetic particulate material.

FIG. 17 is a schematic view of a biopsy probe assembly 1000 similar to the assembly depicted in FIG. 1 of U.S. Pat. No. 5,005,585; the entire disclosure of such patent is hereby incorporated by reference into this specification. Such biopsy probe assembly 1000 is composed of three separate components, a hollow tubular cannula or needle 1001, a solid intraluminar rod-like stylus 1002, and a clearing rod or probe (not shown).

The components of the assembly 1000 are preferably formed of an alloy, such as stainless steel, which is corrosion resistant and non-toxic. Cannula 1001 has a proximal end (not shown) and a distal end 1005 that is cut at an acute angle with respect to the longitudinal axis of the cannula and provides an annular cutting edge.

By way of further illustration, biopsy probe assemblies are disclosed and claimed in U.S. Pat. Nos. 4,671,292; 5,437,283; 5,494,039; 5,398,690; and 5,335,663; the entire disclosure of each of which is hereby incorporated by reference into this specification. The biopsy probe assemblies disclosed and claimed in the above-mentioned United States patents may be shielded by coating them in whole or in part with a coating of nanomagmetic particulate. Thus, e.g., cannula 1001 may be coated, intraluminar stylus 1002 may be coated, and/or the clearing rod may be coated.

In one variation on this design (not shown), a biocompatible sheath is placed over the coated cannula 1001 to protect the nanomagnetic coating from abrasion and from contacting body fluids.

In another embodiment, the biocompatible sheath has on its interior surface or within its walls a nanomagnetic coating.

In yet another embodiment (not shown), a sheath coated or imbibed with a nanomagnetic material is placed over the biopsy probe, to shield it from electromagnetic interference. The modified biopsy probe assemblies thus produced are resistant to electromagnetic radiation.

Figure 18B:
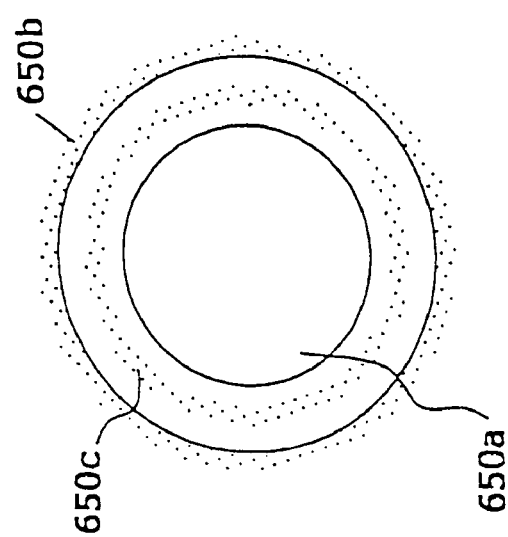
FIGS. 18A and 18B are schematic views of a tube of an endoscope coated with nanomagnetic particulate material.
Figure 18A:
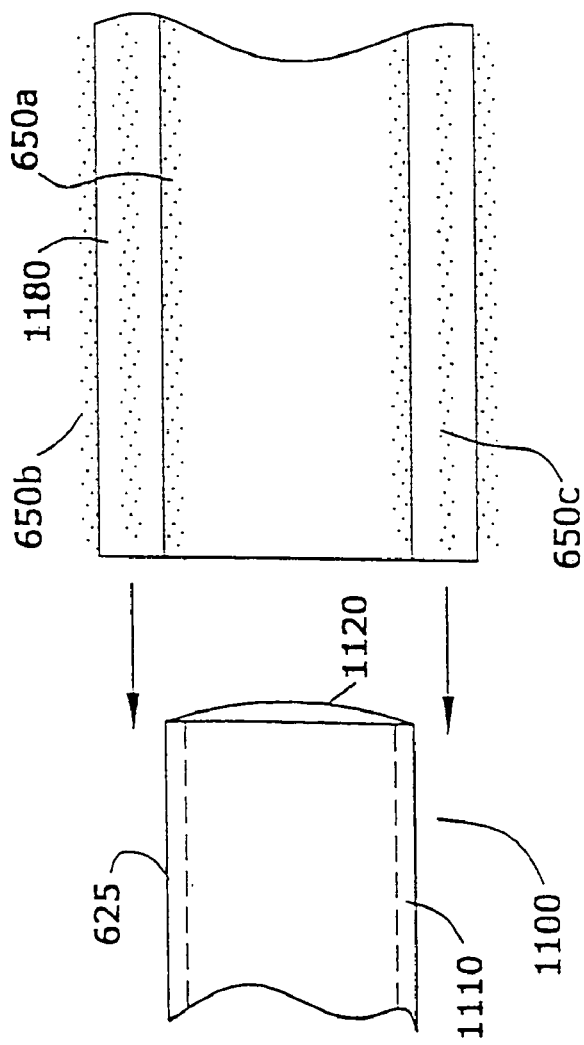

FIGS. 18A and 18B are schematic views of a flexible tube endoscope sheath assembly 1100 similar to the assembly depicted in FIG. 1 of U.S. Pat. No. 5,058,567; the entire disclosure of such patent is hereby incorporated by reference into this specification.

MRI is increasingly being used interoperatively to guide the placement of medical devices such as endoscopes which are very good at treating or examining tissues close up, but generally cannot accurately determine where the tissues being examined are located within the body.

Referring to FIG. 18A, the endoscope 1100 employs a flexible tube 1110 with a distally positioned objective lens 1120. Flexible tube 1110 is preferably formed in such manner that the outer side of a spiral tube is closely covered with a braided-wire tube (not shown) formed by weaving fine metal wires into a braid. The spiral tube is formed using a precipitation hardening alloy material, for example, beryllium bronze (copper-beryllium alloy).

By way of further illustration, other endoscope tube assemblies are disclosed and claimed in U.S. Pat. Nos. 4,868,015; 4,646,723; 3,739,770; 4,327,711; and 3,946,727; the entire disclosure of each of which is hereby incorporated by reference into this specification. The endoscope tube assemblies disclosed and claimed in the above-mentioned United States patents may be shielded by coating them in whole or in part with a coating of nanomagmetic particulate, material as described elsewhere in this specification.

Referring again to FIG. 18A; sheath 1180 is a sheath coated with nanomagnetic material 650a/650b/650c on its inside surface, its exterior surface, or imbibed into its structure; and such sheath 1180 is placed over the endoscope 1100, particularly the flexible tube 1110, to shield it from electromagnetic interference.

In yet another embodiment (not shown), flexible tube 1110 is coated with nanomagnetic materials on its internal surface, or imbibed with nanomagnetic materials within its wall.

In another embodiment (not shown), the braided-wire element within flexible tube 1110 is coated with a nanomagnetic material.

In this manner, existing endoscopes can be made MRI safe and compatible. The modified endoscope tube assemblies thus produced are resistant to electromagnetic radiation.

Figure 19A:
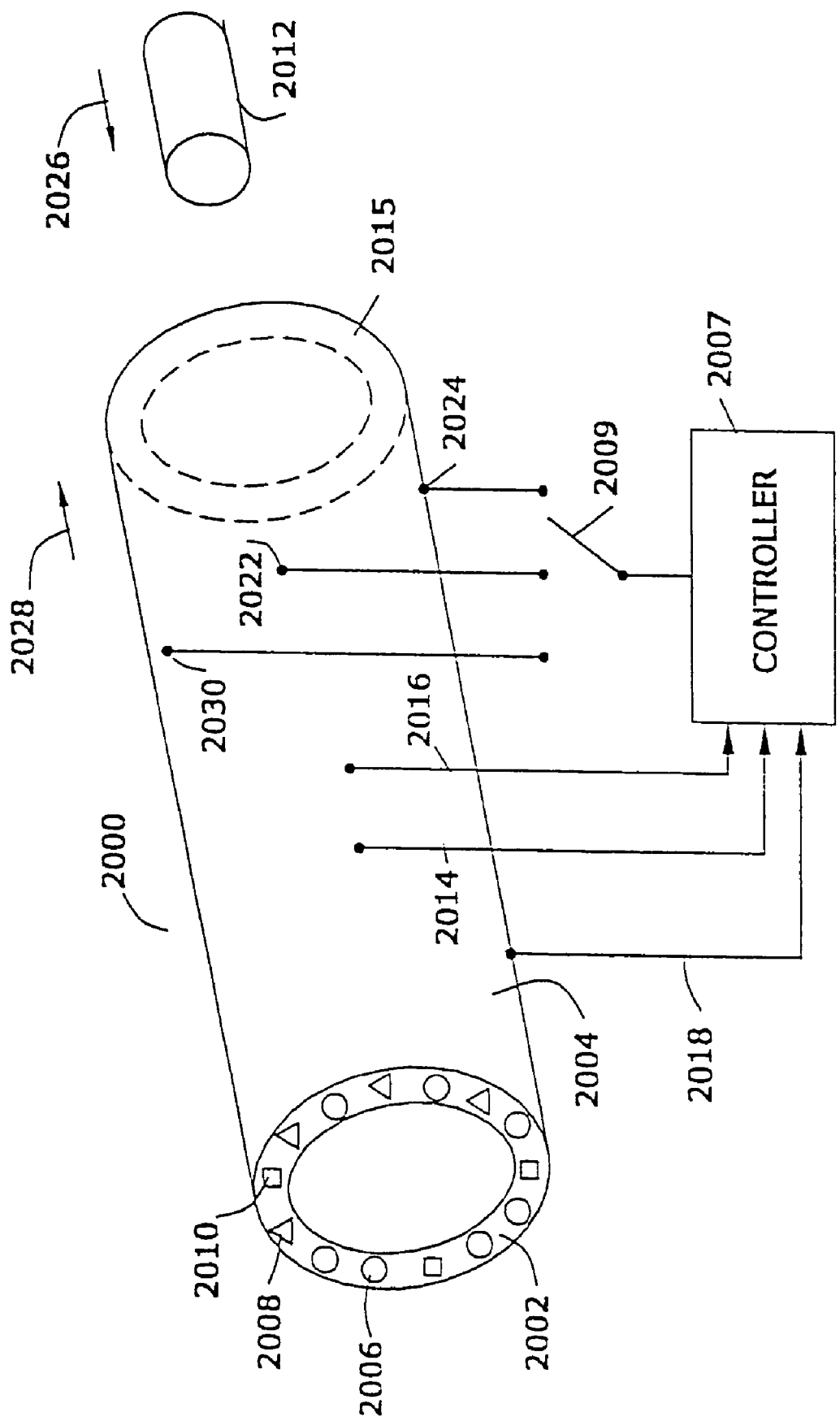
FIGS. 19A and 19B are schematics of one embodiment of the magnetically shielding assembly of this invention.
Figure 19B:
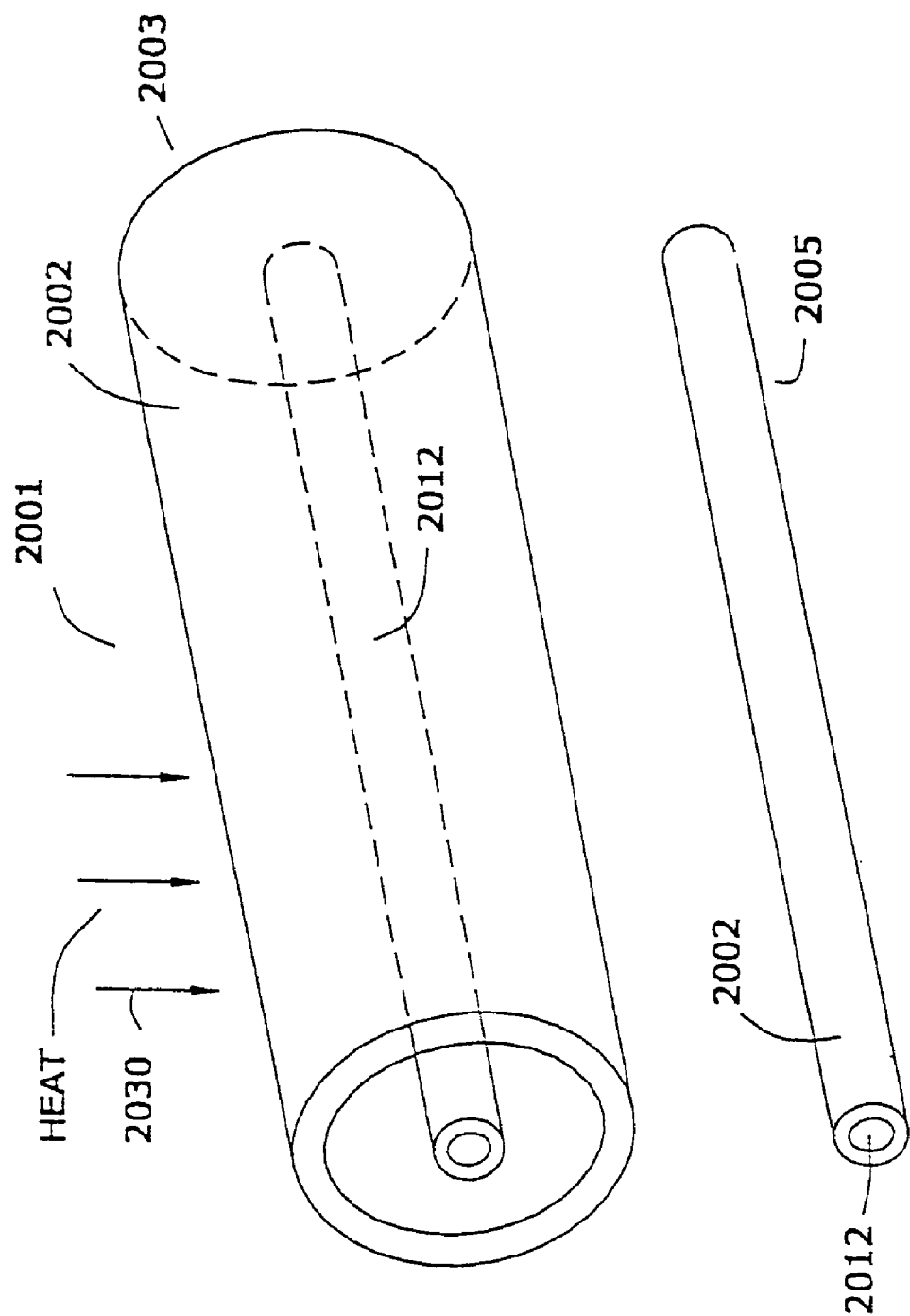

FIGS. 19A and 19B are schematic illustrations of a sheath assembly 2000 comprised of a sheath 2002 whose surface 2004 is comprised of a multiplicity of nanomagnetic materials 2006, 2008, and 2010. In one embodiment, the nanomagnetic material consists of or comprises nanomagnetic liquid crystal material. Additionally, nanomagnetic materials 2006, 2008, and 2010 may be placed on the inside surface of sheath 2002, imbibed into the wall of sheath 2002, or any combination of these locations.

The sheath 2002 may be formed from electrically conductive materials that include metals, carbon composites, carbon nanotubes, metal-coated carbon filaments (wherein the metal may be either a ferromagnetic material such as nickel, cobalt, or magnetic or non-magnetic stainless steel; a paramagnetic material such as titanium, aluminum, magnesium, copper, silver, gold, tin, or zinc; a diamagnetic material such as bismuth, or well known superconductor materials), metal-coated ceramic filaments (wherein the metal may be one of the following metals: nickel, cobalt, magnetic or non-magnetic stainless steel, titanium, aluminum, magnesium, copper, silver, gold, tin, zinc, bismuth, or well known superconductor materials, a composite of metal-coated carbon filaments and a polymer (wherein the polymer may be one of the following: polyether sulfone, silicone, polyimide, polyamide, polyvinylidene fluoride, epoxy, or urethane), a composite of metal-coated ceramic filaments and a polymer (wherein the polymer may be one of the following: polyether sulfone, silicone, polyimide, polyamide, polyvinylidene fluoride, epoxy, or urethane), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, cobalt, magnetic or non-magnetic stainless steel, titanium, aluminum, magnesium, copper, silver, gold, tin, zinc, bismuth, or well known superconductor materials), and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

In one preferred embodiment, the sheath 2002 is comprised of at least about 50 volume percent of the nanomagnetic material described elsewhere in this specification.

As is known to those skilled in the art, liquid crystals are nonisotropic materials (that are neither crystalline nor liquid) composed of long molecules that, when aligned, are parallel to each other in long clusters. These materials have properties intermediate those of crystalline solids and liquids. See, e.g., page 479 of George S. Brady et al.'s "Materials Handbook," Thirteenth Edition (McGraw-Hill, Inc., New York, 1991).

Ferromagnetic liquid crystals are known to those in the art, and they are often referred to as FMLC. Reference may be had, e.g., to U.S. Pat. Nos. 4,241,521; 6,451,207; 5,161,030; 6,375,330; 6,130,220; and the like. The entire disclosure of each of these United States patents is hereby incorporated by reference into this specification.

Reference also may be had to U.S. Pat. No. 5,825,448, which describes a reflective liquid crystalline diffractive light valve. The figures of this patent illustrate how the orientations of the magnetic liquid crystal particles align in response to an applied magnetic field. The entire disclosure of this United States patent is hereby incorporated by reference into this specification.

Referring again to FIG. 19A, and in the embodiment depicted therein, it will be seen that sheath 2002 may be disposed in whole or in part over medical device 2012. In the embodiment depicted, the sheath 2002 is shown as being bigger than the medical device 2012. It will be apparent that such sheath 2002 may be smaller than the medical device 2012, may be the same size as the medical device 2012, may have a different cross-sectional shape than the medical 2012, and the like.

In one preferred embodiment, the sheath 2002 is disposed over the medical device 2012 and caused to adhere closely thereto. One may create this adhesion either by use of adhesive(s) and/or by mechanical shrinkage.

In one embodiment, shrinkage of the sheath 2012 is caused by heat, utilizing well known shrink tube technology. Reference may be had, e.g., to U.S. Pat. Nos. 6,438,229; 6,245,053; 6,082,760; 6,055,714; 5,903,693; and the like. The entire disclosure of each of these United States patents is hereby incorporated by reference into this specification.

In another embodiment of the invention, the sheath 2002 is a rigid or flexible tube formed from polytetrafluoroethylene that is heat shrunk into resilient engagement with the implantable medical device. The sheath can also be formed from heat shrinkable polymer materials e.g., low density polyethylene (LDPE), linear low-density polyethylene (LLDPE), ethylene vinyl acrylate (EVA), ethylene methacrylate (EMA), ethylene methacrylate acid (EMAA) and ethyl glycol methacrylic acid (EGMA). The polymer material of the heat shrinkable sheath should have a Vicat softening point less than 50 degrees Centigrade and a melt index less than 25. A particularly suitable polymer material for the sheath of the invention is a copolymer of ethylene and methyl acrylate which is available under the trademark Lotryl 24MA005 from Elf Atochem. This copolymer contains 25% methyl acrylate, has a Vicat softening point of about 43 degree centigrade and a melt index of about 0.5.

In another embodiment of the invention, the sheath 2002 is a collapsible tube that can be extended over the implantable medical device such as by unrolling or stretching.

In yet another embodiment of the invention, the sheath 2002 contains a tearable seam along its axial length, to enable the sheath to be withdrawn and removed from the implantable device without explanting the device or disconnecting the device from any attachments to its proximal end, thereby enabling the electromagnetic shield to be removed after the device is implanted in a patient. This is a preferable feature of the sheath, since it eliminates the need to disconnect any devices connected to the proximal (external) end of the device, which could interrupt the function of the implanted medical device. This feature is particularly critical if the shield is being applied to a life-sustaining device, such as a temporary implantable cardiac pacemaker.

The ability of the sheath 1180 (see FIGS. 18A/18B) or 2002 (see FIGS. 19A/19B) to be easily removed, and therefore easily disposed, without disposing of the typically much more expensive medical device being shielded, is a preferred feature since it prevents cross-contamination between patients using the same medical device.

In still another embodiment of the invention, an actively circulating, heat-dissipating fluid can be pumped into one or more internal channels within the sheath. The heat-dissipation fluid will draw heat to another region of the device, including regions located outside of the body where the heat can be dissipated at a faster rate. The heat-dissipating flow may flow internally to the layer of nanomagnetic particles, or external to the layer of nanomagnetic particulate material.

FIG. 19B illustrates a process 2001 in which heat 2030 is applied to a shrink tube assembly 2003 to produce the final product 2005. For the sake of simplicity of representation, the controller 2007 has been omitted from FIG. 19B.

Referring again to FIG. 19A, and in the preferred embodiment depicted therein, it will be seen that a controller 2007 is connected by switch 2009 to the sheath 2002. A multiplicity of sensors 2014 and 2016, e.g., can detect the effectiveness of sheath 2002 by measuring, e.g., the temperature and/or the electromagnetic field strength within the shield 2002. One or more other sensors 2018 are adapted to measure the properties of sheath 2002 at its exterior surface 2004.

For the particular sheath embodiment utilizing a liquid crystal nanomagnetic particle construction, and depending upon the data received by controller 2007, the controller 2007 may change the shielding properties of shield 2002 by delivering electrical and/or magnetic energy to locations 2030, 2022, 2024, etc. The choice of the energy to be delivered, and its intensity, and its location, and its duration, will vary depending upon the status of the sheath 2002.

In the embodiment depicted in FIG. 19, the medical device may be moved in the direction of arrow 2026, while the sheath 2002 may be moved in the direction of arrow 2028, to produce the assembly 2001 depicted in FIG. 19B. Thereafter, heat may be applied to this assembly to produce the assembly 2005 depicted in FIG. 19B.

In one embodiment, not shown, the sheath 2002 is comprised of an elongated element consisting of a proximal end and a distal end, containing one or more internal hollow lumens, whereby the lumens at said distal end may be open or closed, is used to temporarily or permanently encase an implantable medical device.

In this embodiment, the elongated hollow element is similar to the sheath disclosed and claimed in U.S. Pat. No. 5,964,730; the entire disclosure of which is hereby incorporated by reference into this specification.

Referring again to FIG. 19A, and in the embodiment depicted therein, the sheath 2002 is preferably coated and/or impregnated with nanomagnetic shielding material 2006/2008/2010 that comprises at least 50 percent of its external surface, and/or comprises at least 50 percent of one or more lumen internal surfaces, or imbibed within the wall 2015 of sheath 2002, thereby protecting at least fifty percent of the surface area of one or more of its lumens, or any combination of these surfaces or areas, thus forming a shield against electromagnetic interference for the encased medical device.

Figure 20A:
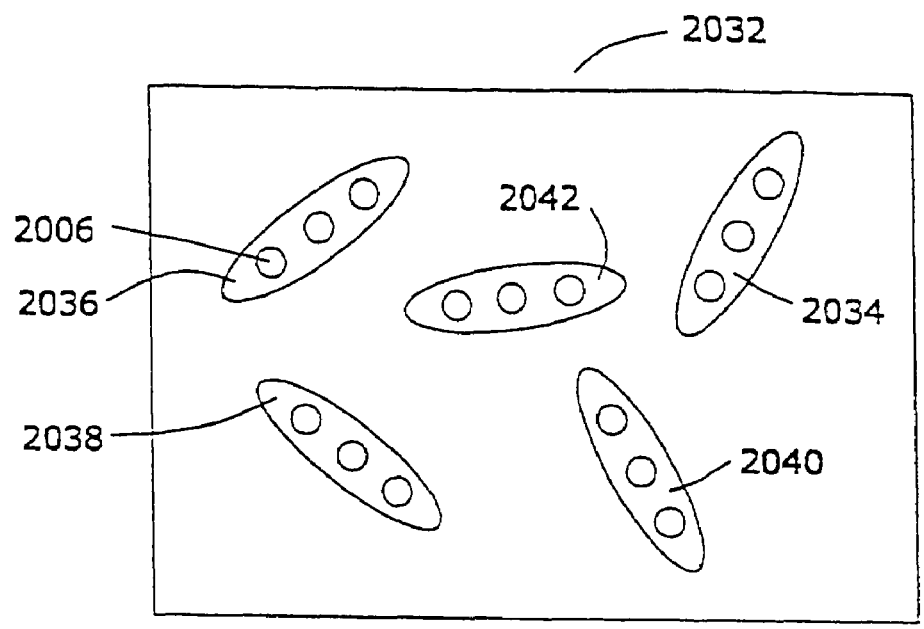
FIGS. 20A, 20B, 20C, 20D, 20E, and 20F are enlarged sectional views of a portion of a shielding assembly illustrating nonaligned and magnetically aligned nanomagnetic liquid crystal materials in different configurations.

FIG. 20A is a schematic of a multiplicity of liquid crystals 2034, 2036, 2038, 2040, and 2042 disposed within a matrix 2032. As will be apparent, each of these liquid crystals is comprised of nanomagnetic material 2006. In the configuration illustrated in FIG. 20A, the liquid crystals 2034 et seq. are not aligned.

Figure 20B:
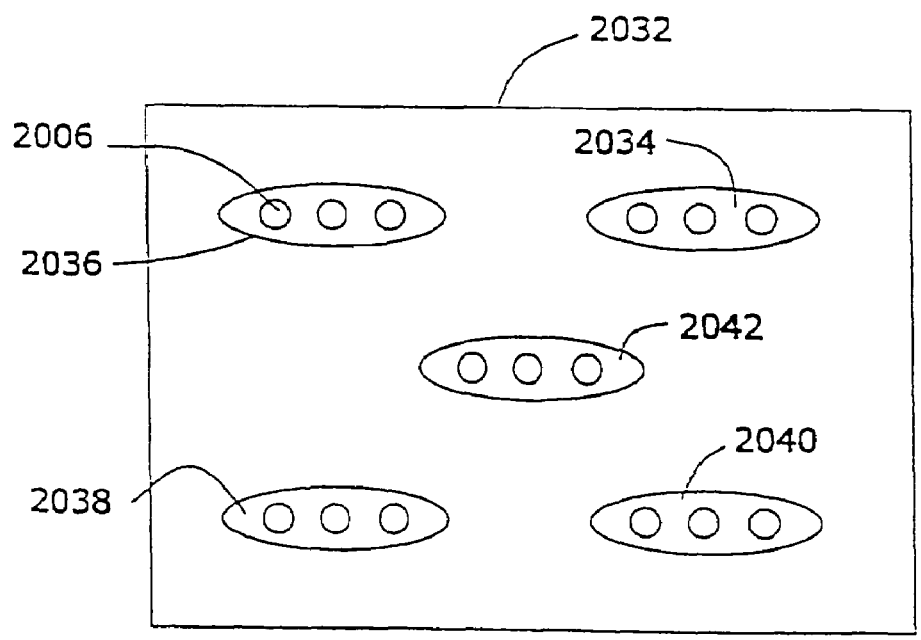

By comparison, in the configuration depicted in FIG. 20B, such liquid crystals 2034 are aligned. Such alignment is caused by the application of an external energy field (not shown).

Figure 20C:
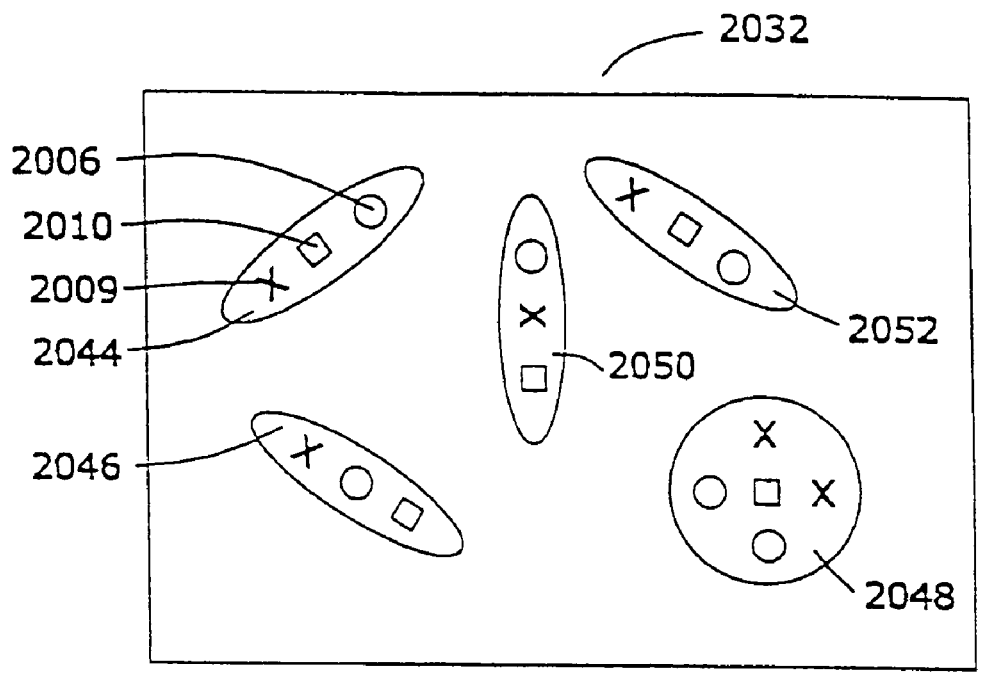
Figure 20D:
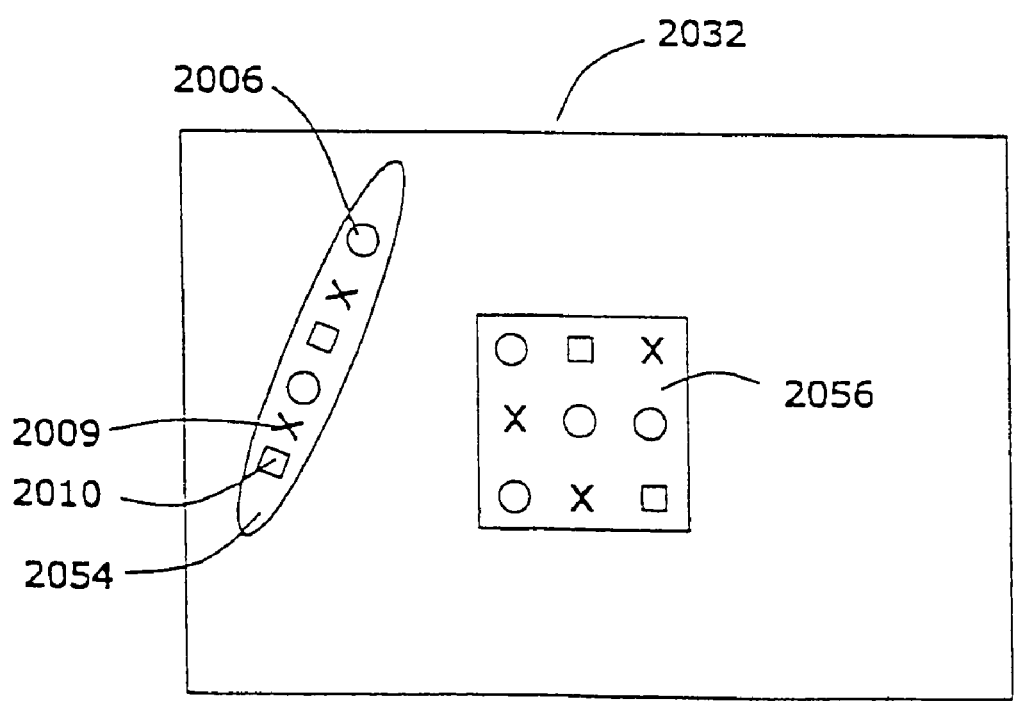
Figure 20E:
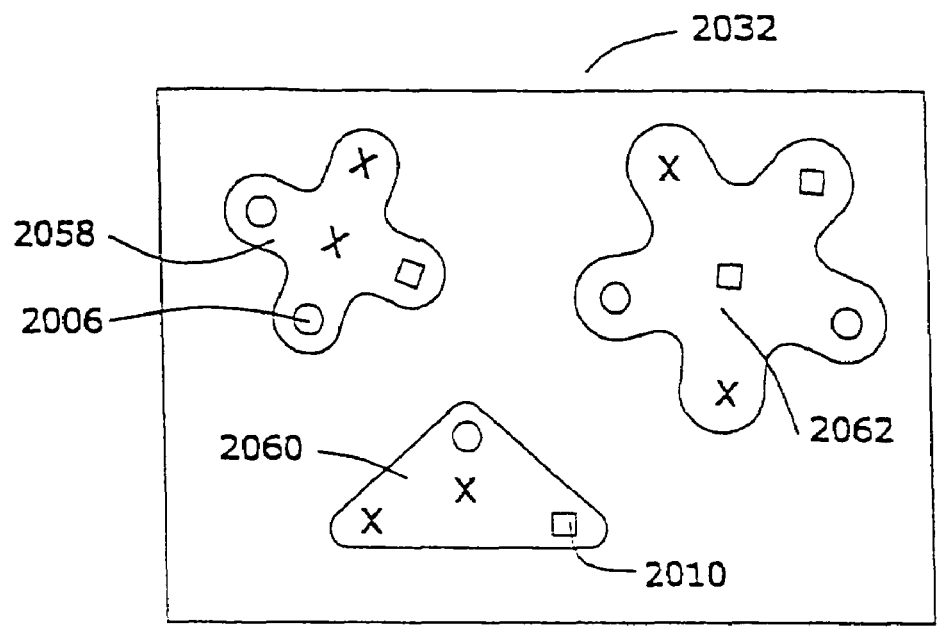
Figure 20F:
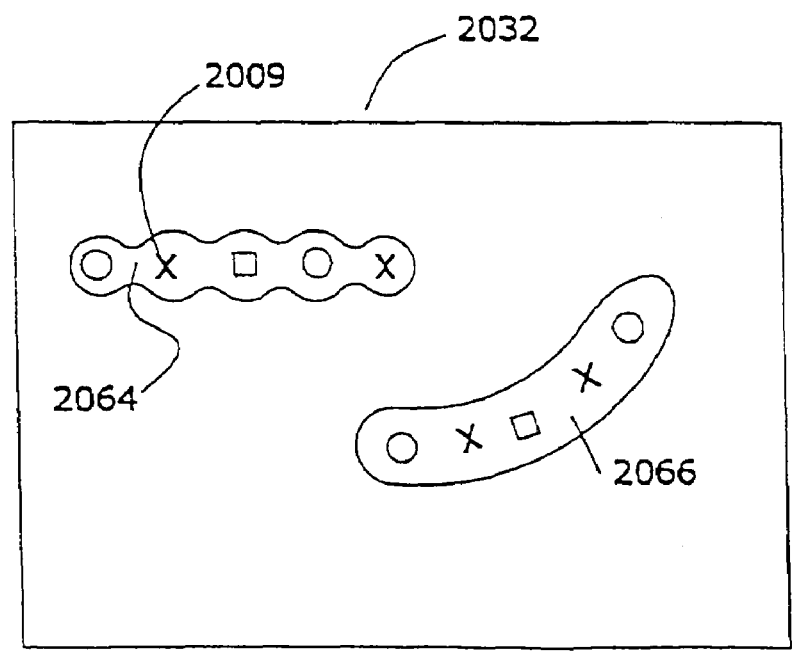

The liquid crystals disposed within the matrix 2032 (see FIGS. 20A through 20F) may have different concentrations and/or compositions of nanomagnetic particles 2006, 2009, and/or 2010; see FIG. 20C and liquid crystals 2044, 2046, 2048, 2050, and 2052. Alternatively, or additionally, the liquid crystals may have different shapes; see FIGS. 20D, 20E, and 20F and liquid crystals 2054 and 2056, 2058, 2060, 2062, 2064, and 2066. As will be apparent, by varying the size, shape, number, location, and/or composition of such liquid crystals, one may custom design any desired response.

Figure 21:
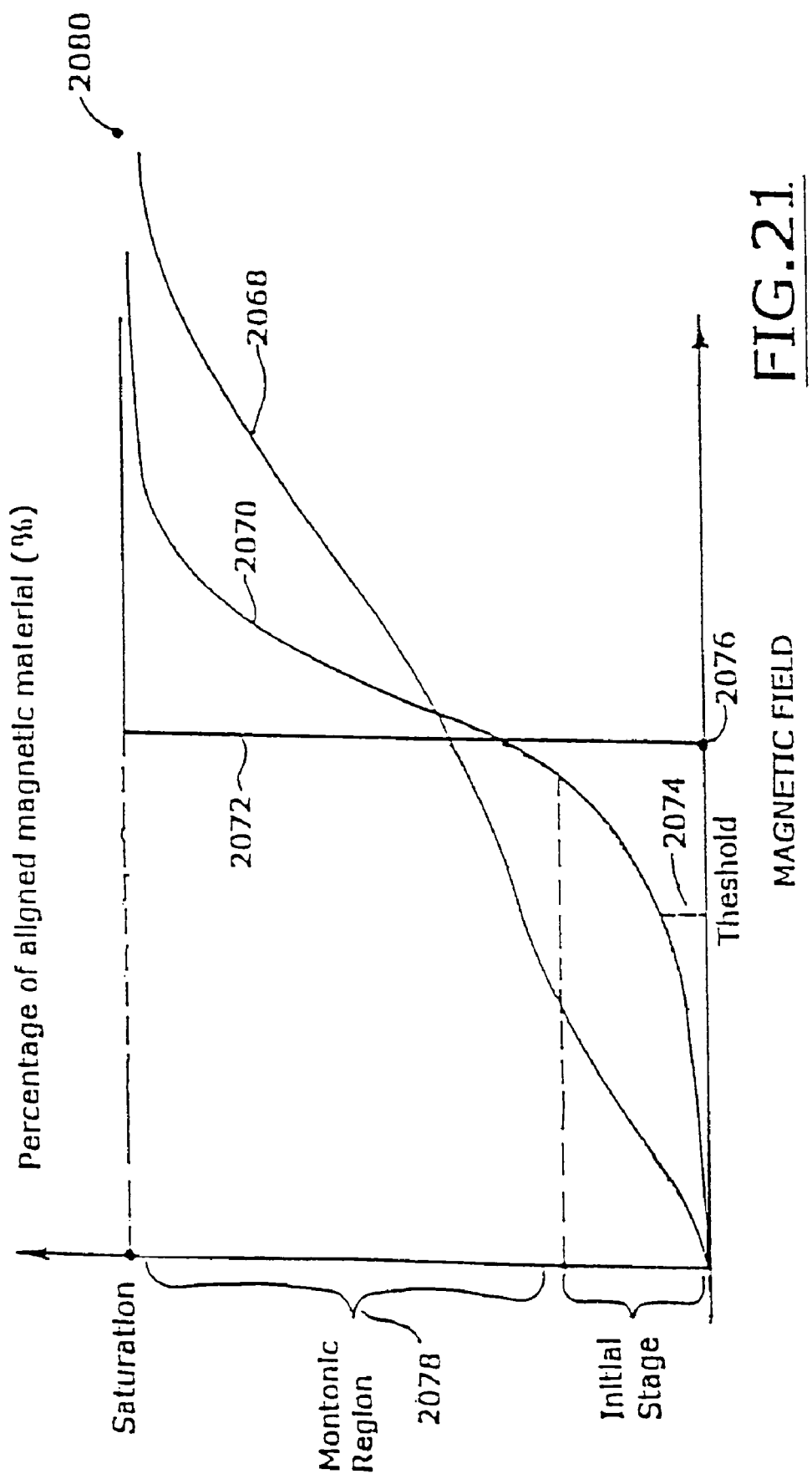
FIG. 21 is a graph showing the relationship of the alignment of the nanomagnetic liquid crystal material of FIGS. 20A and 20B with magnetic field strength.

FIG. 21 is a graph of the response of a typical matrix 2032 comprised of nanomagnetic liquid crystals. Three different curves, curves 2068, 2070, and 2072, are depicted, and they correspond to the responses of three different nanomagnetic liquid crystal materials have different shapes and/or sizes and/or compositions.

Referring to FIG. 21, and for each of curves 2068 through 2072, it will be seen that there is often a threshold point 2074 below which no meaningful response to the applied magnetic field is seen; see, e.g., the response for curve 2070.

It should be noted, however, that some materials have a low threshold before they start to exhibit response to the applied magnetic field; see, e.g., curve 2068. On the other hand, some materials have a very large threshold; see, e.g., threshold 2076 for curve 2072.

One may produce any desired response curve by the proper combination of nanomagnetic material composition, concentration, and location as well as liquid crystal geometries, materials, and sizes. Other such variables will be apparent to those skilled in the art.

Referring again to FIG. 21, it will be seen that there often is a monotonic region 2078 in which the increase of alignment of the nanomagnetic material is monotonic and often directly proportional; see, e.g., curve 2070.

There also is often a saturation point 2080 beyond which an increase in the applied magnetic field does not substantially increase the alignment.

As will be seen from the curves in FIG. 21, the process often is reversible. One may go from a higher level of alignment to a lower level by reducing the magnetic field applied.

Figure 22:
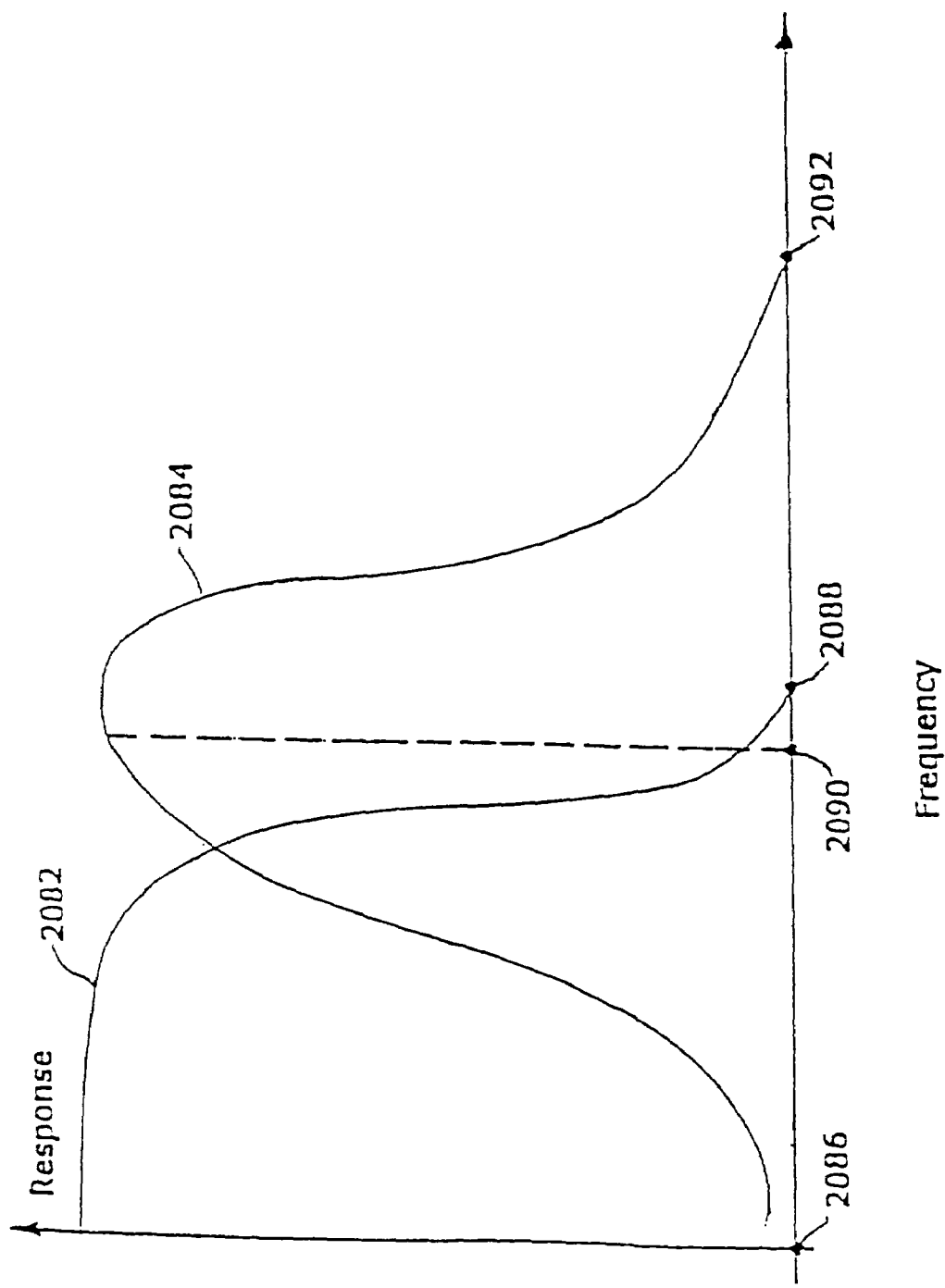
FIG. 22 is a graph showing the relationship of the attenuation provided by the shielding device of this invention as a function of frequency of the applied magnetic field.

The frequency of the magnetic field applied also influences the degree of alignment. As is illustrated in FIG. 22, for one nanomagnetic liquid crystal material (curve 2082), the response is at a maximum at an initial frequency 2086 but then decreases to a minimum at frequency 2088. By comparison, for another such curve (curve 2084), the response is minimum at frequency 2086, increases to a maximum at point 2090, and then decreases to a minimum at point 2092.

Thus, one may influence the response of a particular nanomagnetic liquid crystal material by varying its type of nanomagnetic material, and/or its concentration, and/or its shape, and/or the frequency to which it is subjected. Referring again to FIG. 19A, one may affect the shielding effectiveness of shield 2002 by supplying a secondary magnetic field (from controller 2007) at the secondary frequencies which will elicit the desired shielding effect.

Figure 23:
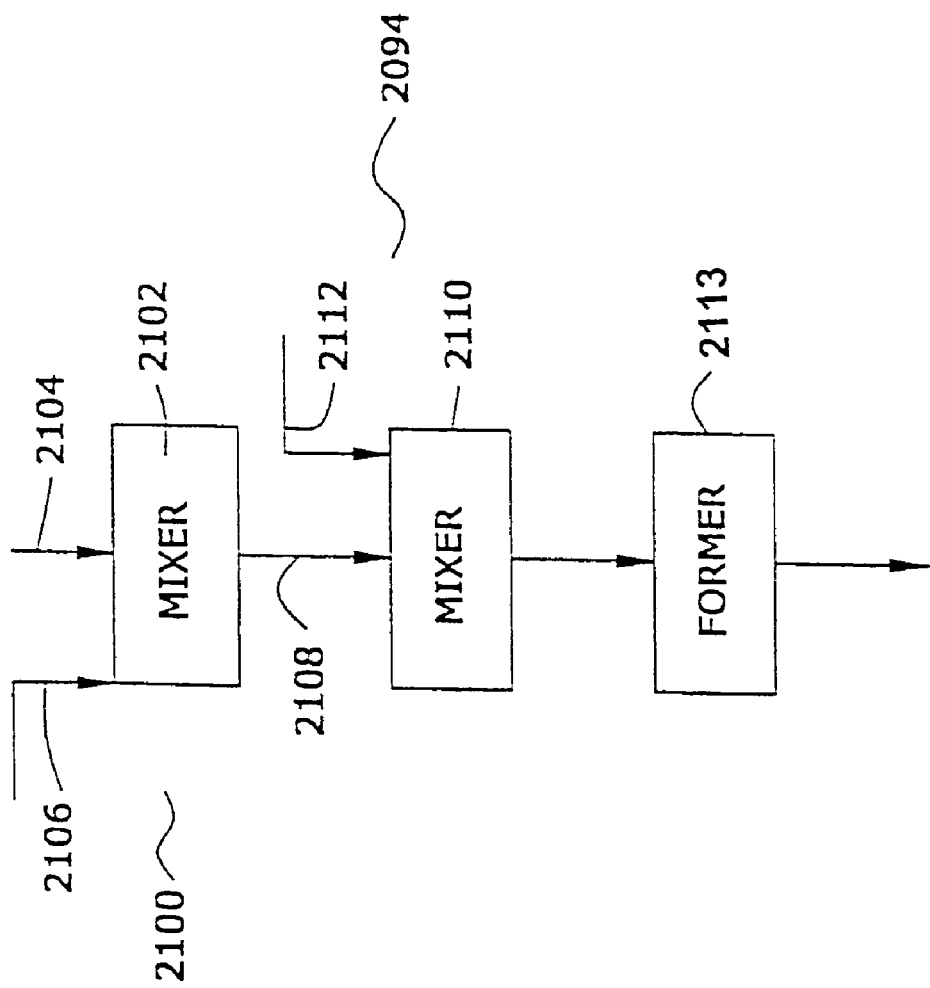
FIG. 23 is a flow diagram of one preferred process for preparing the nanomagnetic liquid crystal compositions of this invention.

FIG. 23 is a flow diagram illustrating a preferred process 2094 for making nanomagnetic liquid crystal material.

Referring to FIG. 23, and in step 2100, the nanomagnetic material of this invention is charged to a mixer 2102 via line 2104. Thereafter, suspending medium is also charged to the mixer 2102 via line 2106.

The suspending medium may be any medium in which the nanomagnetic material is dispersible. Thus, e.g., the suspending medium may be a gel, it may be an aqueous solution, it may be an organic solvent, and the like. In one embodiment, the nanomagnetic material is not soluble in the suspending medium; in this embodiment, a slurry is produced. For the sake of simplicity of description, the use of a polymer will be described in the rest of the process.

Referring again to FIG. 23, the slurry from mixer 2102 is charged via line 2108 to mixer 2110. Thereafter, or simultaneously, polymeric precursor of liquid crystal material is also charged to mixer 2102 via line 2104.

As is known to those skilled in the art, aromatic polyesters (liquid crystals) may be used as such polymeric precursor. These aromatic polyesters are commercially available as, e.g., Vectra (sold by Hoechst Celanese Engineering Plastic), Xydur (sold by Amoco Performance Plastics), Granlar (sold by Granmont), and the like. Reference may be had, e.g., to pages 649-650 of the aforementioned "Materials Handbook." Reference also may be had, e.g., to U.S. Pat. Nos. 4,738,880; 5,142,017; 5,006,402; 4,935,833; and the like. The entire disclosure of each of these United States patents is hereby incorporated by reference into this specification.

Referring again to FIG. 23, the liquid crystal polymer is mixed with the nanomagnetic particles for a time sufficient to produce a substantially homogeneous mixture. Typically, mixing occurs from about 5 to about 60 minutes.

The polymeric material formed in mixer 2110 then is formed into a desired shape in former 2113. Thus, and referring to Joel Frados' "Plastics Engineering Handbook," Fourth Edition (Van Nostrand Reinhold Company, New York, N.Y., 1976), one may form the desired shape by injection molding, extrusion, compression and transfer molding, cold molding, blow molding, rotational molding, casting, machining, joining, and the like. Other such forming procedures are well known to those skilled in the art.

One may prepare several different nanomagnetic structures and join them together to form a composite structure. One such composite structure is illustrated in FIG. 24.

Figure 24:
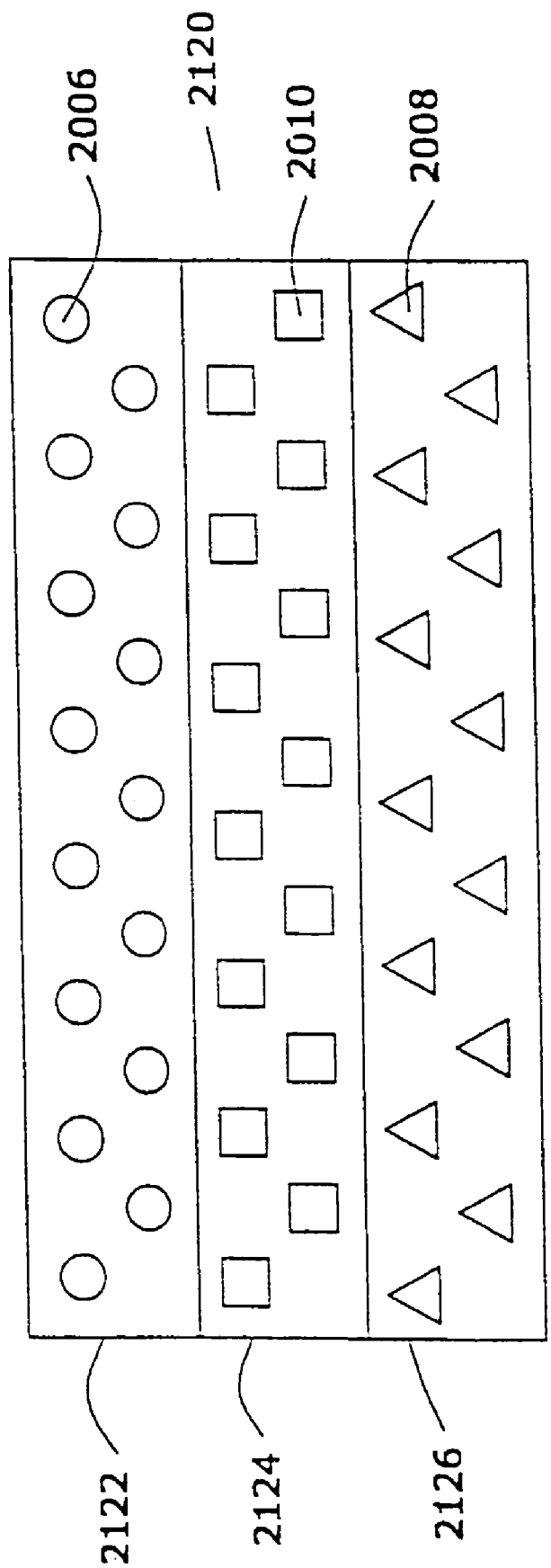
FIG. 24 is a sectional view of a multiplayer structure comprised of different nanomagnetic materials.

Referring to FIG. 24, assembly 2120 is comprised of nanomagnetic particles 2006, 2010, and 2008 disposed in layers 2122, 2124, and 2126, respectively. In the embodiment depicted, the layers 2122, 2124, and 2126 are contiguous with each, thereby forming a continuous assembly of nanomagnetic material, with different concentrations and compositions thereof at different points. The response of assembly 2120 to any particular magnetic field will vary depending upon the location at which such response is measured.

Figure 25:
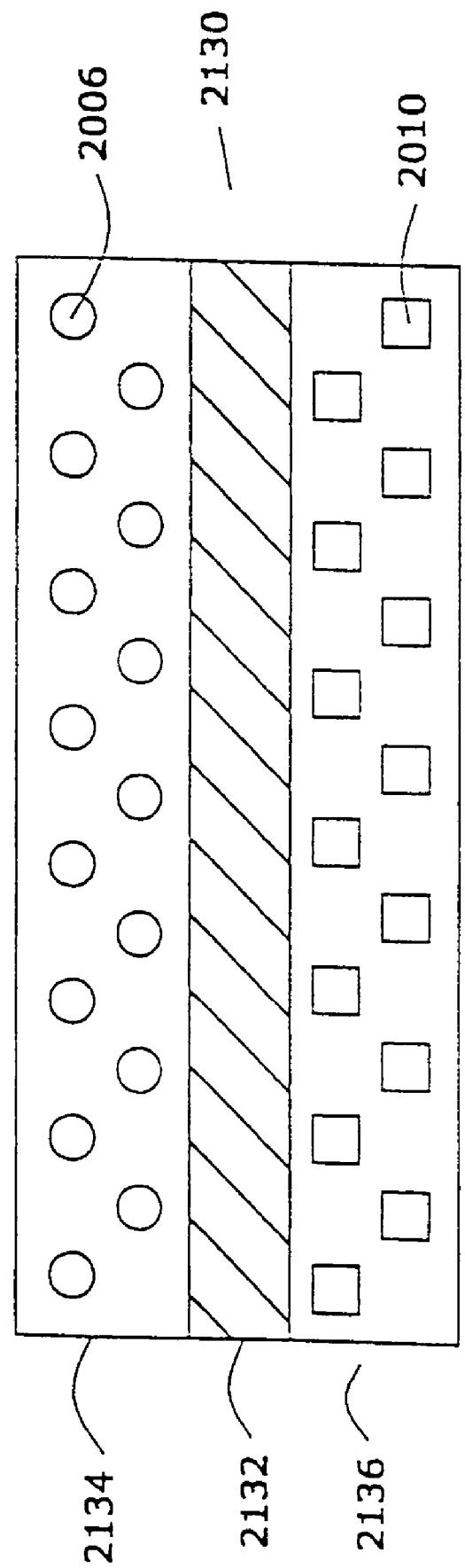
FIG. 25 is a sectional view of another multilayer structure comprised of different nanomagnetic materials and an electrical insulating layer.

FIG. 25 illustrates an assembly 2130 that is similar to assembly 2120 but that contains an insulating layer 2132 disposed between nanomagnetic layers 2134 and 2136. The insulating layer 2132 may be either electrically insulative and/or thermally insulative.

Figure 26:
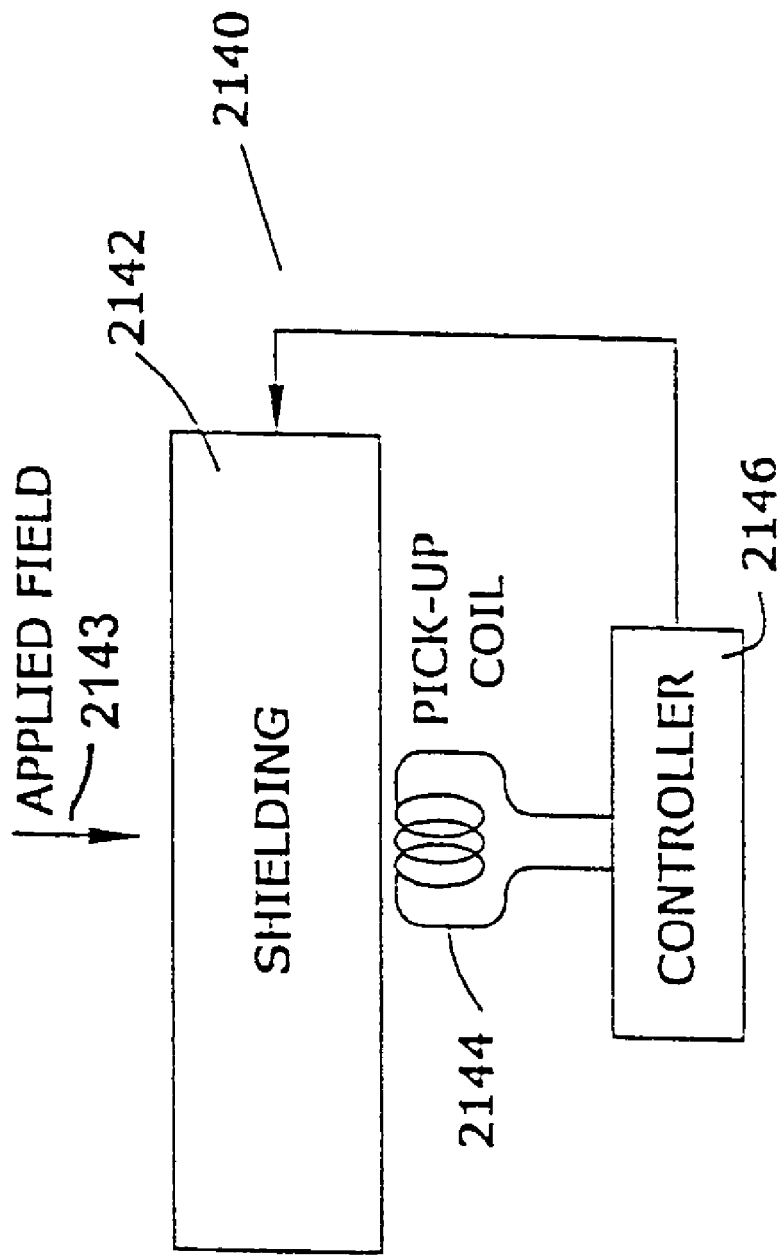
FIGS. 26 through 31 are schematic views of multilayer structures comprised of nanomagnetic material.

FIG. 26 illustrates an assembly 2140 in which the response of nanomagnetic material 2142 to an applied field 2143 is sensed by sensor 2144 that, in the embodiment depicted, is a pickup coil 2144. Data from sensor 2144 is transmitted to controller 2146. When and as appropriate, controller 2146 may introduce electrical and/or magnetic energy into shielding material 2142 in order to modify its response.

Figure 27:
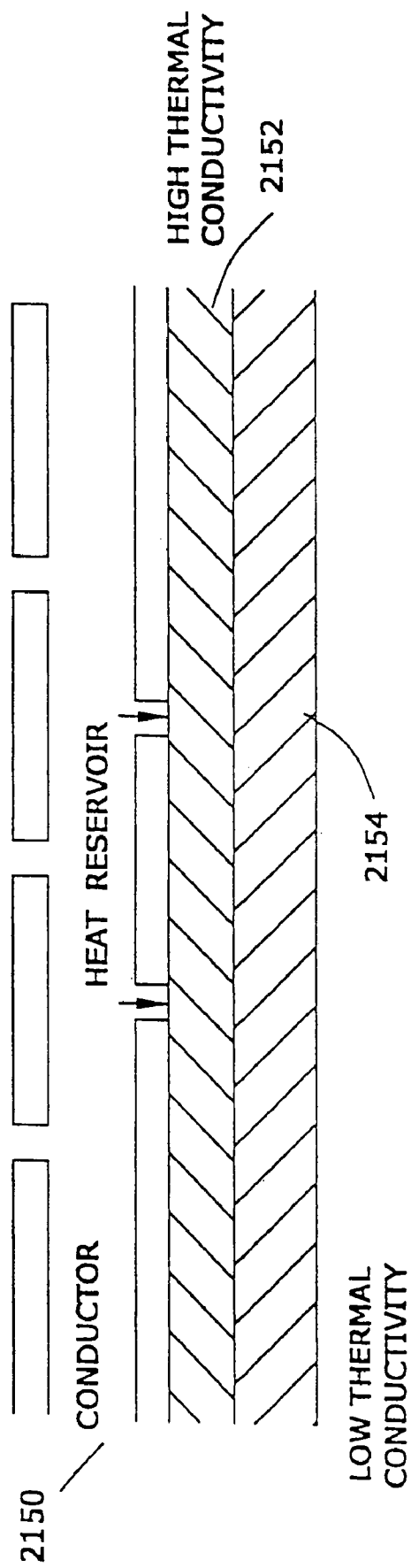

FIG. 27 is a schematic illustration of an assembly 2150. In the embodiment depicted, concentric insulating layers 2152 and 2154 preferably have substantially different thermal conductivities. Layer 2152 preferably has a thermal conductivity that is in the range of from about 10 to about 2000 calories per hour per square centimeter per centimeter per degree Celsius. Layer 2154 has a thermal conductivity that is in the range of from about 0.2 to about 10 calories per hour per square centimeter per centimeter per degree Celsius. Layers 2152 and 2154 are designed by choice of thermal conductivity and of layer thickness such that heat is conducted axially along, and circumferentially around, layer 2152 at a rate that is between 10 times and 1000 times higher than in layer 2154. Thus, in this embodiment, any heat that is generated at any particular site or sites in one or more nanomagnetic shielding layers will be distributed axially along the shielded element, and circumferentially around it, before being conducted radially to adjoining tissues. This will serve to further protect these adjoining tissues from thermogenic damage even if there are minor local flaws in the nanomagnetic shield.

Thus, in one embodiment of the invention, there is described a magnetically shielded conductor assembly, that contains a conductor, at least one layer of nanomagnetic material, a first thermally insulating layer, and a second thermally insulating layer. The first thermal insulating layer resides radially inward from said second thermally insulating layer, and it has a thermal conductivity from about 10 to about 2000 calories-centimeter per hour per square centimeter per degree Celsius. The second thermal insulating layer has a thermal conductivity from about 0.2 to about 10 calories per hour per square centimeter per degree Celsius, and the axial and circumferential heat conductance of the first thermal insulating layer is at least about 10 to about 1000 times higher than it is for said second thermal insulating layer.

In another embodiment of the invention, there is provided a magnetically shielded conductor assembly as discussed hereinabove, in which the first thermally insulating layer is disposed between said conductor and said layer of nanomagnetic material, and the second thermally insulating layer is disposed outside said layer of nanomagnetic material In another embodiment, there is provided a magnetically shielded conductor assembly as discussed hereinabove wherein the first thermally insulating layer is disposed outside the layer of nanomagnetic material, and wherein the second thermally insulating layer is disposed outside said first layer of thermally insulating material.

Figure 28:
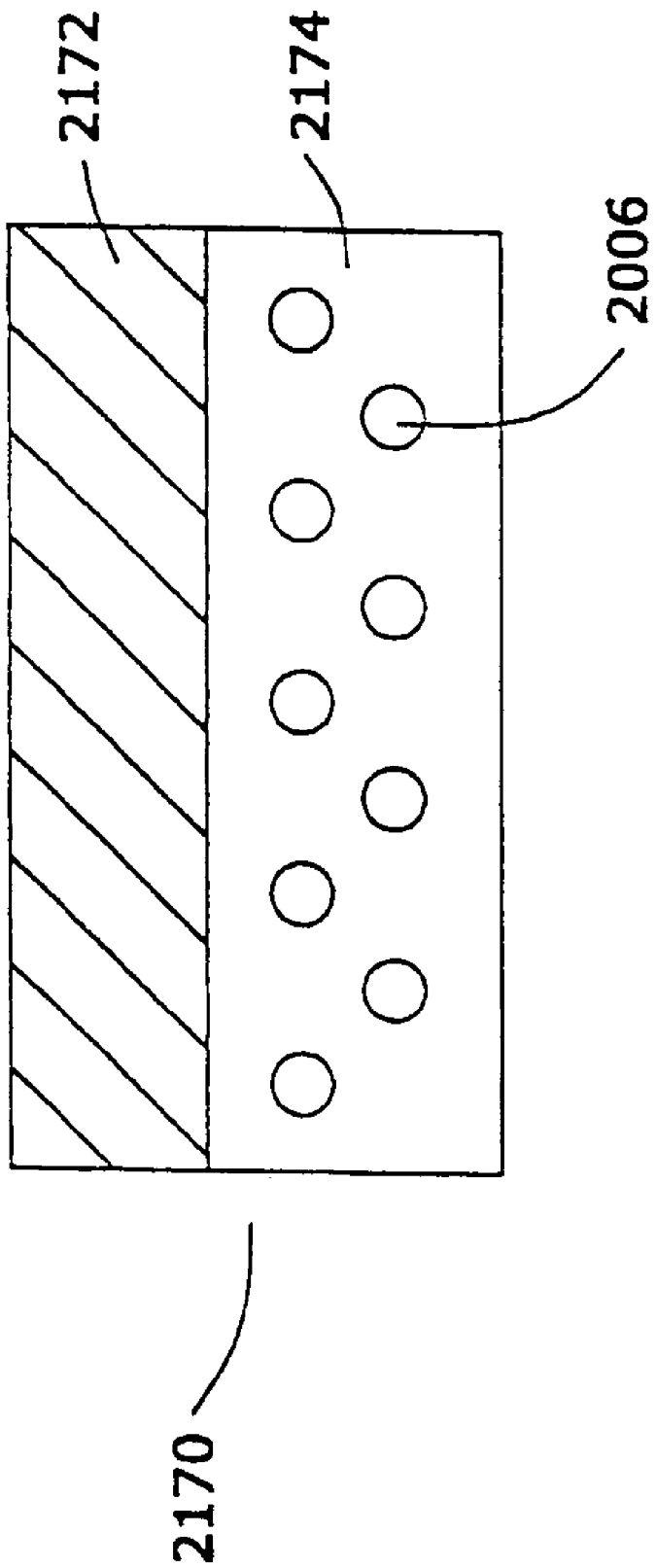

In another embodiment, the shield is comprised of a abrasion-resistant coating comprised of nanomagnetic material. Referring to FIG. 28, it will be seen that shield 2170 is comprised of abrasion resistant coating 2172 and nanomagnetic layer 2174.

A Composite Shield

In this portion of the specification, applicants will describe one embodiment of a composite shield of their invention. This embodiment involves a shielded assembly comprised of a substrate and, disposed above a substrate, a shield comprising from about 1 to about 99 weight percent of a first nanomagnetic material, and from about 99 to about 1 weight percent of a second material with a resistivity of from about 1 microohm-centimeter to about $1 \times 10^{25}$ microohm centimeters.

Figure 29:
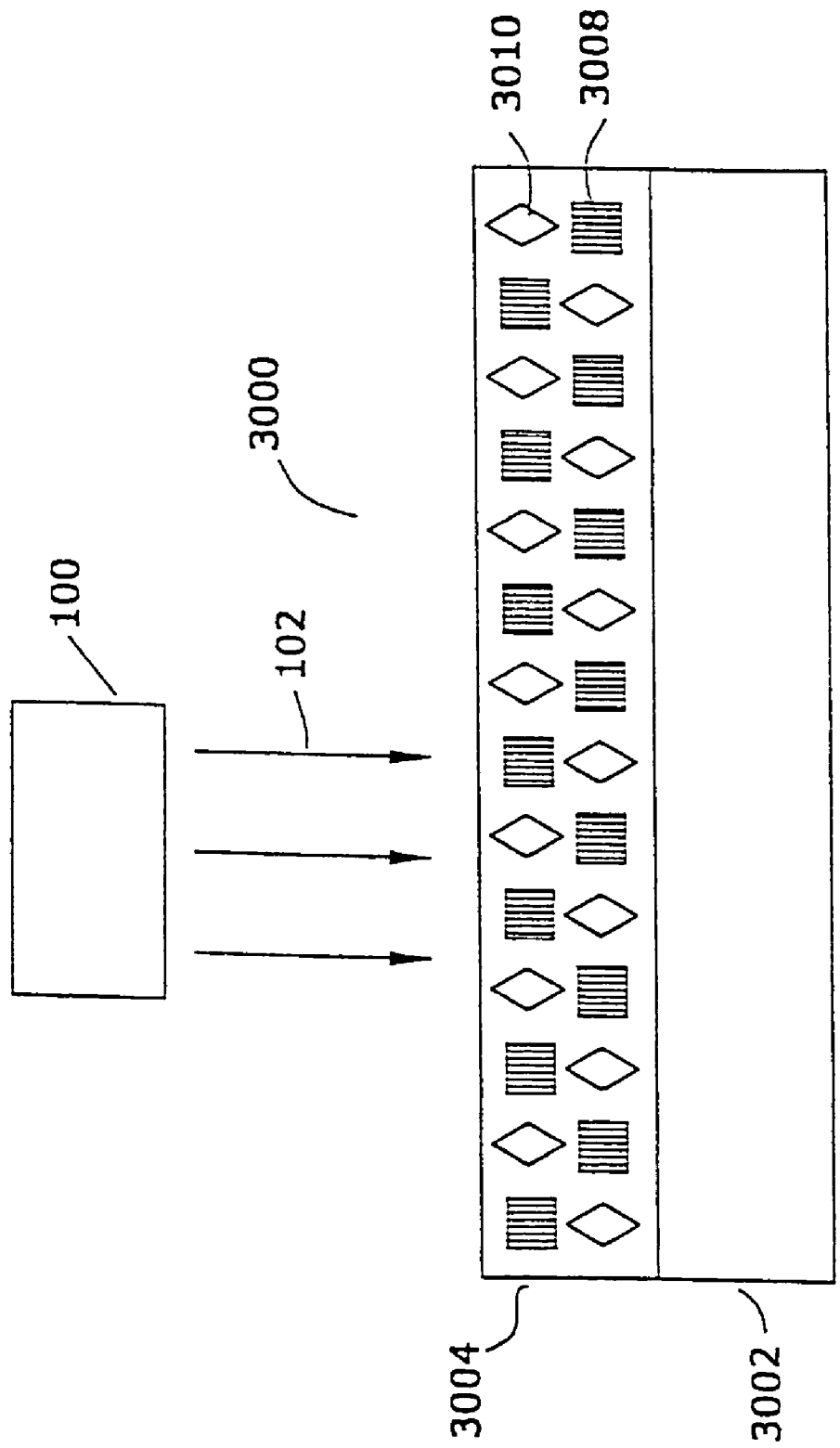

FIG. 29 is a schematic of a preferred shielded assembly 3000 that is comprised of a substrate 3002. The substrate 3002 may be any one of the substrates illustrated hereinabove. Alternatively, or additionally, it may be any receiving surface which it is desired to shield from magnetic and/or electrical fields. Thus, e.g., the substrate can be substantially any size, any shape, any material, or any combination of materials. The shielding material(s) disposed on and/or in such substrate may be disposed on and/or in some or all of such substrate.

By way of illustration and not limitation, the substrate 3002 may be, e.g., a foil comprised of metallic material and/or polymeric material. The substrate 3002 may, e.g., comprise ceramic material, glass material, composites, etc. The substrate 3002 may be in the shape of a cylinder, a sphere, a wire, a rectilinear shaped device (such as a box), an irregularly shaped device, etc.

In one embodiment, the substrate 3002 preferably has a thickness of from about 100 nanometers to about 2 centimeters. In one aspect of this embodiment, the substrate 3002 preferably is flexible.

Referring again to FIG. 29, and in the preferred embodiment depicted therein, it will be seen that a shield 3004 is disposed above the substrate 3002. As used herein, the term "above" refers to a shield that is disposed between a source 3006 of electromagnetic radiation 102 and the substrate 3002. The shield 3004 may be contiguous with the substrate 3002, or it may not be contiguous with the substrate 3002.

The shield 3004, in the embodiment depicted, is comprised of from about 1 to about 99 weight percent of nanomagnetic material 3008; such nanomagnetic material, and its properties, are described elsewhere in this specification. In one embodiment, the shield 3004 is comprised of at least about 40 weight percent of such nanomagnetic material 3008. In another embodiment, the shield 3004 is comprised of at least about 50 weight percent of such nanomagnetic material 3008.

Referring again to FIG. 29, and in the preferred embodiment depicted therein, it will be seen that the shield 3004 is also comprised of another material 3010 that preferably has an electrical resistivity of from about 1 microohm-centimeter to about $1 \times 10^{25}$ microohm-centimeters. This material 3010 is preferably present in the shield at a concentration of from about 1 to about 99 weight percent and, more preferably, from about 40 to about 60 weight percent.

In one embodiment, the material 3010 has a dielectric constant of from about 1 to about 50 and, more preferably, from about 1.1 to about 10. In another embodiment, the material 3010 has resistivity of from about 3 to about 20 microohm-centimeters.

In one embodiment, the material 3010 preferably is a nano-electrical material with a particle size of from about 5 nanometers to about 100 nanometers.

In another embodiment, the material 3010 has an elongated shape with an aspect ratio (its length divided by its width) of at least about 10. In one aspect of this embodiment, the material 3010 is comprised of a multiplicity of aligned filaments.

In one embodiment, the material 3010 is comprised of one or more of the compositions of U.S. Pat. Nos. 5,827,997 and 5,643,670. The entire disclosure of each of these United States patents is hereby incorporated by reference into this specification.

Thus, e.g., the material 3010 may comprise filaments, wherein each filament comprises a metal and an essentially coaxial core, each filament having a diameter less than about 6 microns, each core comprising essentially carbon, such that the incorporation of 7 percent volume of this material in a matrix that is incapable of electromagnetic interference shielding results in a composite that is substantially equal to copper in electromagnetic interference shielding effectives at 1-2 gigahertz. Reference may be had, e.g., to U.S. Pat. No. 5,827,997.

In another embodiment, the material 3010 is a particulate carbon complex comprising: a carbon black substrate, and a plurality of carbon filaments each having a first end attached to said carbon black substrate and a second end distal from said carbon black substrate, wherein said particulate carbon complex transfers electrical current at a density of 7000 to 8000 milliamperes per square centimeter for a $Fe^{+2}/Fe^{+3}$ oxidation/reduction electrochemical reaction couple carried out in an aqueous electrolyte solution containing 6 millmoles of potassium ferrocyanide and one mole of aqueous potassium nitrate.

In another embodiment, the material 3010 is a diamond-like carbon material. As is known to those skilled in the art, this diamond-like carbon material has a Mohs hardness of from about 2 to about 15 and, preferably, from about 5 to about 15. Reference may be had, e.g., to U.S. Pat. No. 5,098, 737 (amorphic diamond material); U.S. Pat. No. 5,658,470 (diamond-like carbon for ion milling magnetic material); U.S. Pat. No. 5,731,045 (application of diamond-like carbon coatings to tungsten carbide components); U.S. Pat. No. 6,037,016 (capacitatively coupled radio frequency diamond-like carbon reactor); U.S. Pat. No. 6,087,025 (application of diamond like material to cutting surfaces), and the like. The entire disclosure of each of these United States patents is hereby incorporated by reference into this specification.

In another embodiment, material 3010 is a carbon nanotube material. These carbon nanotubes generally have a cylindrical shape with a diameter of from about 2 nanometers to about 100 nanometers, and length of from about 1 micron to about 100 microns.

These carbon nanotubes are well known to those skilled in the art. Reference may be had, e.g., to U.S. Pat. No. 6,203,864 (heterojunction comprised of a carbon nanotube), U.S. Pat. No. 6,361,861 (carbon nanotubes on a substrate), U.S. Pat. No. 6,445,006 (microelectronic device comprising carbon nanotube components), U.S. Pat. No. 6,457,350 (carbon nanotube probe tip), and the like. The entire disclosure of each of these United States patents is hereby incorporated by reference into this specification.

In one embodiment, material 3010 is silicon dioxide particulate matter with a particle size of from about 10 nanometers to about 100 nanometers.

In another embodiment, the material 3010 is particulate alumina, with a particle size of from about 10 to about 100 nanometers. Alternatively, or additionally, one may use aluminum nitride particles, cerium oxide particles, yttrium oxide particles, combinations thereof, and the like; regardless of the particle(s) used in this embodiment, it is preferred that its particle size be from about 10 to about 100 nanometers.

In the embodiment depicted in FIG. 29, the shield 3004 is preferably in the form of a layer of material that has a thickness of from about 100 nanometers to about 10 microns. In this embodiment, both the nanomagnetic particles 3008 and the electrical particles 3010 are present in the same layer.

Figure 30:
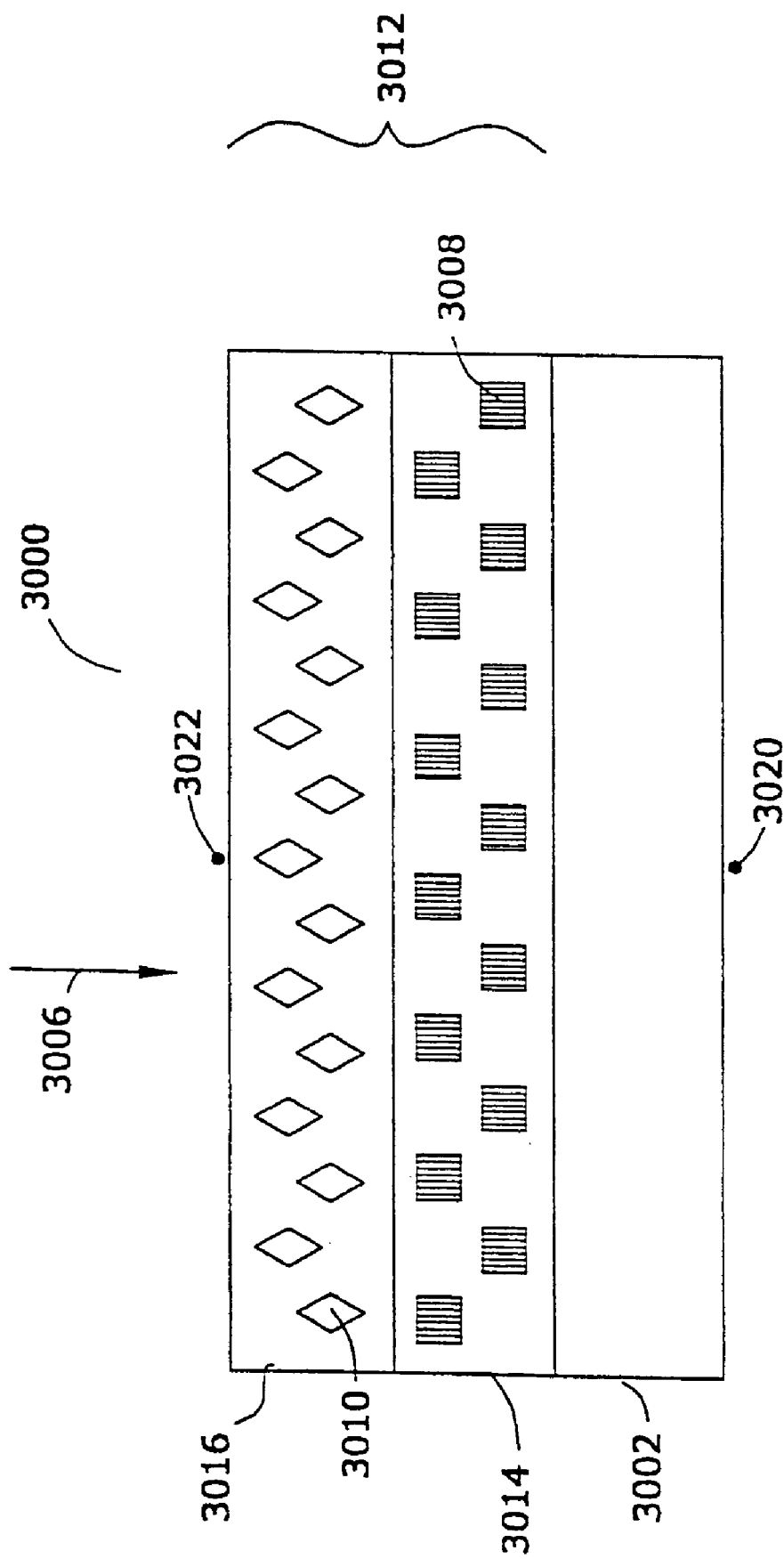

In the embodiment depicted in FIG. 30, by comparison, the shield 3012 is comprised of layers 3014 and 3016. The layer 3014 is comprised of at least about 50 weight percent of nanomagnetic material 3008 and, preferably, at least about 90 weight percent of such nanomagnetic material 3008. The layer 3016 is comprised of at least about 50 weight percent of electrical material 3010 and, preferably, at least about 90 weight percent of such electrical material 3010.

In the embodiment depicted in FIG. 30, the layer 3014 is disposed between the substrate 3002 and the layer 3016. In the embodiment depicted in FIG. 31, the layer 3016 is disposed between the substrate 3002 and the layer 3014.

Each of the layers 3014 and 3016 preferably has a thickness of from about 10 nanometers to about 5 microns.

In one embodiment, the shield 3012 has an electromagnetic shielding factor of at least about 0.5 and, more preferably, at least about 0.9. In one embodiment, the electromagnetic field strength at point 3020 is no greater than about 10 percent of the electromagnetic field strength at point 3022.

Figure 31:
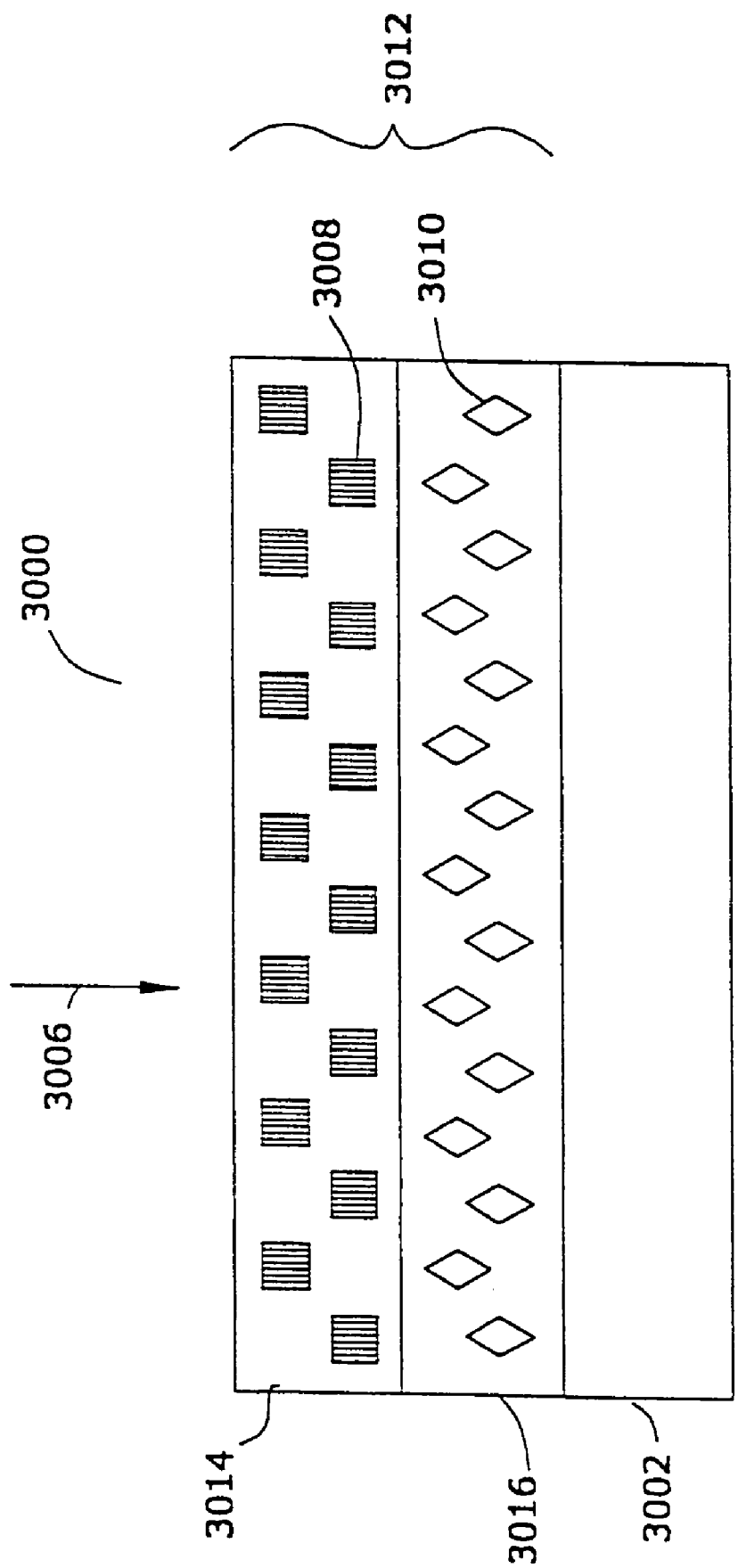

In one preferred embodiment, illustrated in FIG. 31, the nanomagnetic material 3008 and/or 3010 preferably has a mass density of at least about 0.01 grams per cubic centimeter, a saturation magnetization of from about 1 to about 36,000 Gauss, a coercive force of from about 0.01 to about 5000 Oersteds, a relative magnetic permeability of from about 1 to about 500,000, and an average particle size of less than about 100 nanometers.

Determination of the Heat Shielding Effect of the Magnetic Shield

Figure 32:
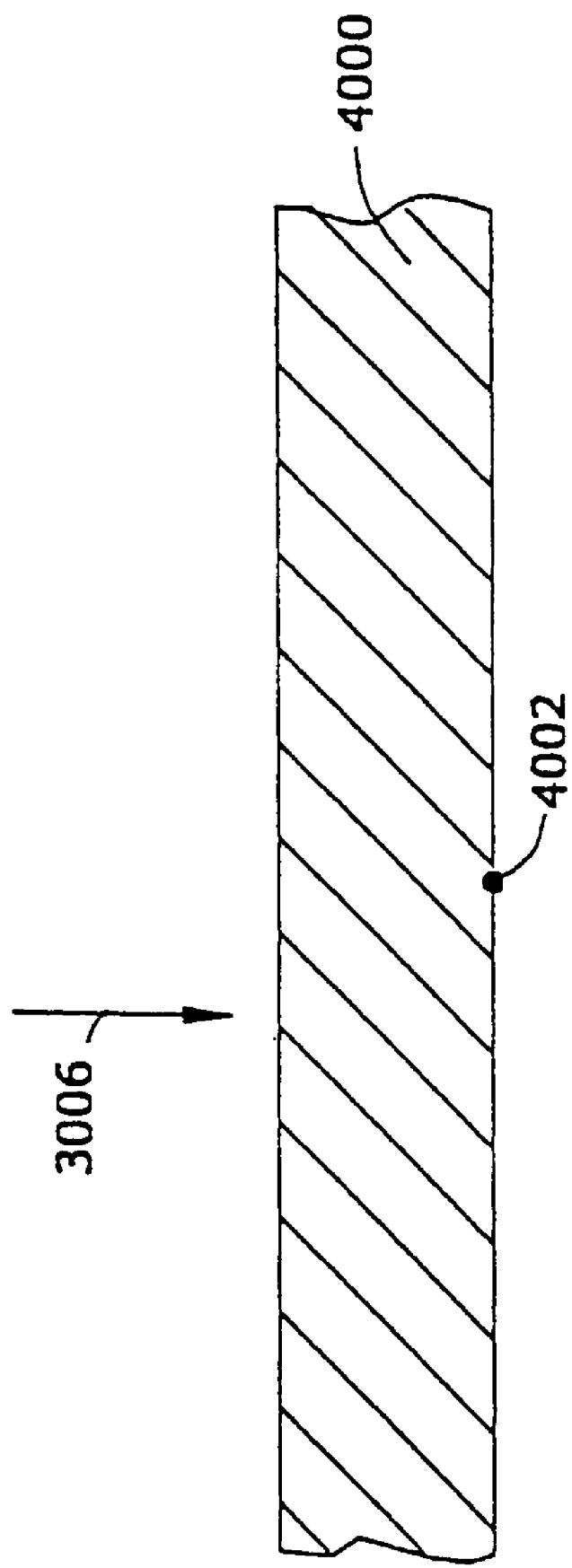
FIGS. 32-33 are schematic illustrations of means for determining the extent to which the temperature rises in a substrate when exposed to a strong magnetic field.

FIG. 32 is a schematic representation of a test which may be used to determine the extent to which the temperature of a conductor 4000 is raised by exposure to strong electromagnetic radiation 3006. In this test, the radiation 3006 is representative of the fields present during MRI procedures. As is known to those skilled in the art, such fields typically include a static field with a strength of from about 0.5 to about 2 Teslas, a radio frequency alternating magnetic field with a strength of from about 20 microTeslas to about 100 microTeslas, and a gradient magnetic field that has three components—x, y, and z, each of which has a field strength of from about 0.05 to 500 milliTeslas.

The test depicted in FIG. 32 is conducted in accordance with A.S.T.M. Standard Test F-2182-02, "Standard test method for measurement of radio-frequency induced heating near passive implant during magnetic resonance imaging." Referring again to FIG. 32, a temperature probe 4002 is used to measure the temperature of an unshielded conductor 4000 when subjected to the magnetic field 3006 in accordance with such A.S.T.M. F-2182-02.

Figure 33:
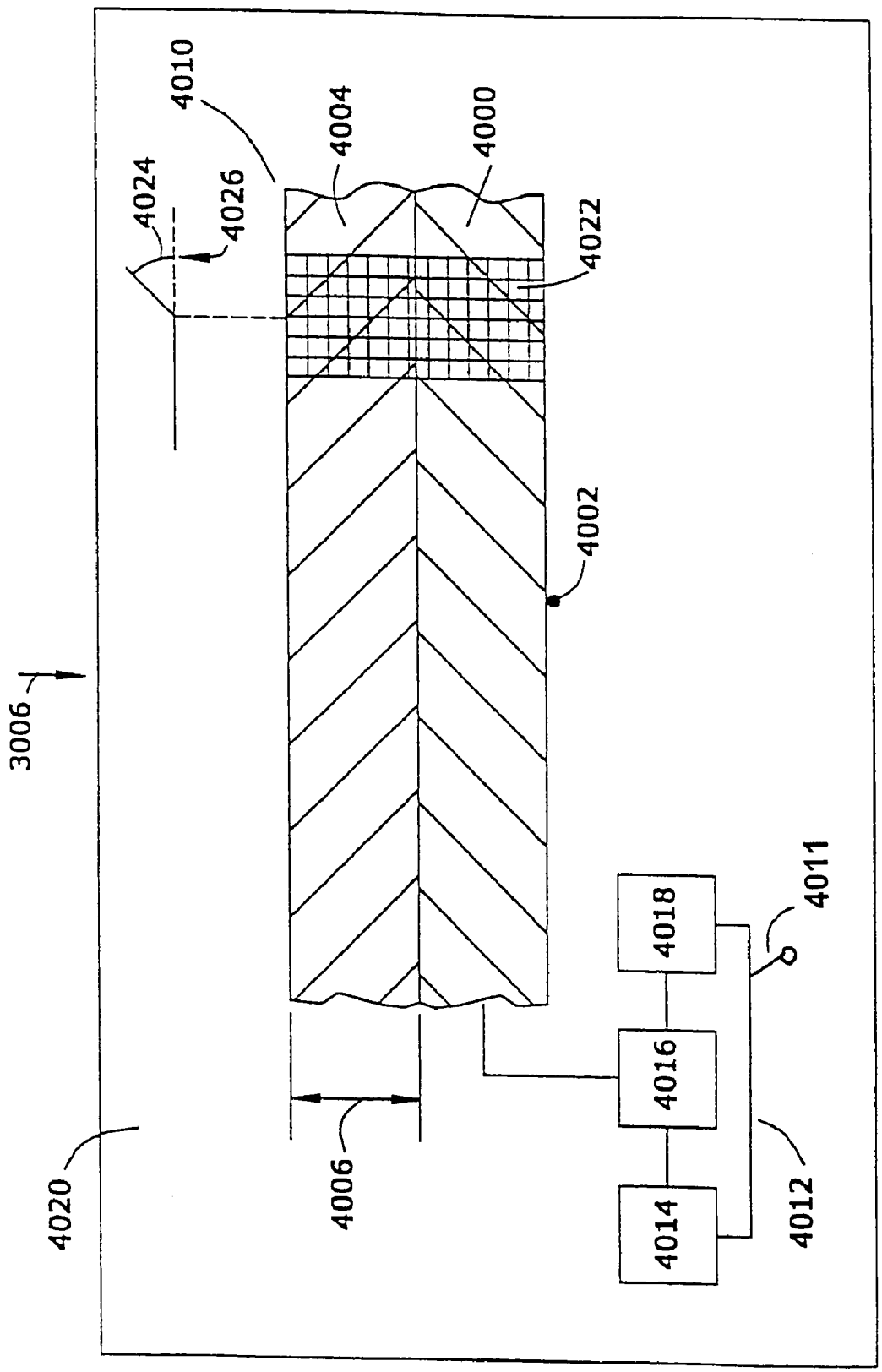

The same test is then performed upon a shielded conductor assembly 4010 that is comprised of the conductor 4000 and a magnetic shield 4004, as shown in FIG. 33.

The magnetic shield used may comprise nanomagnetic particles, as described hereinabove. Alternatively, or additionally, it may comprise other shielding material, such as, e.g., oriented nanotubes (see, e.g., U.S. Pat. No. 6,265,466). The entire disclosure of this United States patent is hereby incorporated by reference into this specification.

In the embodiment depicted in FIG. 33, the shield 4004 is in the form of a layer of shielding material with a thickness 4006 of from about 10 nanometers to about 1 millimeter. In one embodiment, the thickness 4006 is from about 10 nanometers to about 20 microns.

In one preferred embodiment, illustrated in FIG. 33, the shielded conductor 4010 is implantable device and is connected to a pacemaker assembly 4012 comprised of a power source 4014, a pulse generator 4016, and a controller 4018. The pacemaker assembly 4012 and its associated shielded conductor 4010 are preferably disposed within a living biological organism 4020.

Referring again to FIG. 33, and in the preferred embodiment depicted therein, it will be seen that shielded conductor assembly 4010 comprises a means 4011 for transmitting signals to and from the pacemaker 4012 and the biological organism 4020.

In one preferred embodiment, the conductor 4000 is flexible, that is, at least a portion 4022 of the conductor 4000 is capable of being flexed at an angle 4024 of least 15 degrees by the application of a force 4026 not to exceed about 1 dyne.

Figure 34:
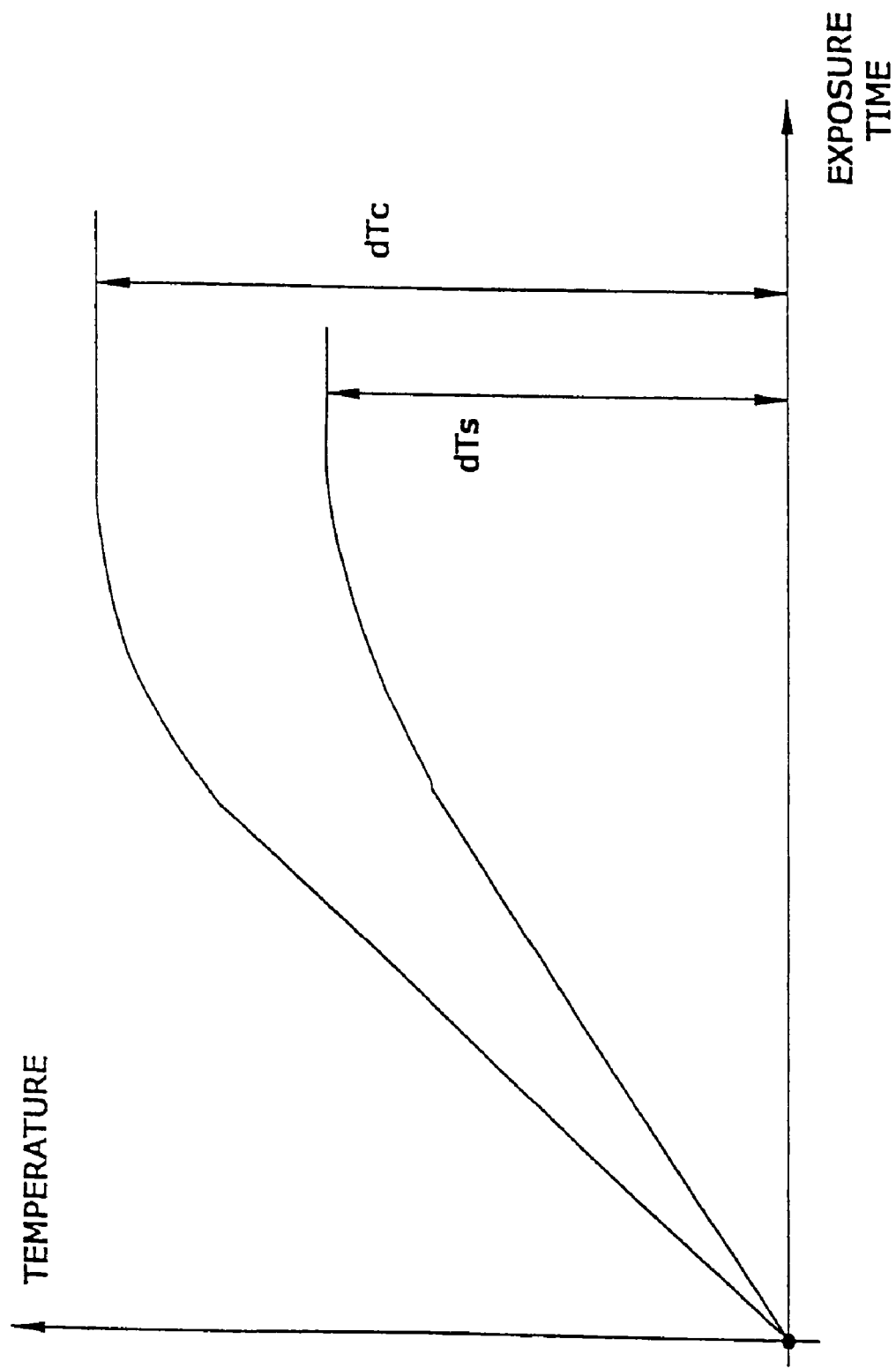
FIG. 34 is a graph showing the relationship of the temperature differentials in a shielded conductor and a non-conductor when each of them are exposed to the same magnetic field.

Referring again to FIG. 33, when the shielded assembly is tested in accordance with A.S.T.M. 2182-02, it will have a specified temperature increase, as is illustrated in FIG. 34.

As is shown in FIG. 34, the "dTs" is the change in temperature of the shielded assembly 4010 when tested in accordance with such A.S.T.M. test. The "dTc" is the change in temperature of the unshielded conductor 4000 using precisely the same test conditions but omitting the shield 4004. The ratio of dTs/dTc is the temperature increase ratio; and the temperature increase ratio is defined as the heat shielding factor.

It is preferred that the shielded conductor assembly 4010 have a heat shielding factor of less than about 0.2. In one embodiment, the shielded conductor assembly 4010 has a heat shielding factor of less than about least 0.3.

Figure 36:
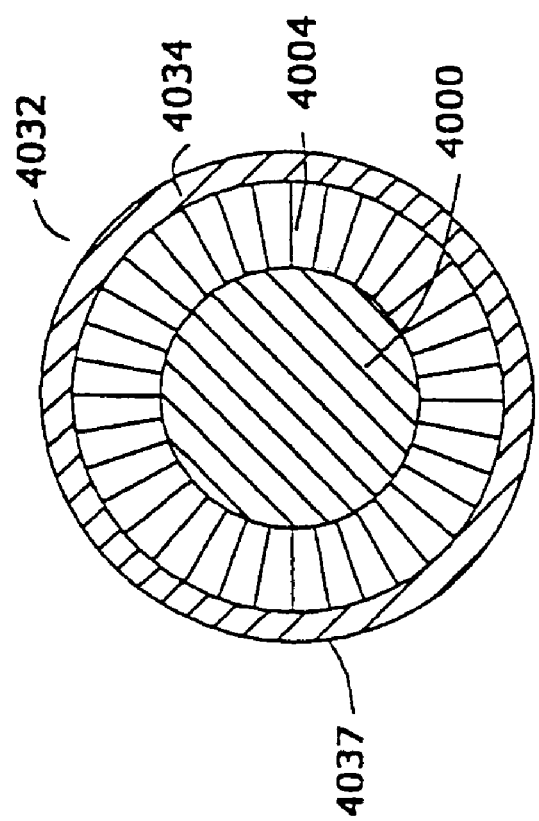
FIGS. 35-36 are schematics of preferred magnetic shield assemblies of the invention.
Figure 35:
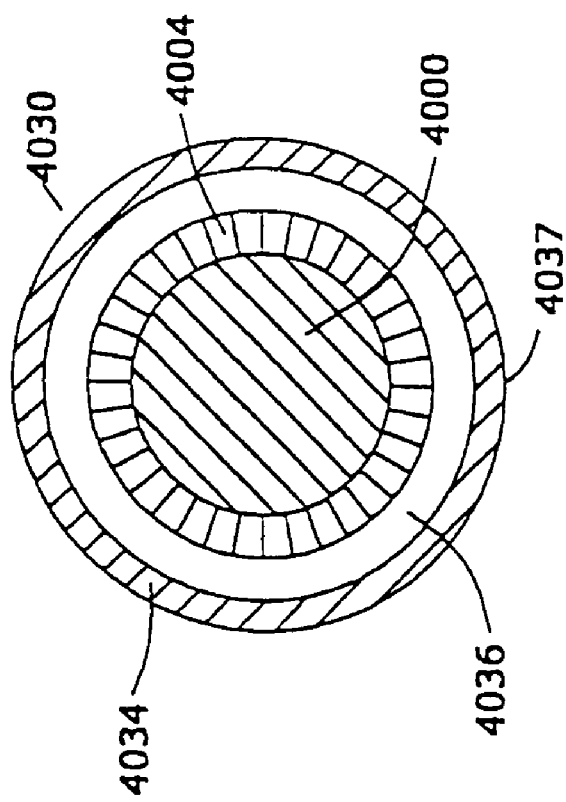

FIGS. 35 and 36 are sectional views of shielded conductor assembly 4030 and 4032. Each of these assemblies is comprised of a flexible conductor 4000, a layer 4004 of magnetic shielding material, and a sheath 4034.

The sheath 4034 preferably is comprised of antithrombogenic material. In one embodiment, the sheath 4034 preferably has a coefficient of friction of less than about 0.1.

Antithrombogenic compositions and structures have been well known to those skilled in the art for many years. As is disclosed, e.g., in U.S. Pat. No. 5,783,570, the entire disclosure of which is hereby incorporated by reference into this specification, "Artificial materials superior in processability, elasticity and flexibility have been widely used as medical materials in recent years. It is expected that they will be increasingly used in a wider area as artificial organs such as artificial kidney, artificial lung, extracorporeal circulation devices and artificial blood vessels, as well as disposable products such as syringes, blood bags, cardiac catheters and the like. These medical materials are required to have, in addition to sufficient mechanical strength and durability, biological safety which particularly means the absence of blood coagulation upon contact with blood, i.e., antithrombogenicity."

"Conventionally employed methods for imparting antithrombogenicity to medical materials are generally classified into three groups of (1) immobilizing a mucopolysaccharide (e.g., heparin) or a plasminogen activator (e.g., urokinase) on the surface of a material, (2) modifying the surface of a material so that it carries negative charge or hydrophilicity, and (3) inactivating the surface of a material. Of these, the method of (1) (hereinafter to be referred to briefly as surface heparin method) is further subdivided into the methods of (A) blending of a polymer and an organic solvent-soluble heparin, (B) coating of the material surface with an organic solvent-soluble heparin, (C) ionic bonding of heparin to a cationic group in the material, and (D) covalent bonding of a material and heparin."

"Of the above methods, the methods (2) and (3) are capable of affording a stable antithrombogenicity during a long-term contact with body fluids, since protein adsorbs onto the surface of a material to form a biomembrane-like surface. At the initial stage when the material has been introduced into the body (blood contact site) and when various coagulation factors etc. in the body have been activated, however, it is difficult to achieve sufficient antithrombogenicity without an anticoagulant therapy such as heparin administration."

Other antithrombogenic methods and compositions are also well known. Thus, by way of further illustration, United States published patent application 2001/0016611 discloses an antithrombogenic composition comprising an ionic complex of ammonium salts and heparin or a heparin derivative, said ammonium salts each comprising four aliphatic alkyl groups bonded thereto, wherein an ammonium salt comprising four aliphatic alkyl groups having not less than 22 and not more than 26 carbon atoms in total is contained in an amount of not less than 5% and not more than 80% of the total ammonium salt by weight. The entire disclosure of this published patent application is hereby incorporated by reference into this specification.

Thus, e.g., U.S. Pat. No. 5,783,570 discloses an organic solvent-soluble mucopolysaccharide consisting of an ionic complex of at least one mucopolysaccharide (preferably heparin or heparin derivative) and a quaternary phosphonium, an antibacterial antithrombogenic composition comprising said organic solvent-soluble mucopolysaccharide and an antibacterial agent (preferably an inorganic antibacterial agent such as silver zeolite), and to a medical material comprising said organic solvent soluble mucopolysaccharide. The organic solvent-soluble mucopolysaccharide, and the antibacterial antithrombogenic composition and medical material containing same are said to easily impart antithrombogenicity and antibacterial property to a polymer to be a base material, which properties are maintained not only immediately after preparation of the material but also after long-term elution. The entire disclosure of this United States patent is hereby incorporated by reference into this specification.

By way of further illustration, U.S. Pat. No. 5,049,393 discloses anti-thrombogenic compositions, methods for their production and products made therefrom. The anti-thrombogenic compositions comprise a powderized anti-thrombogenic material homogeneously present in a solidifiable matrix material. The anti-thrombogenic material is preferably carbon and more preferably graphite particles. The matrix material is a silicon polymer, a urethane polymer or an acrylic polymer. The entire disclosure of this United States patent is hereby incorporated by reference into this specification.

By way of yet further illustration, U.S. Pat. No. 5,013,717 discloses a leach resistant composition that includes a quaternary ammonium complex of heparin and a silicone. A method for applying a coating of the composition to a surface of a medical article is also disclosed in the patent. Medical articles having surfaces which are both lubricious and antithrombogenic, are produced in accordance with the method of the patent. The entire disclosure of this United States patent is hereby incorporated by reference into this specification.

Referring again to FIG. 35, and in the preferred embodiment depicted therein, the sheath 4034 is non contiguous with the layer 4004; in this embodiment, another material 4036 (such as, e.g., air) is present. In FIG. 36, by comparison, the sheath 4034 is contiguous with the layer 4004.

In both of the embodiments depicted in FIGS. 35 and 36, the conductor 4000 preferably has a resistivity at 20 degrees Centigrade of from about 1 to about 100 micro ohm-centimeters.

In one embodiment, not shown, the sheath 4034 is omitted and the shield 4004 itself is comprised of and/or acts as an antithrombogenic composition. In one aspect of this embodiment, the outer surface 4037 of sheath 4034 is hydrophobic. In another aspect of this embodiment, the outer surface 4037 of the sheath is hydrophilic. Similarly, in the embodiments depicted in FIGS. 35 and 36, the outer surface 4037 of the sheath 4034 can be either hydrophobic or hydrophilic.

In this embodiment, the conductor assembly is comprised of a magnetic shield disposed above said flexible conductor, wherein said magnetic shield is comprised of an antithrombogenic composition, wherein said magnetic shield is comprised of a layer of magnetic shielding material, and wherein said layer of magnetic shielding material, when exposed to a magnetic field with a intensity of at least about 30 microTesla, has a magnetic shielding factor of at least about 0.5. In one embodiment, the conductor assembly has a heat shielding factor of at least about 0.2

A Process for Preparation of an Iron-containing Thin Film

In one preferred embodiment of the invention, a sputtering technique is used to prepare an AlFe thin film as well as comparable thin films containing other atomic moieties, such as, e.g., elemental nitrogen, and elemental oxygen. Conventional sputtering techniques may be used to prepare such films by sputtering. See, for example, R. Herrmann and G. Brauer, "D.C.—and R. F. Magnetron Sputtering," in the "Handbook of Optical Properties: Volume I—Thin Films for Optical Coatings," edited by R. E. Hummel and K. H. Guenther (CRC Press, Boca Raton, Fla., 1955). Reference also may be had, e.g., to M. Allendorf, "Report of Coatings on Glass Technology Roadmap Workshop," Jan. 18-19, 2000, Livermore, Calif.; and also to U.S. Pat. No. 6,342,134, "Method for producing piezoelectric films with rotating magnetron sputtering system." The entire disclosure of each of these prior art documents is hereby incorporated by reference into this specification.

Although the sputtering technique is preferred, the plasma technique described elsewhere in this specification also may be used.

One may utilize conventional sputtering devices in this process. By way of illustration and not limitation, a typical sputtering system is described in U.S. Pat. No. 5,178,739, the entire disclosure of which is hereby incorporated by reference into this specification. As is disclosed in this patent, " . . . a sputter system 10 includes a vacuum chamber 20, which contains a circular end sputter target 12, a hollow, cylindrical, thin, cathode magnetron target 14, a RF coil 16 and a chuck 18, which holds a semiconductor substrate 19. The atmosphere inside the vacuum chamber 20 is controlled through channel 22 by a pump (not shown). The vacuum chamber 20 is cylindrical and has a series of permanent, magnets 24 positioned around the chamber and in close proximity therewith to create a multipole field configuration near the interior surface 15 of target 12. Magnets 26, 28 are placed above end sputter target 12 to also create a multipole field in proximity to target 12. A singular magnet 26 is placed above the center of target 12 with a plurality of other magnets 28 disposed in a circular formation around magnet 26. For convenience, only two magnets 24 and 28 are shown. The configuration of target 12 with magnets 26, 28 comprises a magnetron sputter source 29 known in the prior art, such as the Torus-10E system manufactured by K. Lesker, Inc. A sputter power supply 30 (DC or RF) is connected by a line 32 to the sputter target 12. A RF supply 34 provides power to RF coil 16 by a line 36 and through a matching network 37. Variable impedance 38 is connected in series with the cold end 17 of coil 16. A second sputter power supply 39 is connected by a line 40 to cylindrical sputter target 14. A bias power supply 42 (DC or RF) is connected by a line 44 to chuck 18 in order to provide electrical bias to substrate 19 placed thereon, in a manner well known in the prior art."

By way of yet further illustration, other conventional sputtering systems and processes are described in U.S. Pat. No. 5,569,506 (a modified Kurt Lesker sputtering system); U.S. Pat. No. 5,824,761 (a Lesker Torus 10 sputter cathode); U.S. Pat. Nos. 5,768,123; 5,645,910; 6,046,398 (sputter deposition with a Kurt J. Lesker Co. Torus 2 sputter gun); U.S. Pat. Nos. 5,736,488; 5,567,673; 6,454,910; and the like. The entire disclosure of each of these United States patents is hereby incorporated by reference into this specification.

By way of yet further illustration, one may use the techniques described in a paper by Xingwu Wang et al. entitled "Technique Devised for Sputtering AlN Thin Films," published in "the Glass Researcher," Volume 11, No. 2 (Dec. 12, 2002). The entire disclosure of this publication is hereby incorporated by reference into this specification.

In one preferred embodiment, a magnetron sputtering technique is utilized, with a Lesker Super System III system. The vacuum chamber of this system is cylindrical, with a diameter of approximately one meter and a height of approximately 0.6 meters. The base pressure used is from about 0.001 to 0.0001 Pascals. In one aspect of this process, the target is a metallic FeAl disk, with a diameter of approximately 0.1 meter. The molar ratio between iron and aluminum used in this aspect is approximately 70/30. Thus, the starting composition in this aspect is almost non-magnetic. See, e.g., page 83 (FIG. 3.1aii) of R. S. Tebble et al.'s "Magnetic Materials" (Wiley-Interscience, New York, N.Y., 1969); this Figure discloses that a bulk composition containing iron and aluminum with at least 30 mole percent of aluminum (by total moles of iron and aluminum) is substantially non-magnetic.

In this aspect, to fabricate FeAl films, a DC power source is utilized, with a power level of from about 150 to about 550 watts (Advanced Energy Company of Colorado, model MDX Magnetron Drive). The sputtering gas used in this aspect is argon, with a flow rate of from about 0.0012 to about 0.0018 standard cubic meters per second. To fabricate FeAlN films in this aspect, in addition to the DC source, a pulse-forming device is utilized, with a frequency of from about 50 to about 250 MHz (Advanced Energy Company, model Sparc-Ie V). One may fabricate FeAlO films in a similar manner but using oxygen rather than nitrogen.

In this aspect, a typical argon flow rate is from about (0.9 to about 1.5)$\times 10^{-3}$ standard cubic meters per second; a typical nitrogen flow rate is from about (0.9 to about 1.8)$\times 10^{-3}$ standard cubic meters per second; and a typical oxygen flow rate is from about. (0.5 to about 2)$\times 10^{-3}$ standard cubic meters per second. During fabrication, the pressure typically is maintained at from about 0.2 to about 0.4 Pascals. Such a pressure range is found to be suitable for nanomagnetic materials fabrications.

In this aspect, the substrate used may be either flat or curved. A typical flat substrate is a silicon wafer with or without a thermally grown silicon dioxide layer, and its diameter is preferably from about 0.1 to about 0.15 meters. A typical curved substrate is an aluminum rod or a stainless steel wire, with a length of from about 0.10 to about 0.56 meters and a diameter of from (about 0.8 to about 3.0)$\times 10^{-3}$ meters The distance between the substrate and the target is preferably from about 0.05 to about 0.26 meters.

In this aspect, in order to deposit a film on a wafer, the wafer is fixed on a substrate holder. The substrate may or may not be rotated during deposition. In one embodiment, to deposit a film on a rod or wire, the rod or wire is rotated at a rotational speed of from about 0.01 to about 0.1 revolutions per second, and it is moved slowly back and forth along its symmetrical axis with a maximum speed of about 0.01 meters per second.

In this aspect, to achieve a film deposition rate on the flat wafer of $5\times10^{-10}$ meters per second, the power required for the FeAl film is 200 watts, and the power required for the FeAlN film is 500 watts. The resistivity of the FeAlN film is approximately one order of magnitude larger than that of the metallic FeAl film. Similarly, the resistivity of the FeAlO film is about one order of magnitude larger than that of the metallic FeAl film.

Iron containing magnetic materials, such as FeAl, FeAlN and FeAlO, have been fabricated by various techniques. The magnetic properties of those materials vary with stoichiometric ratios, particle sizes, and fabrication conditions; see, e.g., R. S. Tebble and D. J. Craik, "Magnetic Materials", pp. 81-88, Wiley-Interscience, New York, 1969. As is disclosed in this reference, when the iron molar ratio in bulk FeAl materials is less than 70 percent or so, the materials will no longer exhibit magnetic properties.

However, it has been discovered that, in contrast to bulk materials, a thin film material often exhibits different properties due to the constraint provided by the substrate.

Nanomagnetic Compositions Comprised of Moieties A, B, and C

Figure 37:
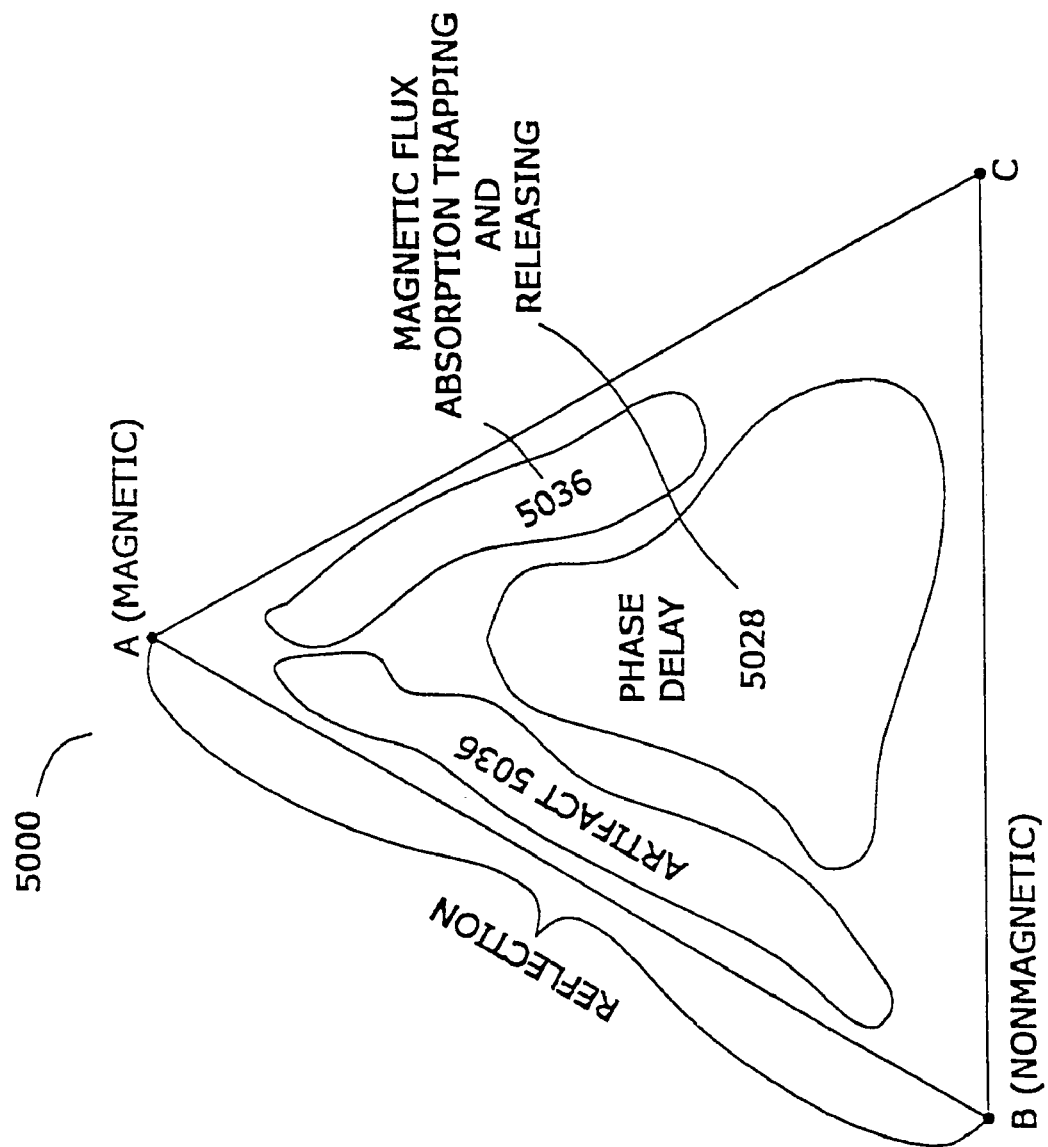
FIG. 37 is a phase diagram of a preferred nanomagnetic material.

The aforementioned process described in the preceding section of this specification may be adapted to produce other, comparable thin films, as is illustrated in FIG. 37.

Referring to FIG. 37, and in the preferred embodiment depicted therein, a phase diagram 5000 is presented. As is illustrated by this phase diagram 5000, the nanomagnetic material used in the composition of this invention preferably is comprised of one or more of moieties A, B, and C.

The moiety A depicted in phase diagram 5000 is comprised of a magnetic element selected from the group consisting of a transition series metal, a rare earth series metal, or actinide metal, a mixture thereof, and/or an alloy thereof.

As is known to those skilled in the art, the transition series metals include chromium, manganese, iron, cobalt, nickel. One may use alloys or iron, cobalt and nickel such as, e.g., iron-aluminum, iron-carbon, iron-chromium, iron-cobalt, iron-nickel, iron nitride ($Fe_3N$), iron phosphide, iron-silicon, iron-vanadium, nickel-cobalt, nickel-copper, and the like. One may use alloys of manganese such as, e.g., manganese-aluminum, manganese-bismuth, MnAs, MnSb, MnTe, manganese-copper, manganese-gold, manganese-nickel, manganese-sulfur and related compounds, manganese-antimony, manganese-tin, manganese-zinc, Heusler alloy, and the like. One may use compounds and alloys of the iron group, including oxides of the iron group, halides of the iron group, borides of the transition elements, sulfides of the iron group, platinum and palladium with the iron group, chromium compounds, and the like.

One may use a rare earth and/or actinide metal such as, e.g., Ce, Pr, Nd, Pm, Sm, Eu, Gd, Tb, Dy, Ho, Er, Tm, Yb, Lu, La, mixtures thereof, and alloys thereof. One may also use one or more of the actinides such as, e.g., Th, Pa, U, Np, Pu, Am, Cm, Bk, Cf, Es, Fm, Md, No, Lr, Ac, and the like.

These moieties, compounds thereof, and alloys thereof are well known and are described, e.g., in the aforementioned text of R. S. Tebble et al. entitled "Magnetic Materials."

In one preferred embodiment, moiety A is selected from the group consisting of iron, nickel, cobalt, alloys thereof, and mixtures thereof. In this embodiment, the moiety A is magnetic, i.e., it has a relative magnetic permeability of from about 1 to about 500,000. As is known to those skilled in the art, relative magnetic permeability is a factor, characteristic of a material, that is proportional to the magnetic induction produced in a material divided by the magnetic field strength; it is a tensor when these quantities are not parallel. See, e.g., page 4-128 of E. U. Condon et al.'s "Handbook of Physics" (McGraw-Hill Book Company, Inc., New York, N.Y., 1958).

The moiety A also preferably has a saturation magnetization of from about 1 to about 36,000 Gauss, and a coercive force of from about 0.01 to about 5,000 Oersteds.

The moiety A may be present in the nanomagnetic material either in its elemental form, as an alloy, in a solid solution, or as a compound.

It is preferred at least about 1 mole percent of moiety A be present in the nanomagnetic material (by total moles of A, B, and C), and it is more preferred that at least 10 mole percent of such moiety A be present in the nanomagnetic material (by total moles of A, B, and C). In one embodiment, at least 60 mole percent of such moiety A is present in the nanomagnetic material, (by total moles of A, B, and C.)

In addition to moiety A, it is preferred to have moiety B be present in the nanomagnetic material. In this embodiment, moieties A and B are admixed with each other. The mixture may be a physical mixture, it may be a solid solution, it may be comprised of an alloy of the A/B moieties, etc.

In one embodiment, the magnetic material A is dispersed within nonmagnetic material B. This embodiment is depicted schematically in FIG. 38.

Figure 38:
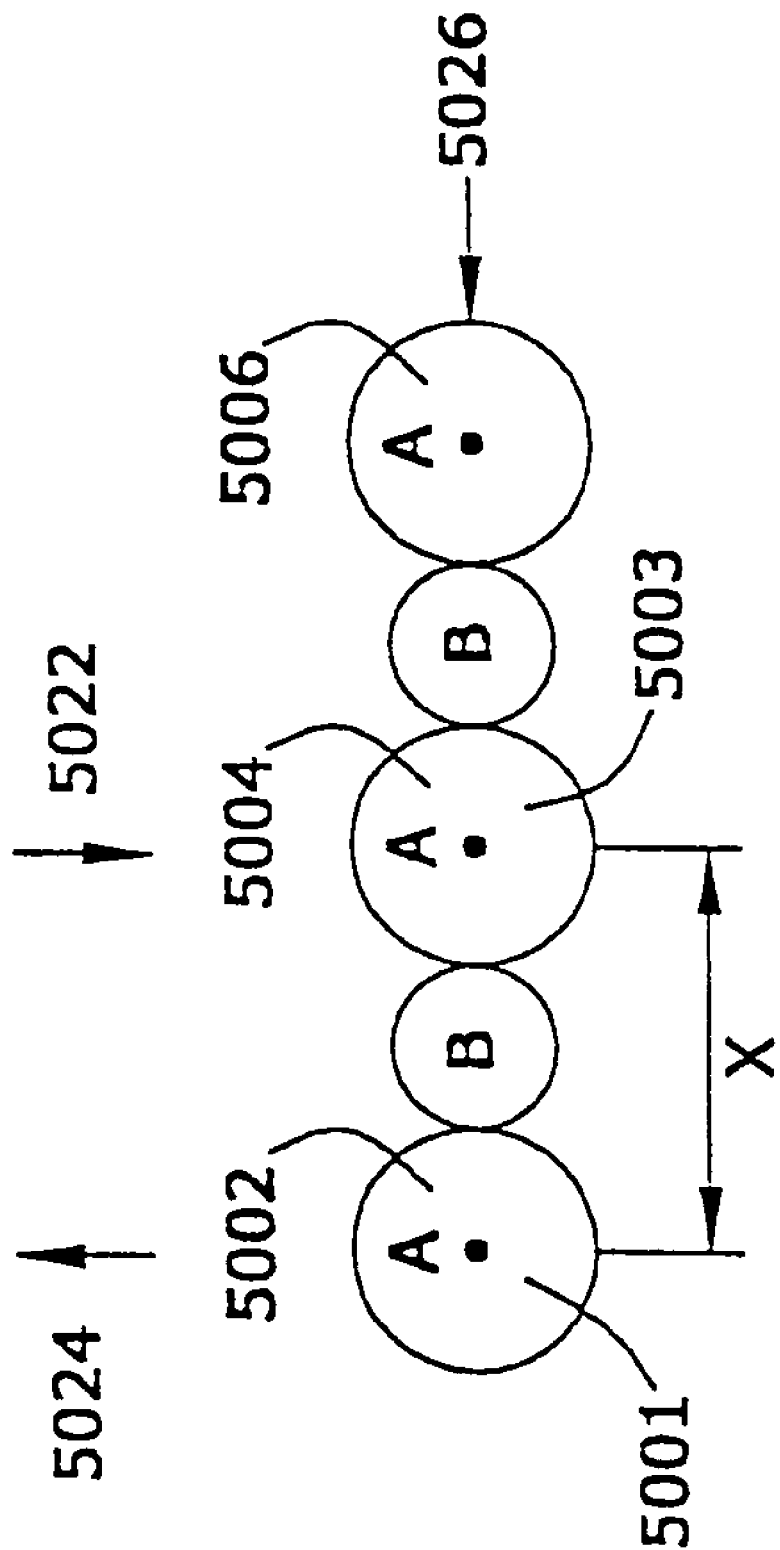
FIG. 38 is a schematic of the spacing between components of the nanomagnetic material of this invention.

Referring to FIG. 38, and in the preferred embodiment depicted therein, it will be seen that A moieties 5002, 5004, and 5006 are separated from each other either at the atomic level and/or at the nanometer level. The A moieties may be, e.g., A atoms, clusters of A atoms, A compounds, A solid solutions, etc; regardless of the form of the A moiety, it has the magnetic properties described hereinabove.

In the embodiment depicted in FIG. 38, each A moiety produces an independent magnetic moment. The coherence length (L) between adjacent A moieties is, on average, from about 0.1 to about 100 nanometers and, more preferably, from about 1 to about 50 nanometers.

Thus, referring again to FIG. 38, the normalized magnetic interaction between adjacent A moieties 5002 and 5004, and also between 5004 and 5006, is preferably described by the formula $M=\exp(-x/L)$, wherein M is the normalized magnetic interaction, exp is the base of the natural logarithm (and is approximately equal to 2.71828), x is the distance between adjacent A moieties, and L is the coherence length.

In one embodiment, and referring again to FIG. 38, x is preferably measured from the center 5001 of A moiety 5002 to the center 5003 of A moiety 5004; and x is preferably equal to from about $0.00001\times L$ to about $100\times L$.

In one embodiment, the ratio of x/L is at least 0.5 and, preferably, at least 1.5.

Referring again to FIG. 37, the nanomagnetic material may be comprised of 100 percent of moiety A, provided that such moiety A has the required normalized magnetic interaction (M). Alternatively, the nanomagnetic material may be comprised of both moiety A and moiety B.

When moiety B is present in the nanomagnetic material, in whatever form or forms it is present, it is preferred that it be present at a mole ratio (by total moles of A and B) of from about 1 to about 99 percent and, preferably, from about 10 to about 90 percent.

The B moiety, in whatever form it is present, is nonmagnetic, i.e., it has a relative magnetic permeability of 1.0; without wishing to be bound to any particular theory, applicants believe that the B moiety acts as buffer between adjacent A moieties. One may use, e.g., such elements as silicon, aluminum, boron, platinum, tantalum, palladium, yttrium, zirconium, titanium, calcium, beryllium, barium, silver, gold, indium, lead, tin, antimony, germanium, gallium, tungsten, bismuth, strontium, magnesium, zinc, and the like.

In one embodiment, and without wishing to be bound to any particular theory, it is believed that B moiety provides plasticity to the nanomagnetic material that it would not have but for the presence of B. It is preferred that the bending radius of a substrate coated with both A and B moieties be at least 110 percent as great as the bending radius of a substrate coated with only the A moiety.

The use of the B material allows one to produce a coated substrate with a springback angle of less than about 45 degrees. As is known to those skilled in the art, all materials have a finite modulus of elasticity; thus, plastic deformations followed by some elastic recovery when the load is removed. In bending, this recovery is called springback. See, e.g., page 462 of S. Kalparjian's "Manufacturing Engineering and Technology," Third Edition (Addison Wesley Publishing Company, New York, N.Y., 1995).

Figure 39:
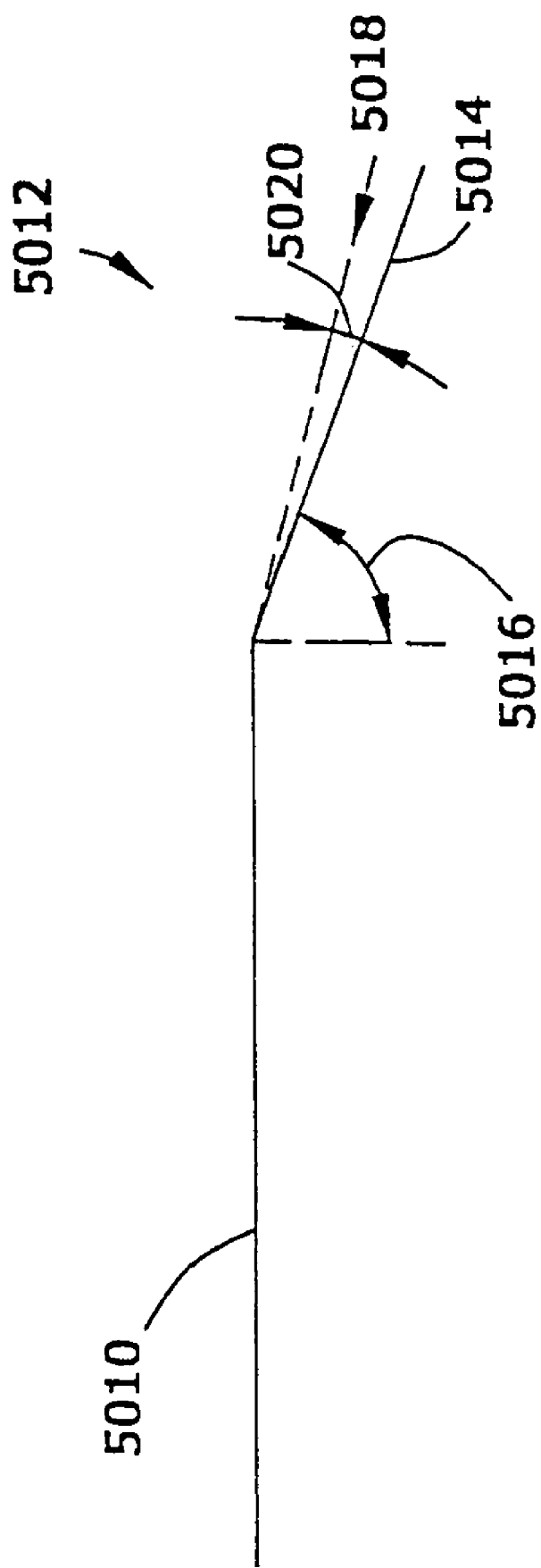
FIG. 39 illustrates the springback properties of one coated substrate of the invention.

FIG. 39 illustrates how springback is determined in accordance with this invention. Referring to FIG. 39, a coated substrate 5010 is subjected to a force in the direction of arrow 5012 that bends portion 5014 of the substrate to an angle 5016 of 45 degrees, preferably in a period of less than about 10 seconds. Thereafter, when the force is released, the bent portion 5014 springs back to position 5018. The springback angle 5020 is preferably less than 45 degrees and, preferably, is less than about 10 degrees.

Referring again to FIG. 38, when an electromagnetic field 5022 is incident upon the nanomagnetic material 5026 comprised of A and B (see FIG. 38), such a field will be reflected to some degree depending upon the ratio of moiety A and moiety B. In one embodiment, it is preferred that at least 1 percent of such field is reflected in the direction of arrow 5024. In another embodiment, it is preferred that at least about 10 percent of such field is reflected. In yet another embodiment, at least about 90 percent of such field is reflected. Without wishing to be bound to any particular theory, applicants believe that the degree of reflection depends upon the concentration of A in the A/B mixture.

M, the normalized magnetic interaction, preferably ranges from about $3 \times 10^{-44}$ to about 1.0. In one preferred embodiment, M is from about 0.01 to 0.99. In another preferred embodiment, M is from about 0.1 to about 0.9.

Referring again to FIG. 37, and in one embodiment, the nanomagnetic material is comprised of moiety A, moiety C, and optionally moiety B. The moiety C is preferably selected from the group consisting of elemental oxygen, elemental nitrogen, elemental carbon, elemental fluorine, elemental chlorine, elemental hydrogen, elemental helium, elemental neon, elemental argon, elemental krypton, elemental xenon, and the like.

It is preferred, when the C moiety is present, that it be present in a concentration of from about 1 to about 90 mole percent, based upon the total number of moles of the A moiety and/or the B moiety and C moiety in the composition.

Referring again to FIG. 37, and in the embodiment depicted, the area 5028 produces a composition which optimizes the degree to which magnetic flux are initially trapped and/or thereafter released by the composition when a magnetic field is withdrawing from the composition.

Without wishing to be bound to any particular theory, applicants believe that, when a composition as described by area 5028 is subjected to an alternating magnetic field, at least a portion of the magnetic field is trapped by the composition when the field is strong, and then this portion tends to be released when the field lessens in intensity. This theory is illustrated in FIG. 40.

Figure 40:
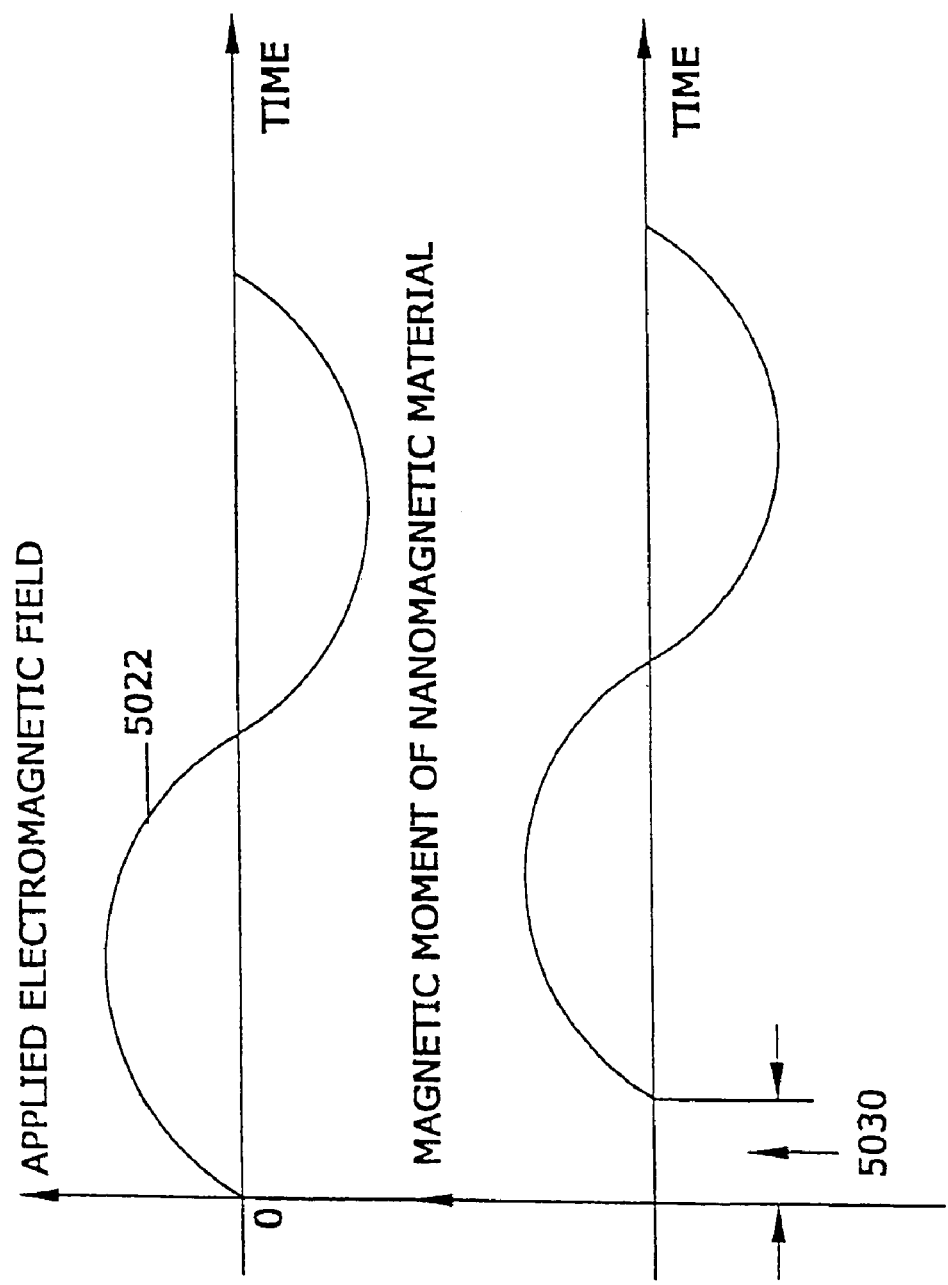
FIGS. 40, 41, and 42 are graphs illustrating the relationship of the applied magnetic field to the measured magnetic field when the coated substrate of the invention is used as a shield.

Referring to FIG. 40, at time zero, the magnetic field 5022 applied to the nanomagnetic material starts to increase, in a typical sine wave fashion. After a specified period of time 5030, a magnetic moment is created within the nanomagnetic material; but, because of the time delay, there is a phase shift.

Figure 41:
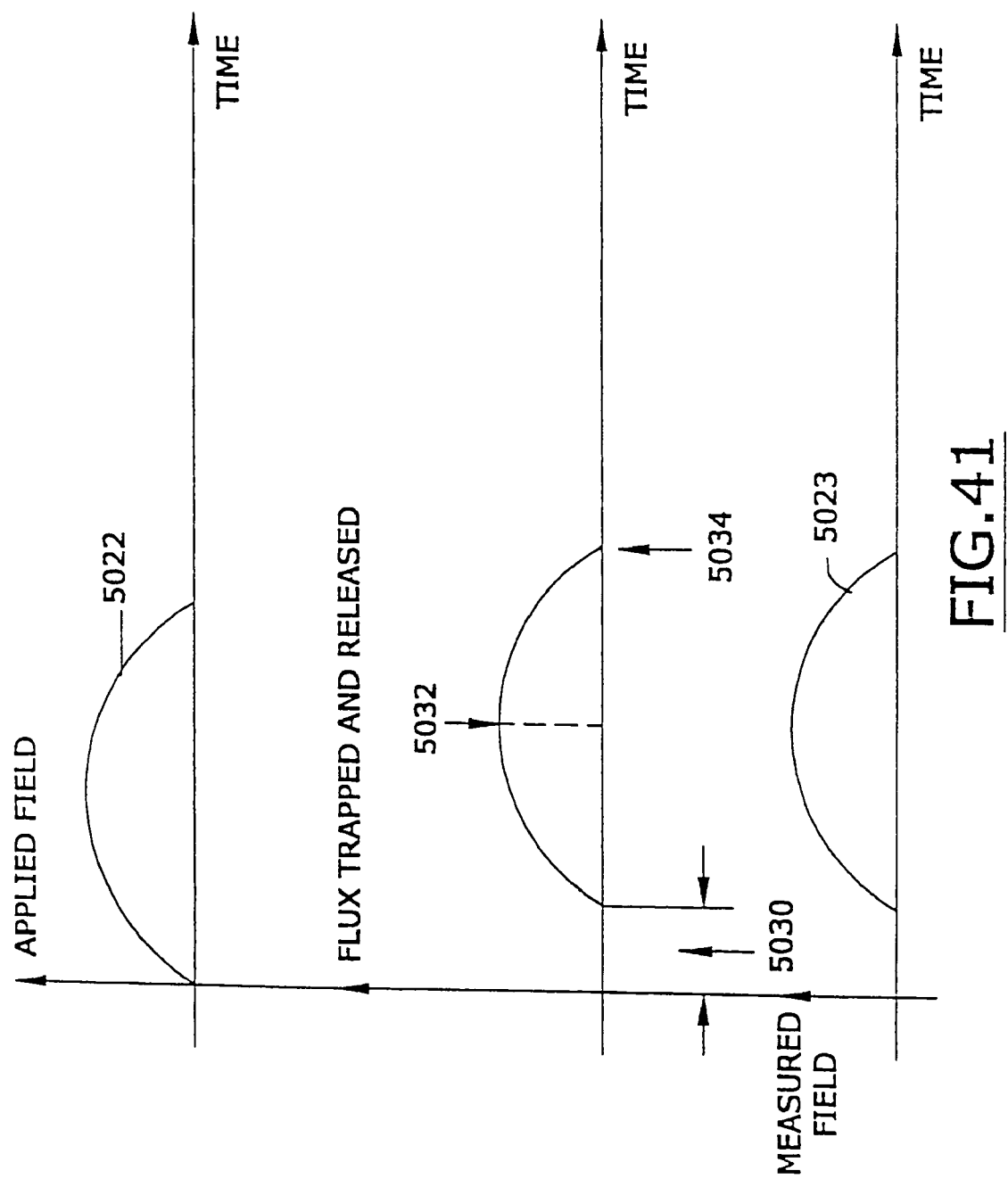

FIG. 41 illustrates how a portion of the magnetic field 5022 is trapped within the nanomagnetic material and thereafter released. Referring to FIG. 41, it will be seen that the applied field 5022 is trapped after a time delay 5030 within the nanomagnetic material and thereafter, at point 5032, starts to release; at point 5034, the trapped flux is almost completely released.

The time delay 5030 (see FIGS. 40/41) will vary with the composition of the nanomagnetic material. By maximizing the amount of trapping, and by minimizing the amount of reflection and absorption, one may minimize the magnetic artifacts caused by the nanomagnetic shield.

Thus, one may optimize the A/B/C composition to preferably be within the area 5028 (see FIG. 37). In general, the A/B/C composition has molar ratios such that the ratio of A/(A and C) is from about 1 to about 99 mole percent and, preferably, from about 10 to about 90 mole percent. In one preferred embodiment, such ratio is from about 40 to about 60 molar percent.

The molar ratio of A/(A and B and C) generally is from about 1 to about 99 mole percent and, preferably, from about 10 to about 90 molar percent. In one embodiment, such molar ratio is from about 30 to about 60 molar percent.

The molar ratio of B/(A plus B plus C) generally is from about 1 to about 99 mole percent and, preferably, from about 10 to about 40 mole percent.

The molar ratio of C/(A plus B plus C) generally is from about 1 to about 99 mole percent and, preferably, from about 10 to about 50 mole percent.

In one embodiment, the composition of the nanomagnetic material is chosen so that the applied electromagnetic field 5022 is absorbed by the nanomagnetic material by less than about 1 percent; thus, in this embodiment, the applied magnetic field 5022 is substantially restored by correcting the time delay 5030. Referring to FIG. 41, and to the embodiment depicted, the applied magnetic field 5022 and the measured magnetic field 5023 are substantially identical, with the exception of their phases.

Figure 42:
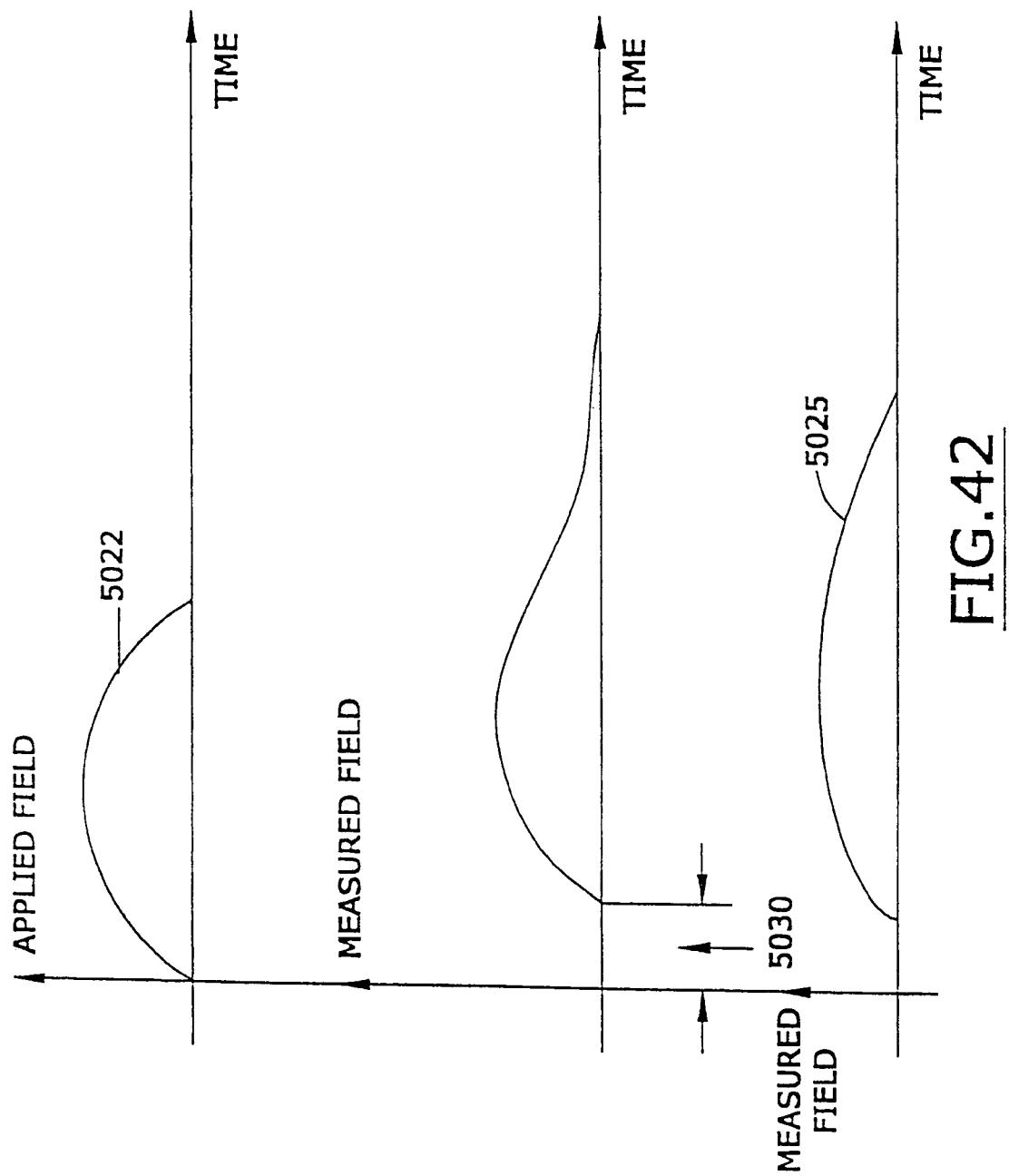

In another embodiment, illustrated in FIG. 42, the measured field 5025 is substantially different from the applied field 5022. In this embodiment, an artifact will be detected by the magnetic field measuring device (not shown). The presence of such an artifact, and its intensity, may be used to detect and quantify the exact location of the coated substrate. In this embodiment, one preferably would use an area outside of area 5028 (see FIG. 37), such as, e.g., area 5036.

In another embodiment, also illustrated in FIG. 42, the measured field 5025 has less intensity than the applied field 5022. One may increase the amount of absorption of the nanomagnetic material to produce a measured field like measured field 5025 by utilizing the area 5036 of FIG. 37.

By utilizing nanomagnetic material that absorbs the electromagnetic field, one may selectively direct energy to various cells that are to be treated. Thus, e.g., cancer cells can be injected with the nanomagnetic material and then destroyed by the application of externally applied electromagnetic fields. Because of the nano size of applicants' materials, they can readily and preferentially be directed to the malignant cells to be treated within a living organism. In this embodiment, the nanomagnetic material preferably has a particle size of from about 5 to about 10 nanometers and, thus, can be used in a manner similar to a tracer.

In one embodiment, the nanomagnetic material is injected into a patient's bloodstream. In another embodiment, the nanomagnetic material is inhaled by a patient. In another embodiment, it is digested by a patient. In another embodiment, it is implanted through conventional means. In each of these embodiments, conventional diagnostic means may be utilized to determine when such material has reached to the target site(s), and then intense electromagnetic radiation may then be timely applied.

Example of the Preparation of a Nanomagnetic Material Coating

The following examples are presented to illustrate the preparation of nanomagnetic material but are not to be deemed limitative thereof. Unless otherwise specified, all parts are by weight, and all temperatures are in degrees Celsius.

In these examples, the fabrication of nanomagnetic materials was accomplished by a novel PVD sputtering process. A Kurt J. Lesker Super System III deposition system outfitted with Lesker Torus 4 magnetrons was utilized; the devices were manufactured by the Kurt J. Lekser Company of Clairton, Pa.

The vacuum chamber of the system used in these examples was cylindrical, with a diameter of approximately one meter and a height of about 0.6 meters. The base pressure used was from 1 to 2 micro-torrs.

The target used was a metallic FeAl disk with a diameter of about 0.1 meters. The molar ratio between the Fe and Al atoms was about 70/30.

In order to fabricate FeAl films, a direct current power source as utilized at a power level of from 150 to 550 watts; the power source was an Advanced Energy MDX Magnetron Drive.

The sputtering gas used was argon, with a flow rate of from 15 to 35 sccm.

In order to fabricate FeAlN films, a pulse system was added in series with the DC power supply to provide pulsed DC. The magnetron polarity switched from negative to positive at a frequency of 100 kilohertz, and the pulse width for the positive or negative duration was adjusted to yield suitable sputtering results (Advanced Energy Sparc-1e V).

In addition to using argon flowing at a rate of from 15 to 25 sccm, nitrogen was supplied as a reactive gas with a flow rate of from 15 to 30 sccm. During fabrication, the pressure was maintained at 2-4 milli-torrs.

The substrate used was either a flat disk or a cylindrical rod. A typical flat disk used was a silicon wafer with or without a thermally grown silicon dioxide layer, with a diameter of from 0.1 to 0.15 meters. The thickness of the silicon dioxide layer was 50 nanometers. A typical rod was an aluminum rod or a stainless steel wire with a length of from 0.1 to 0.56 meters and a diameter of from 0.0008 to 0.003 meters.

The distance between the substrate and the target was from 0.05 to 0.26 meters. To deposit a film on a wafer, the wafer was fixed on a substrate holder, and there was no rotational motion. To deposit a film on a rod of wire, the rod or wire was rotated at a speed of from 0.01 to 0.1 revolutions per second and was moved slowly back and forth along its symmetrical axis with the maximum speed being 0.01 meters per second.

A typical film thickness was between 100 nanometers and 1 micron, and a typical deposition time was between 200 and 2000 seconds. The resistivity of an FelAl films was approximately $8 \times 10^{-6}$ Ohm-meter. The resistivity of an FeAlN film is approximately $200 \times 10^{-6}$ Ohm-meter. The resistivity of an FeAlO film was about 0.01 Ohm-meter.

The fabrication conditions used for FeAlO films was somewhat different than those used for FeAl films. With the former films, the target was FeAlO, and the source was radio frequency with a power of about 900 watts.

Materials Characterization

According to surface profiler and SEM cross-sectional measurements, the film thickness variation in a flat area of 0.13 meters×0.13 meters was within 10 percent. As revealed by AFM measurement, the surface roughness of an FeAl film was about 3 nanometers, and that of an FeAlN film was about 2 nanometers. All films were under compressive stress with the values for FeAl films under $355 \times 10^6$ Pascal, and those for FeAlN films under $675 \times 10^6$ Pascal.

In order to determine the average chemical composition of a film, EDS was utilized to study the composition at four spots of the film, with a spot size of about 10 microns×10 microns× 10 microns. For an FeAl film, the molar ratio of Fe/Al was about 39/61; and, for an FeAlN film, the molar ration of Fe/Al/N was about 19/25/56.

In each of the films, the Fe/Al ratio was different from that in the target; and the relative iron concentration was lower than the effective aluminum concentration.

The surface chemistry was studied via XPS. It was found that, on the top surface of an FeAl film, within the top 10 nanometers, oxygen was present in addition to Fe and Al; and the molar ratio of Fe/Al/O was 17/13/70. It was found that, on the top surface of an FeAlN film oxygen was also present in addition to Fe, Al, and N; and the molar ratio of Fe/Al/N/0 was 20/13/32/34.

In contrast to the average chemical composition of the films, on the surface of the FeAl or FeAlN films, the relative iron concentration was higher than the relative aluminum concentration. To observe the variations of the Fe/Al ratio below the top surface, SIMS was utilized. It was found that the relative Fe/Al ratio decreases as the distance from the top increases.

Figure 43:
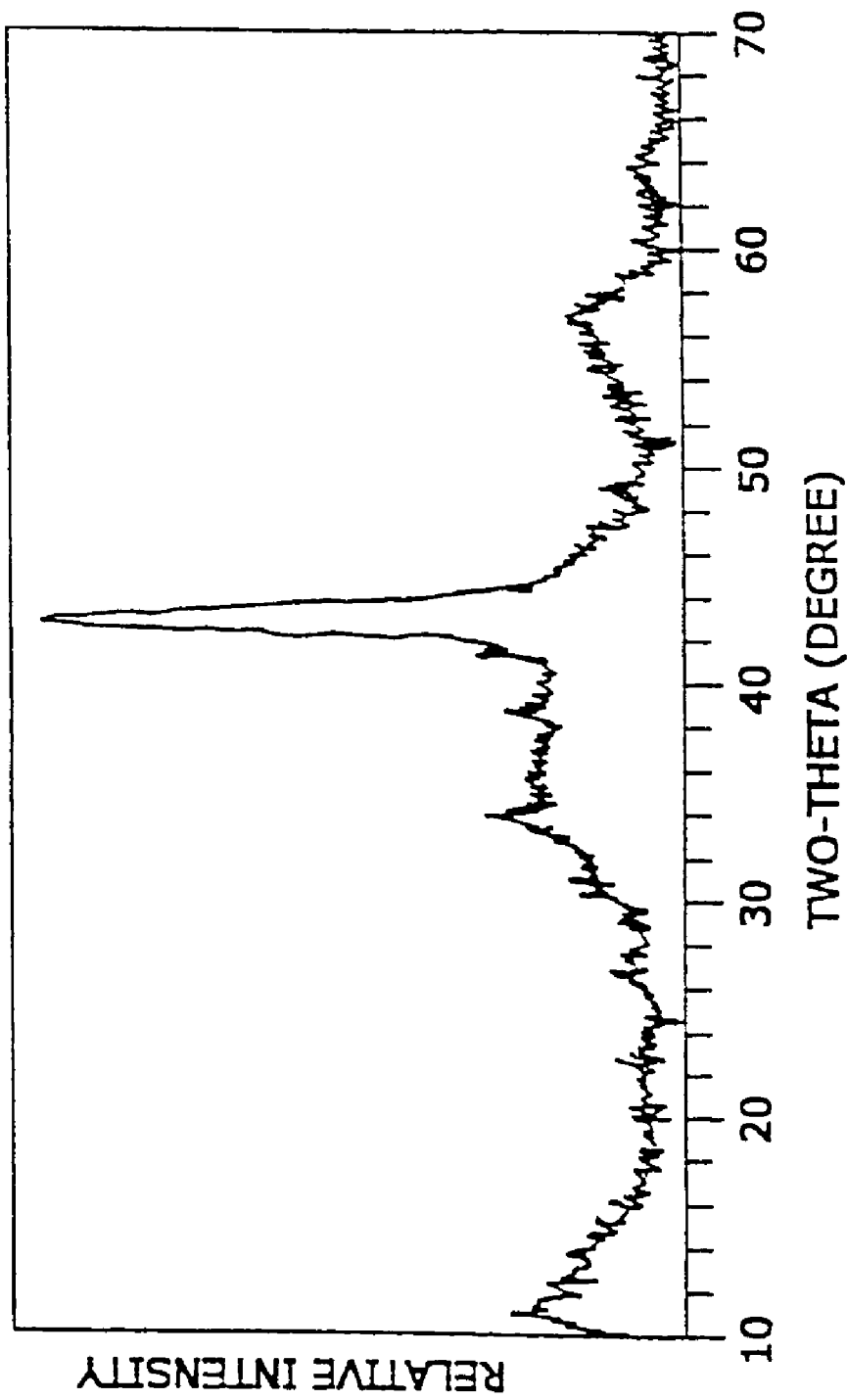
FIGS. 43-47 are graphs depicting the properties of certain films.

Both XRD and TEM were utilized to study the phase formation. FIG. 43 illustrates the XRD pattern for an FeAl film. Besides broad amorphous peaks, the major peak around 44 degrees coincides with the main diffraction peaks of FeAl alloys, such as $AlFe_3$ (JCPDS Card number 45-1203), and $Al_{0.4}Fe_{0.6}$ (JCPDS Card number 45-0982). The average crystal size was estimated to be 7 nanometers by a computer program called "SHADOW" (S. A. Howard, "SHADOW: A system for X-ray powder diffraction pattern analysis: Annotated program listings and tutorial," University of Missouri-Rolla, 1990).

SEM analyses confirmed that both amorphous and crystalline phases were present in the films, and the sizes of the crystals were between 10 nanometers and 30 nanometers.

The XRD pattern of an FeAlN film indicated that several broad diffraction patterns are present, suggesting an amorphous growth. This amorphous growth was confirmed by TEM. For FeAlO films, as revealed by XRD and TEM, amorphous growth was the dominating mechanism.

Magnetic Properties

Figure 44:
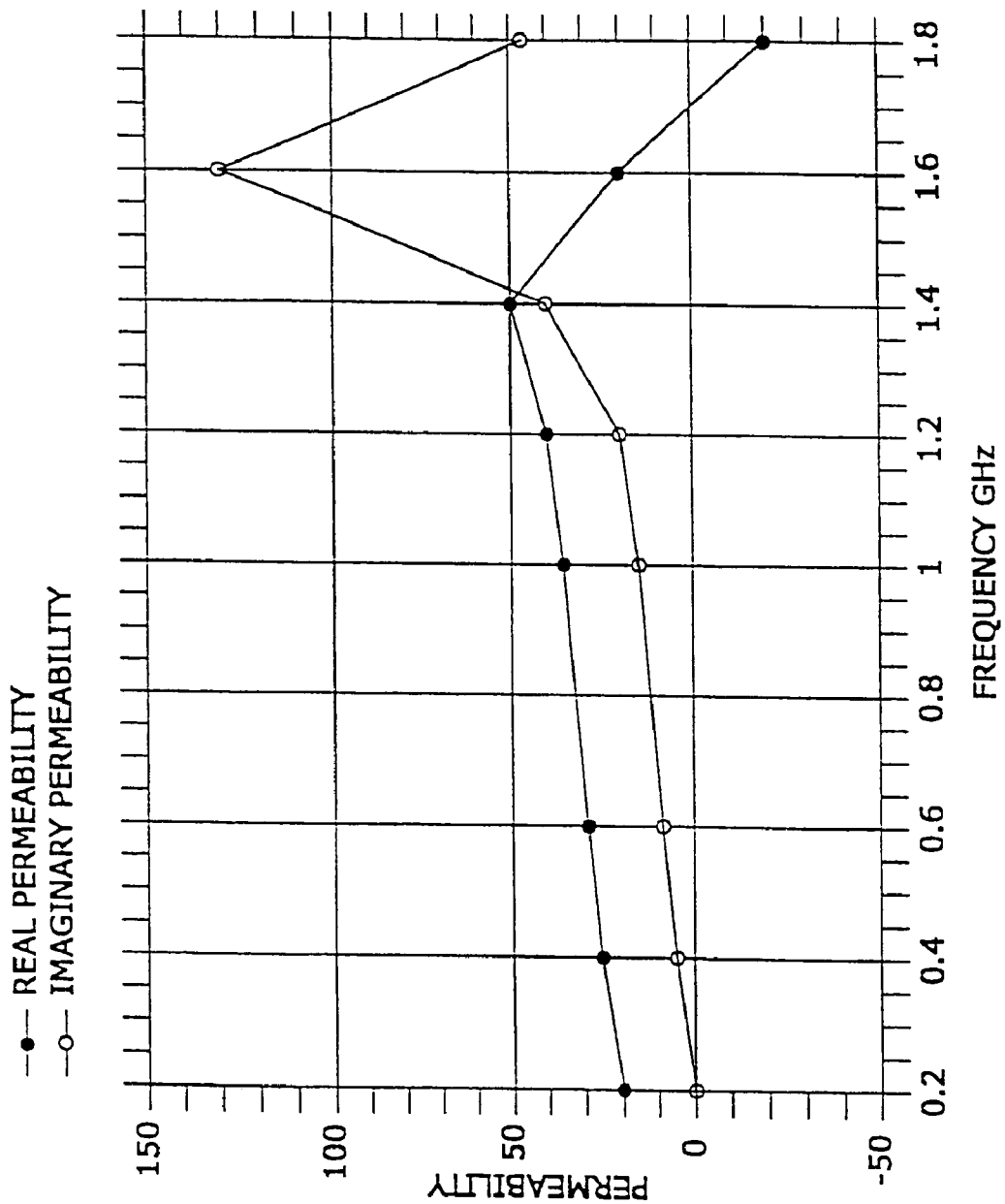
Figure 45:
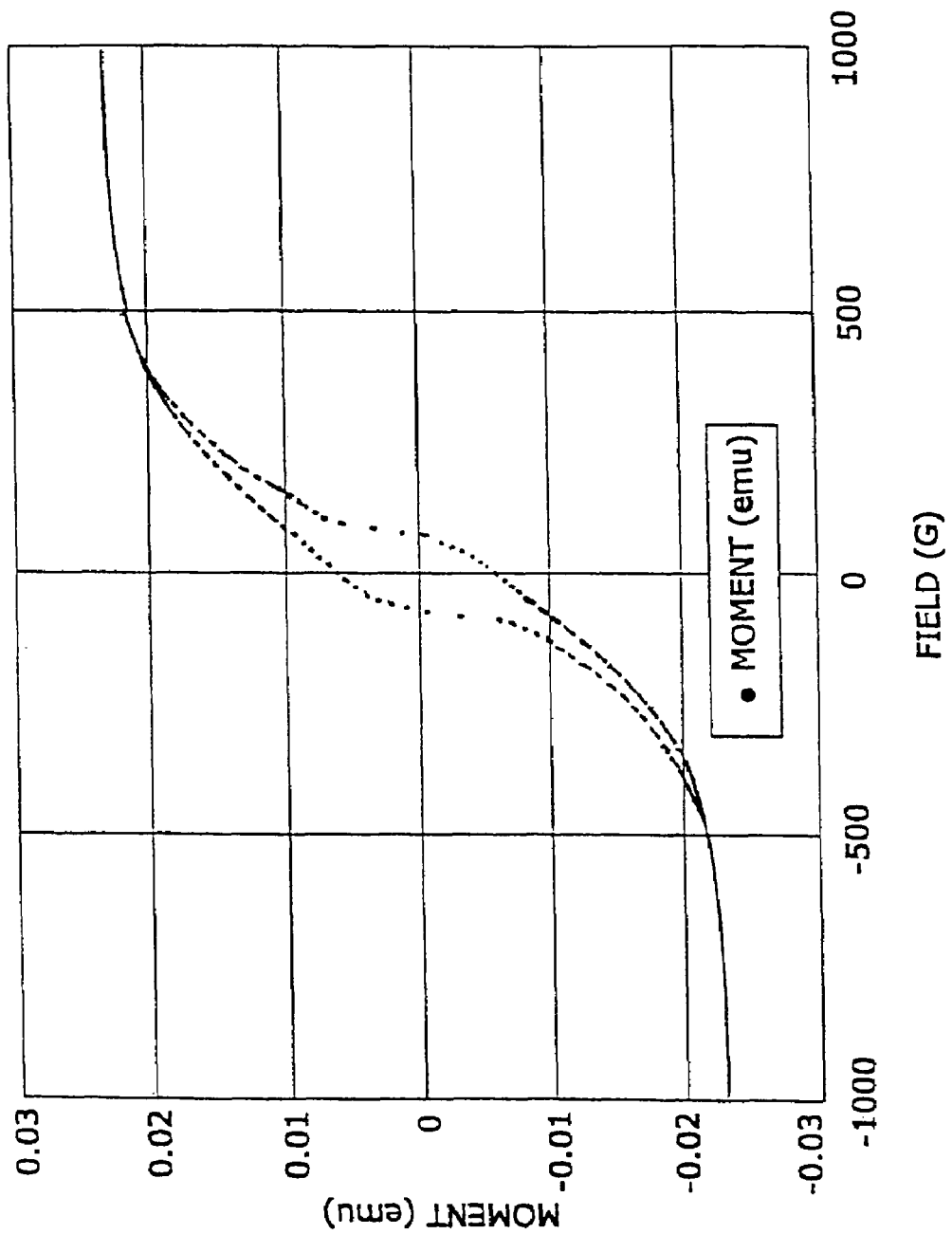
Figure 46:
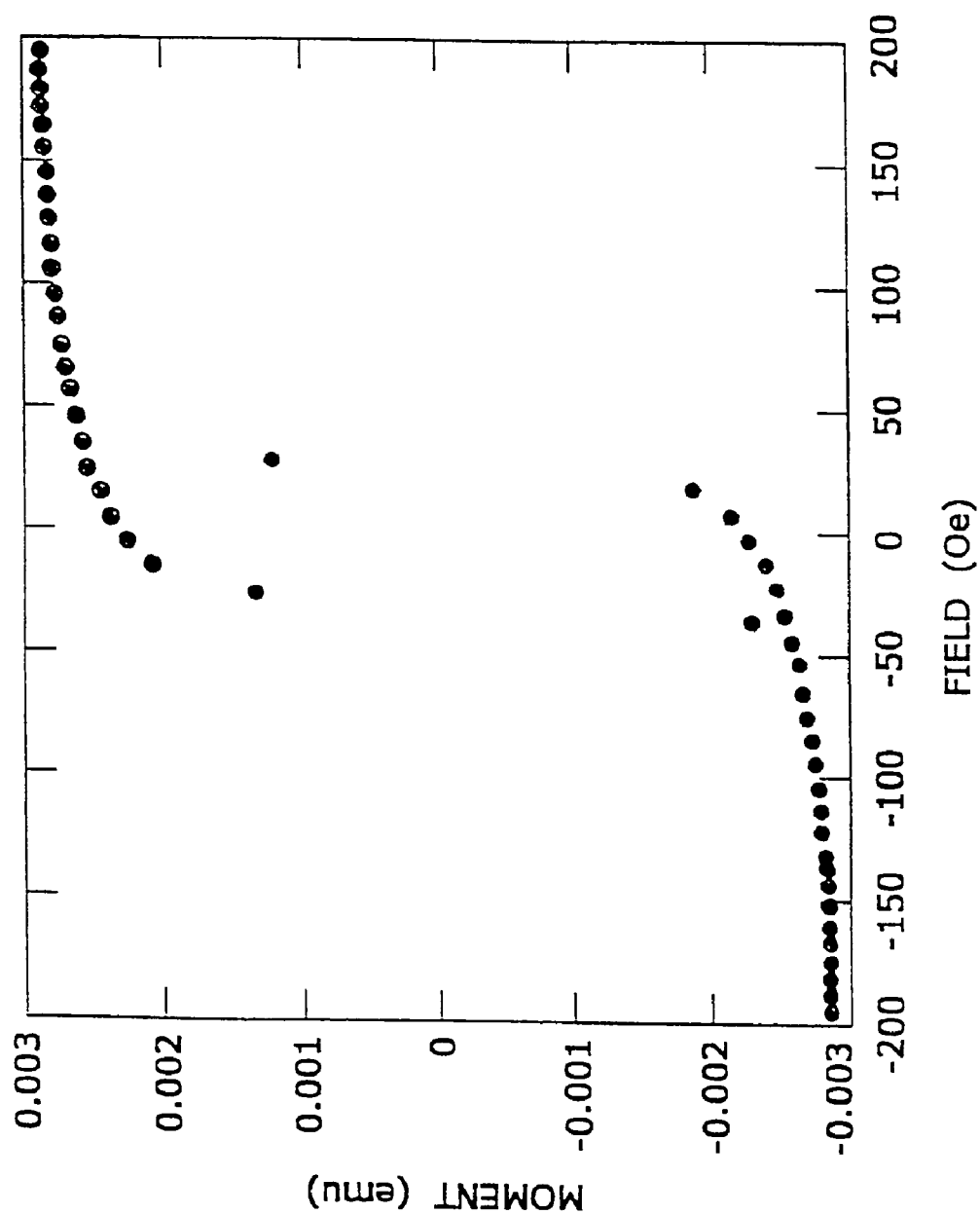
Figure 47:
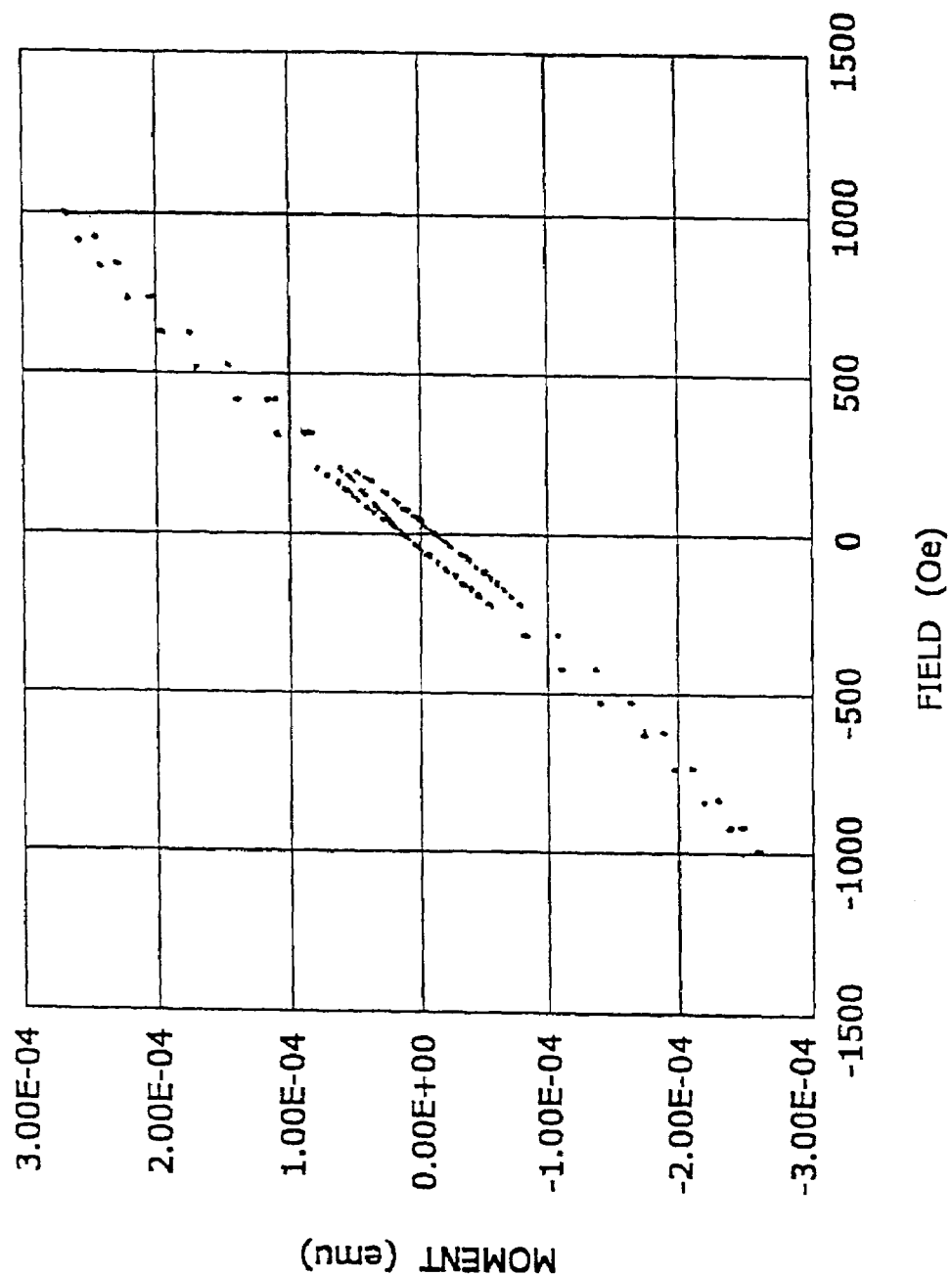

For an FeAl film with a thickness of about 500 nanometers, the real part of the relative permeability was about 40 in a direct current field and an alternating current field with a frequency lower than 200 Megahertz, and the imaginary part of the permeability is nearly zero at frequencies lower than 200 Megahertz. In FIG. 44, the real and imaginary parts of the permeability were plotted as functions of frequency between 200 Megahertz and 1.8 GHz. The value of the real part increases slightly as the frequency increases, reaching a maximum value of 100 near 1.4 GHz, and it decreases to zero near 1.7 GHz. The value of the imaginary part reaches its maximum value at 1.6 GHz. Thus, the ferromagnetic resonance frequency of the film is near 1.6 GHz. In FIG. 45, a hysteresis loop for the FeAl film is illustrated. The loop appeared to have two sections. One section was in the region between plus and minus 100 G, which has some squareness similar to that illustrated in FIG. 4 for a thinner film. The other section was either was 100 G and 400 G, or between −100 G and −400 G, which may be indicating that the effective magnetic moment is approximately 0.046 emu, and the saturation magnetization, 4πMs, is 9,120 Gauss. The effective anisotropy field is approximately 400 G. For another FeAl film, with a thickness of about 150 nanometers, a magnetic loop measured with VSM (at 300K) is illustrated in FIG. 46. The coercive force (Hc) was approximately 30 Oersted, the remanence magnetic moment was about 0.0044 emu, and the saturation magnetic moment was about 0.0056 emu. Thus, the squareness of the loop was about 80 percent. Correspondingly, the remanence magnetization (4πMr) is about 2,908 G, and the saturation magnetization (4πMs) is about 3700 G. For an FeAlN film, with a thickness of about 414 nanometers, a magnetic hysteresis loop measured with SQUID (at 5 K) is illustrated in FIG. 47. The coercive force, Hc, is about 40 Oersted, the remanence magnetic moment was about 0.000008 emu, and the saturation magnetic moment was about 0.000025 emu. Correspondingly, the remanence magnetization was about 64 G, and the saturation magnetization was about 2,000 G. The relative permeability was about 3.3. At 300 K, the value of the relative permeability is reduced to one, and the values of Hc, Mr, and Ms are also reduced.

For FeAlO films with thicknesses between 145 and 189 nanometers, the hysteresis loop of each film is similar to the FeAlN film. At 300 K, the relative permeability ranges from 0.28 to 3.3, Hc ranges from 20 to 132 Oe, 4πMr ranges from 12 to 224 G, and 4πMs ranges from 800 to 1,640 G. The ferromagnetic resonance frequency of an FeAlO film is about 9.5 Gigahertz.

Figure 48:
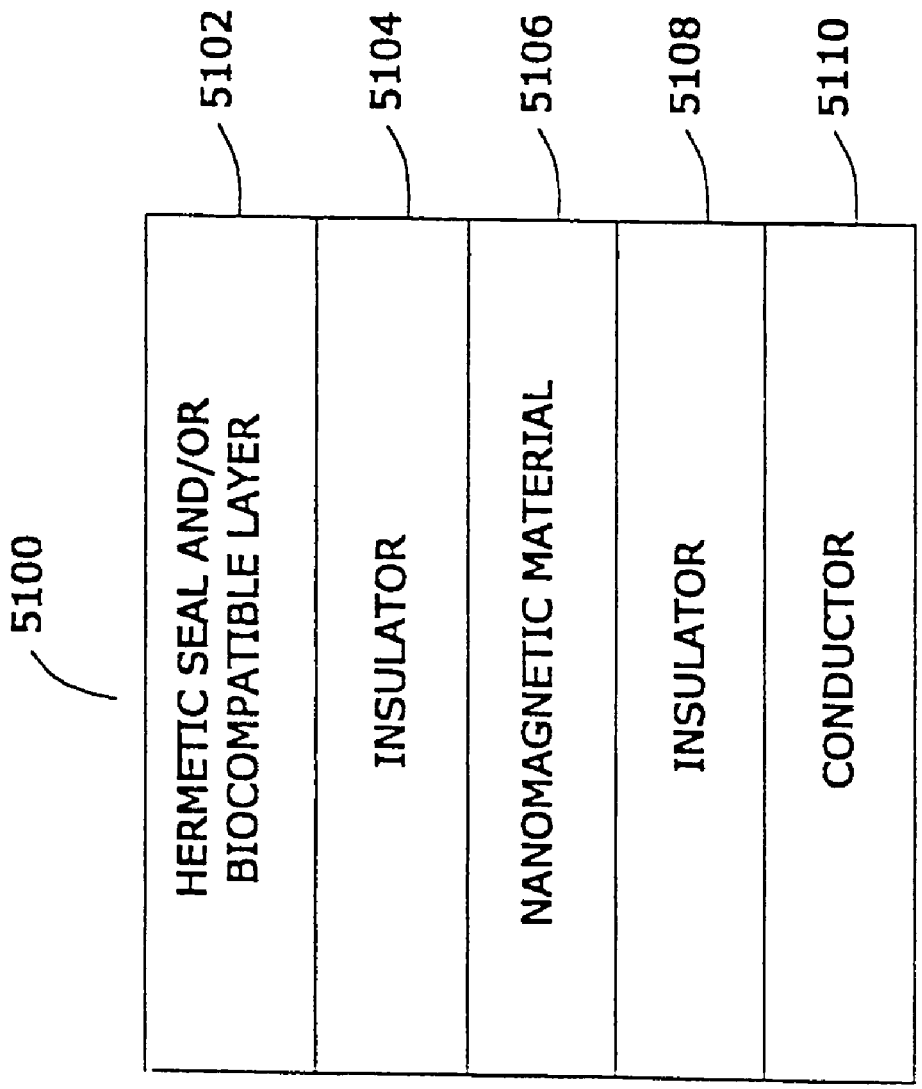
FIG. 48 is a schematic of a particular assembly comprised of a layer of nanomagnetic material.

FIG. 48 is a schematic of a composite structure 5100 comprised of a layer 5102 material that acts as a hermetic seal and/or is biocompatible. The layer 5102 is disposed over insulator layer 5104; insulator layer 5104, in one embodiment, is not continuous.

The insulator layer 5104 is disposed over a layer 5106 of nanomagnetic material; in one embodiment, nanomagnetic material layer 5106 is not continuous. Layer 5106 is disposed over a layer 5108 of insulative material that, in turn, is disposed over conductor layer 5110.

As will be apparent, the use of the insulating/dielectric layers 5104 and 5104 together with the conductor layer 5110 has an effect upon the capacitance of the structure 5100. Similarly, the use of the layer 5106 of nanomagnetic material affects the inductance of the structure 5100.

By varying the characteristics and the properties of the insulator layers 5104/5108, and of the nanomagnetic material 5106, one can, e.g., increase both the capacitance and the inductance of the system. In one embodiment, the inductance of system 5100 increases substantially, but the capacitance is not changed much.

A Novel Magnetic Resonance Imaging Assembly

In another embodiment of this invention, there is provided a magnetic resonance imaging assembly which utilizes an implanted medical device that does not heat substantially during exposure to MRI radiation but which, nonetheless, provides detectable feedback from such radiation.

In one aspect of this embodiment, there is provided a magnetic resonance imaging tracking assembly that comprises a medical device comprising a magnetic shield, means for generating a first high frequency electromagnetic wave, means for sensing a modified high-frequency electromagnetic wave, means for producing an image from said modified high-frequency electromagnetic wave, and means for modifying said image produced from said modified high-frequency electromagnetic wave.

Figure 49:
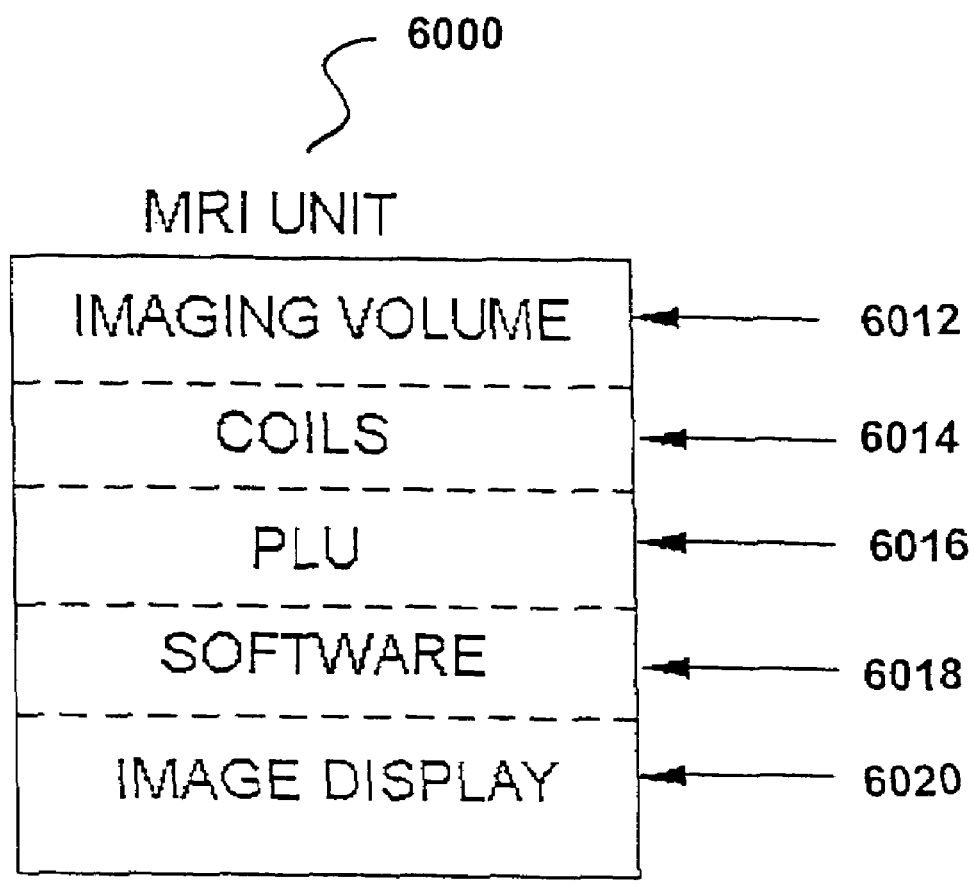
FIG. 49 is a schematic diagram of a magnetic resonance imaging (MRI) assembly.

FIG. 49 is a block diagram illustrating the components of a typical magnetic resonance imaging (MRI) unit 6000. This MRI unit 6000 is comprised of means 6014 for producing certain types of electromagnetic radiation. Such radiation is generally comprised of alternating electromagnetic waves with a frequency of at least about 21 megahertz, depending on $B_0$.

MRI units with the capability of producing such electromagnetic radiation are well known. Reference may be had, e.g., to U.S. Pat. No. 4,733,189 (magnetic resonance imaging systems); U.S. Pat. No. 4,449,097 (nuclear magnetic resonance systems); U.S. Pat. No. 5,867,027 (magnetic resonance imaging apparatus); U.S. Pat. No. 5,568,051 (magnetic resonance imaging apparatus having superimposed gradient coil); U.S. Pat. No. 5,329,232 (magnetic resonance methods and apparatus); and the like. The entire disclosure of each of these United States patents is hereby incorporated by reference into this specification.

Referring again to FIG. 49, and in the preferred embodiment depicted therein, it will be seen that MRI unit 6000 comprises an imaging volume 6012 into which a patient or other sample to be imaged is placed. In some MRI units, only a portion of the patient is placed within the imaging volume 6012 while the rest of the patient is outside the imaging volume 6012.

In many MRI units, the imaging volume 6012 is the space enclosed by one or more MRI coils. The patient is disposed within such space and impacted over a 360-degree radius by radiation from such coils.

Thus, and referring again to FIG. 49 and to the embodiment depicted therein, the MRI system 6000 preferably contains coils 6014 that, in one embodiment, are usually comprised of a main coil (not shown) for generating a uniform magnetic field (not shown) through the imaging volume 6012. The coils 6014 also preferably comprise gradient coils (not shown) to generate linear gradient magnetic variation in the imaging volume 6012, radio frequency transmit coils (not shown) for transmitting a magnetic resonance excitation signal train, and one or more pickup coils (not shown) to receive the de-excitation nuclear signals from the imaging sample placed in the imaging volume 6012. Reference may be had, e.g., to U.S. Pat. No. 4,860,221 (magnetic resonance imaging system), U.S. Pat. No. 5,184,074 (real-time MR imaging inside gantry room), U.S. Pat. No. 5,874,831 (magnetic resonance imaging system), U.S. Pat. No. 5,779,637 (magnetic resonance imaging system including an image acquisition apparatus rotator), U.S. Pat. No. 5,332,972 (gradient magnetic field generator for MRI system), and the like. The entire disclosure of each of these United States patents is hereby incorporated by reference into this specification.

As will be apparent to those skilled in the art, one may utilize other coils. In one embodiment, an imaging pickup coil(s) (not shown) which defines the imaging volume 6012 as the volume which the pickup coil(s) (not shown) are sensitive to, is placed inside a patient. Reference may be had, e.g., to U.S. Pat. No. 5,476,095 (intracavity probe and interface device for MRI imaging and spectroscopy); U.S. Pat. No. 5,451,232 (probe for MRI imaging and spectroscopy particularly in the cervical region); U.S. Pat. No. 5,307,814 (externally moveable intracavity probe for MRI imaging and spectroscopy); U.S. Pat. No. 6,263,229 (miniature magnetic resonance catheter coils and related methods); U.S. Pat. No. 6,171,240 (MRI RF Catheter Coil); and the like. The entire disclosure of each of these United States patents is hereby incorporated by reference into this specification.

Referring again to FIG. 49, and to the preferred embodiment depicted therein, the MRI unit 6000 preferably contains one or more programmable logic units (PLU) 6016 for controlling the coils (6014). In the embodiment depicted, the PLU processes the received signals and creates an image of an internal region (not shown) of the patient (not shown). See, e.g., the United States patents cited above as well as U.S. Pat. No. 6,445,182 (geometric distortion correction in magnetic resonance imaging); U.S. Pat. No. 6,046,591 (MRI system with fractional decimation of acquired data); and U.S. Pat. No. 6,414,487 (time and memory optimized method of acquiring and reconstructing multi-shot three-dimensional MRI data). The entire disclosure of each of these United States patents is hereby incorporated by reference into this specification.

Referring again to FIG. 49, an image is displayed onto a display screen 6020. This and other tasks of the PLU 6016 are controlled by the software 6018 which the PLU executes.

In one embodiment, and referring again to FIG. 49, the software 6018 is adapted to apply different signal filtering and image filtering algorithms to the received signals. Thus, if some characteristic of the received signal is known to be caused by known material in the imaging volume 6012, it is possible to enhance or eliminate the known material from the displayed image. For example, bone will have a different MRI de-excitation signal than tissue. It is therefore possible to program the software to enhance the tissue signal and the tissue image displayed to the physician while diminishing the signal from the bone material, thus diminishing or eliminating the bone image in the final displayed image. This may be accomplished in part by filtering the received signals.

Manipulation of the image data collected by an MRI system, as well as the manipulation of the re-constructed image, is well known to those skilled in the art. Reference may be had to U.S. Pat. No. 6,459,922 (post data-acquisition method for generating water/fat separated MR images having adjustable relaxation contrast). This patent discloses "A post data-acquisition magnetic resonance imaging (MRI) method is disclosed for generating water/fat separated MR images wherein the resultant contrast in water-only or fat-only images is made adjustable under operator control." The entire disclosure of this United States patent is hereby incorporated by reference into this specification.

Reference may also be had to U.S. Pat. No. 5,909,119 (method and apparatus for providing separate fat and water MRI images in a single acquisition scan) and U.S. Pat. No. 5,708,359 (interactive, stereoscopic magnetic resonance imaging system). The U.S. Pat. No. 5,708,359 patent discloses further image manipulation, stating that: "Described are a preferred system and method for acquiring magnetic resonance signals which can be viewed stereoscopically in real or near-real time. The preferred stereoscopic MRI systems are interactive and allow for the adjustment of the acquired images in real time, for example to alter the viewing angle, contrast parameters, field of view, or position associated with the image, all advantageously facilitated by voice-recognition software." The entire disclosure of this United States patent is hereby incorporated by reference into this specification.

Reference also may be had to U.S. Pat. No. 6,175,655 (medical imaging system for displaying, manipulating and analyzing three-dimensional images). This patent discloses "A method and device for generating, displaying and manipulating three-dimensional images for medical applications is provided. The method creates a three-dimensional images from MRI or other similar medical imaging equipment. The medical imaging system allows a user to view the three-dimensional model at arbitrary angles, vary the light or color of different elements, and to remove confusing elements or to select particular organs for close viewing. Selection or removal of organs is accomplished using fuzzy connectivity methods to select the organ based on morphological parameters." The entire disclosure of this United States patent is hereby incorporated by reference into this specification.

Reference also may be had U.S. Pat. No. 6,486,671 (MRI image quality improvement using matrix regularization); U.S. Pat. No. 6,377,835 (method for separating arteries and veins in three-dimensional MR angiographic images using correlation analysis); U.S. Pat. No. 5,872,861 (digital image processing method for automatic detection of stenoses); U.S. Pat. No. 6,345,112 (method for segmenting medical images and detecting surface anomalies in anatomical structures); U.S. Pat. No. 6,426,994 (Image processing method); and U.S. Pat. No. 6,463,167 (Adaptive filtering). The entire disclosure of each of these United States patents is hereby incorporated by reference into this specification.

Figure 50:
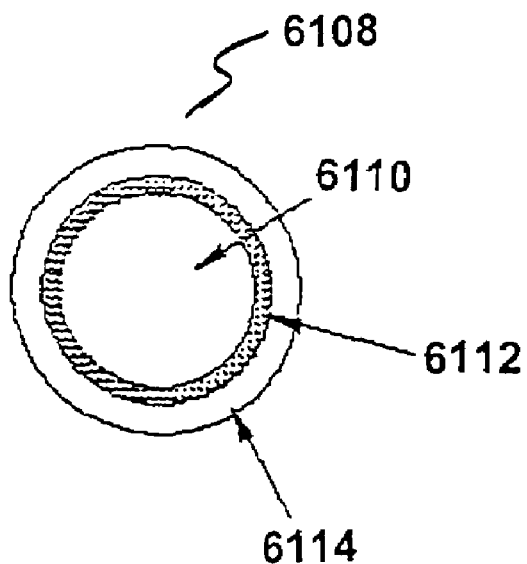
FIG. 50 is a sectional view of a shielded medical instrument that, when implanted, is adapted to produce minimal image artifacts from the electromagnetic waves produced during MRI imaging.

FIG. 50 shows a cross section of a portion of a medical device 6108 around which a magnetic shield 6114 is disposed. The medical device 6108 in the embodiment depicted is preferably a catheter with a hollow lumen 6110 defined by a wall 6112. In another embodiment (not shown) the medical instrument is a catheter with multiple lumens. In another embodiment, not shown, the medical instrument 6108 is a stent with hollow lumen 6110 defined by a wall 6112. In another embodiment, not shown, the medical instrument 6108 is a biopsy needle with hollow lumen 6110 defined by a wall 6112.

In the embodiment depicted in FIG. 50, a layer of shielding material 6114 is coated onto and is contiguous with the exterior surface/wall 6112 of the medical device 6110. In another embodiment, not shown in FIG. 50, the shielding material 6114 is disposed between the source of electromagnetic radiation and the wall 6112 but is not necessarily contiguous therewith. In this latter embodiment, e.g., a layer of insulating material, that does not act as a magnetic shield may be disposed between the wall 6112 and the magnetic shield 6114.

In one embodiment, the magnetic shield 6114 is comprised of from about 10 to about 90 weight percent of nanomagnetic material with certain specified properties. This type of material is disclosed in applicants' U.S. Pat. No. 6,506,972, the entire disclosure of which is hereby incorporated by reference into this specification.

As is disclosed in U.S. Pat. No. 6,506,972, nanomagnetic material is magnetic material which has an average particle size less than 100 nanometers and, preferably, in the range of from about 2 to 50 nanometers. Reference may be had, e.g., to U.S. Pat. No. 5,889,091 (rotationally free nanomagnetic material); U.S. Pat. Nos. 5,714,136; 5,667,924, and the like. The entire disclosure of each of these United States patents is hereby incorporated by reference into this specification.

Referring again to FIG. 50, it is preferred that the shield 6114 provide a shielding efficiency of at least about 0.5 and, more preferably, at least about 0.9. The shielding efficiency referred to is calculated by measuring the magnetic field strength outside of the shield 6114 and the magnetic field strength within lumen 6110. The difference in these field strengths is the degree to which the shielding is effective. This shielding effectiveness, when divided by the magnetic field strength outside of the shield 6114, is the shielding efficiency.

Figure 51:
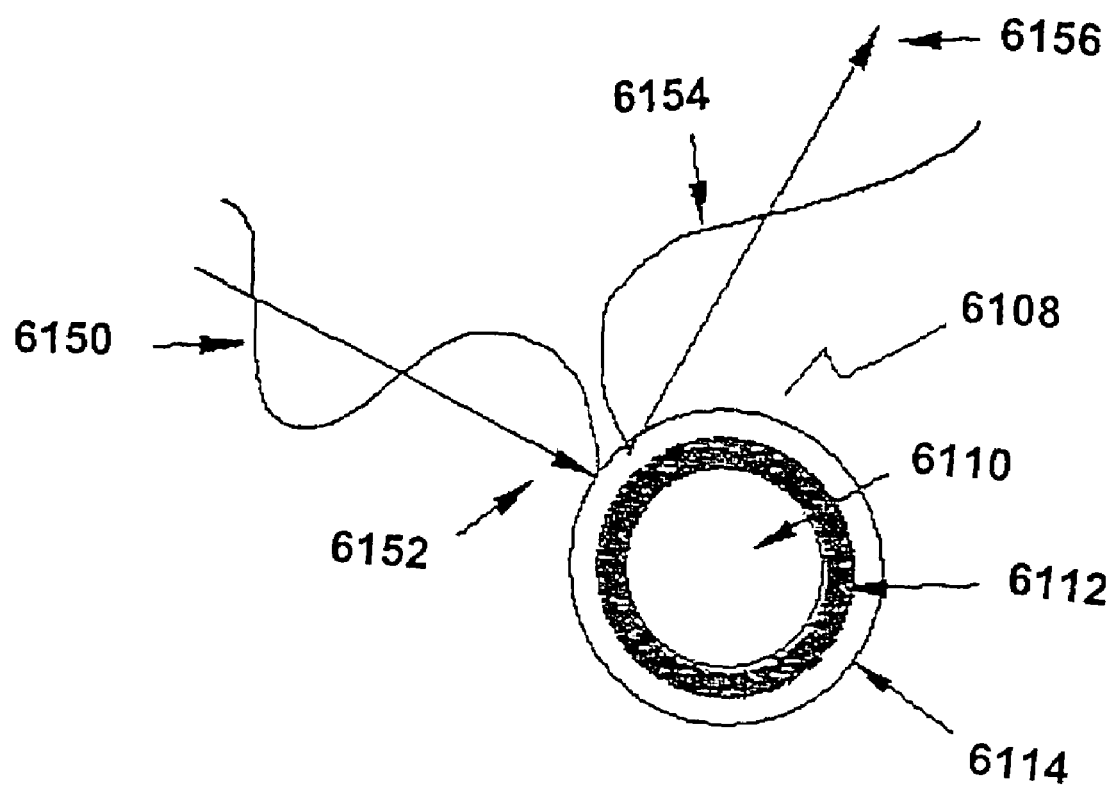
FIGS. 51 and 52 are schematic representations of the effects of a high-frequency electromagnetic wave upon a particular substrate.

FIG. 51 is a schematic diagram illustrating a typical reaction of a shielded medical device 6108 to MRI radiation. Referring to FIG. 51, and in the embodiment depicted therein, a known radio frequency electromagnetic wave 6150 that is transmitted from the MRI unit 6000 (see FIG. 49) travels in the direction 6152. As will be apparent, and in this embodiment, the electromagnetic radiation is in the form of a sine wave 6150.

Sine wave 6150 travels in the direction of arrow 6152 and contacts shield 6114. In the embodiment depicted, sine wave 6150 is at least somewhat modified by shield 6114. As used in this specification, the term modified refers to an electromagnetic wave that is partially or totally absorbed and/or reflected and/or transmitted and/or phase changed, and the like.

In the embodiment depicted in FIG. 51, the wave is partially or totally reflected by shield 6114, to produce reflected wave 6154 traveling in the direction of arrow 6156.

As will be apparent, a change in direction is only one of the means in which incident wave 6150 is affected by shield 6114. As will be apparent from FIG. 51, the reflected wave 6154 has a wave shape that differs from incident wave 6150, and the wavelength of wave 6154 differs from wave 6150.

As will be apparent to those skilled in the art, when the MRI assembly 6000 detects the shift in wavelength caused to incident wave 6150, it can utilize its signal analyzing and filtering software (discussed elsewhere in this specification) to identify the reflected wave signal and to also identify the properties of the substrate that caused such reflected wave signal. As will be apparent, each particular shielded device 6108 will have its own electronic signature and the effect it has upon a specific MRI incident wave (or waves) can be determined.

Figure 52:
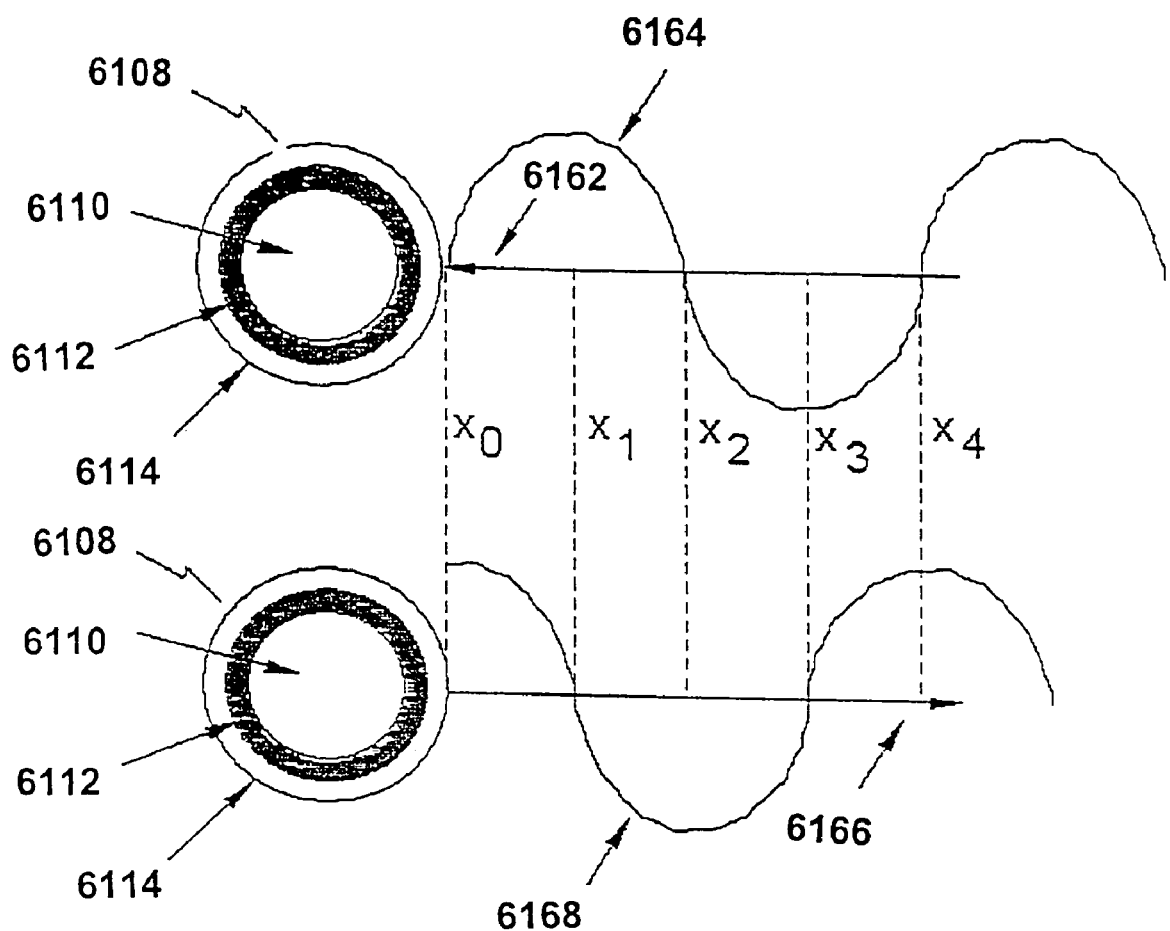

One embodiment of the invention is disclosed in FIG. 52. Thus, e.g., and referring to FIG. 52, a known radio frequency electromagnetic wave 6164 transmitted from the MRI unit 6000 of FIG. 49 in the direction 6162 is incident upon the radio frequency electromagnetic wave modifying material coating 6114 of medical instrument 6108.

The incident electromagnetic wave 6164 is out of phase with the reflected wave 6168, not being coincident in time therewith; see how incident wave 6164 is reflected from the material 6114 as indicated by the comparative markings labeled "$x_0$", "$x_1$", "$x_2$", "$x_3$", and "$x_4$". The reflected wave 6168 is shown traveling in the opposite direction 6166 to that of the incident wave 6164 direction 6162 only for convenience in illustrating the phase shift which occurs between the incident 6164 and reflected 6168 waves. In general, the reflected wave 6168 direction will not be exactly opposite to the incident wave 6164 direction 6162. Knowing the reflected wave's characteristics, such as the phase shift of the incidence wave 6164 caused by the material coating 6114 allows the software 6018 of FIG. 49 to be modified to either enhance or reduce the visibility of the medical instrument 6108 in the image displayed to the physician. In one embodiment, such image filtering is adjusted in real-time by the physician who may wish to alternately have the medical instrument 6108 displayed and not displayed at various stages of a medical procedure.

In another embodiment (not shown) the radio frequency and gradient electromagnetic waves transmitted by the MRI system 6000 causes the nuclei of the material coating (6114 of FIG. 50) to resonate and to producing a nuclear resonance response signal detectable by the MRI system 6000. Such a nuclear resonance signal from the material 6114 is distinct from any bio-material naturally occurring in a patient.

Figure 53:
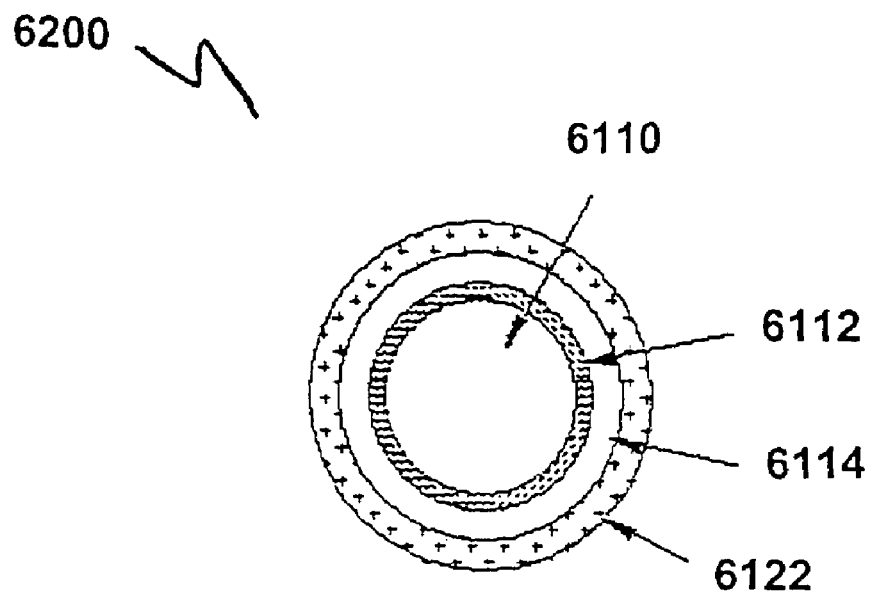
FIGS. 53 through 55 are schematic illustrations of several shielded medical devices that may be used in the assembly of this invention.

FIG. 53 is a schematic cross-sectional view of a portion of a medical device 6200 that comprises a magnetic shield material 6114 disposed onto the surface of the wall 6112 of the device 6200. The medical device 6200 in the embodiment depicted is preferably a catheter with a hollow lumen 6110 defined by a wall 6112. A biologically inert coating 6122 is applied over the magnetic shield material 6114. Biologically inert coating 6122 may be, e.g., Teflon, Tefzel or other material. In one embodiment, the biologically inert coating 6122 is an antithrombogenic coating.

Figure 54:
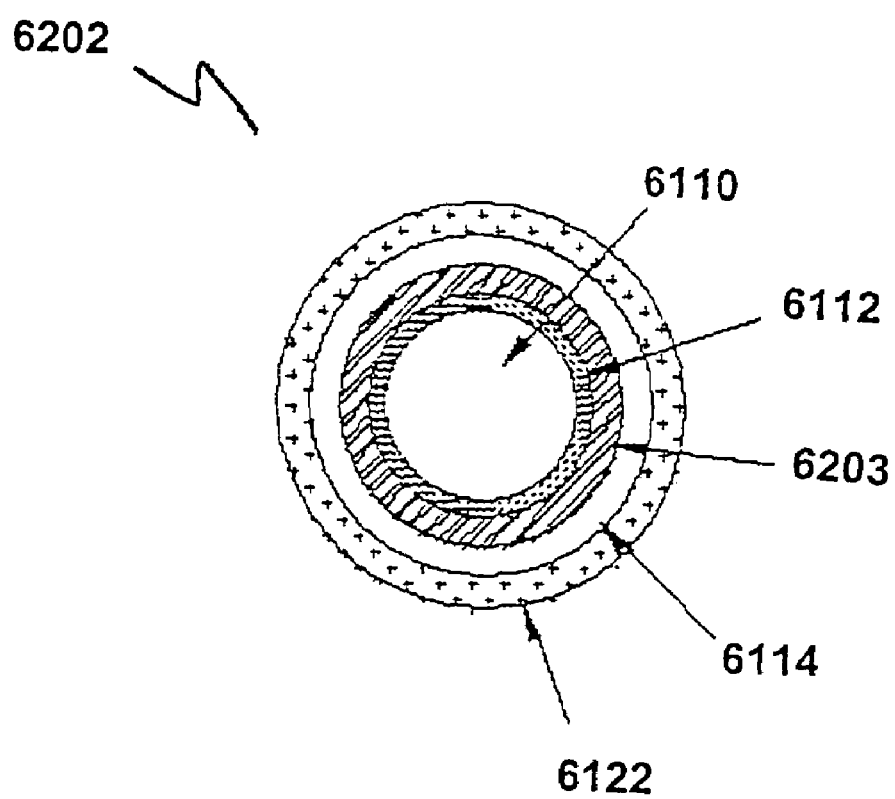

FIG. 54 is a schematic cross-sectional view of a portion of a medical device 6202 comprising a hollow lumen 6110 defined by walls 6112. The walls 6112 are preferably coated with a bonding material 6203 before the magnetic shield material 6114 is applied. Applying material 6203 enhances the ability of the magnetic shield material 6114 to adhere to the medical device 6202. Material 6203 may be, e.g., a thin film coating of aluminum or other deposition of thin film material and depends on the composition of the walls 6112 and the shield material 6114. A biologically inert material 6122 is optionally applied to the magnetic shield material 6114.

Figure 55:
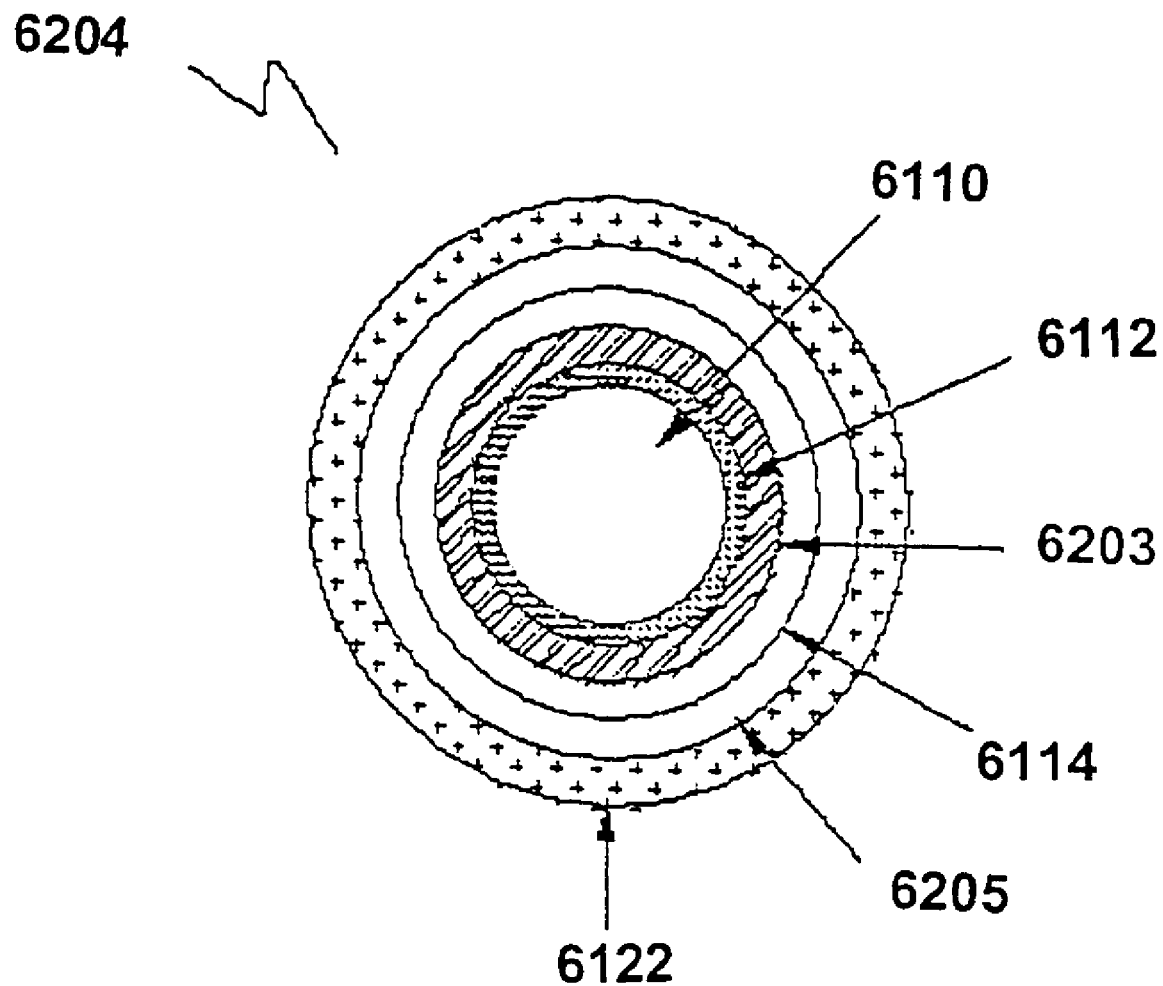

FIG. 55 shows a cross section of a medical device 6204 comprising a hollow lumen 6110 defined by the walls 6112. The walls 6112 are coated with an optional bonding material 6203. Magnetic shield material 6114 is applied over the bonding material 6203.

In another embodiment (not shown, but refer to FIG. 50) the magnetic shield material is applied directly to wall 6112.

Continuing to refer to FIG. 55 and to the embodiment depicted therein, a second magnetic shield material 6205 is applied over the magnetic shield material 6114. In one embodiment the magnetic shield material 6205 has a different composition than that of magnetic shield material 6114.

Continuing to refer to FIG. 55, an optional outer biologically inert coating 6122 is applied to magnetic shield material 6205.

Figure 56A:
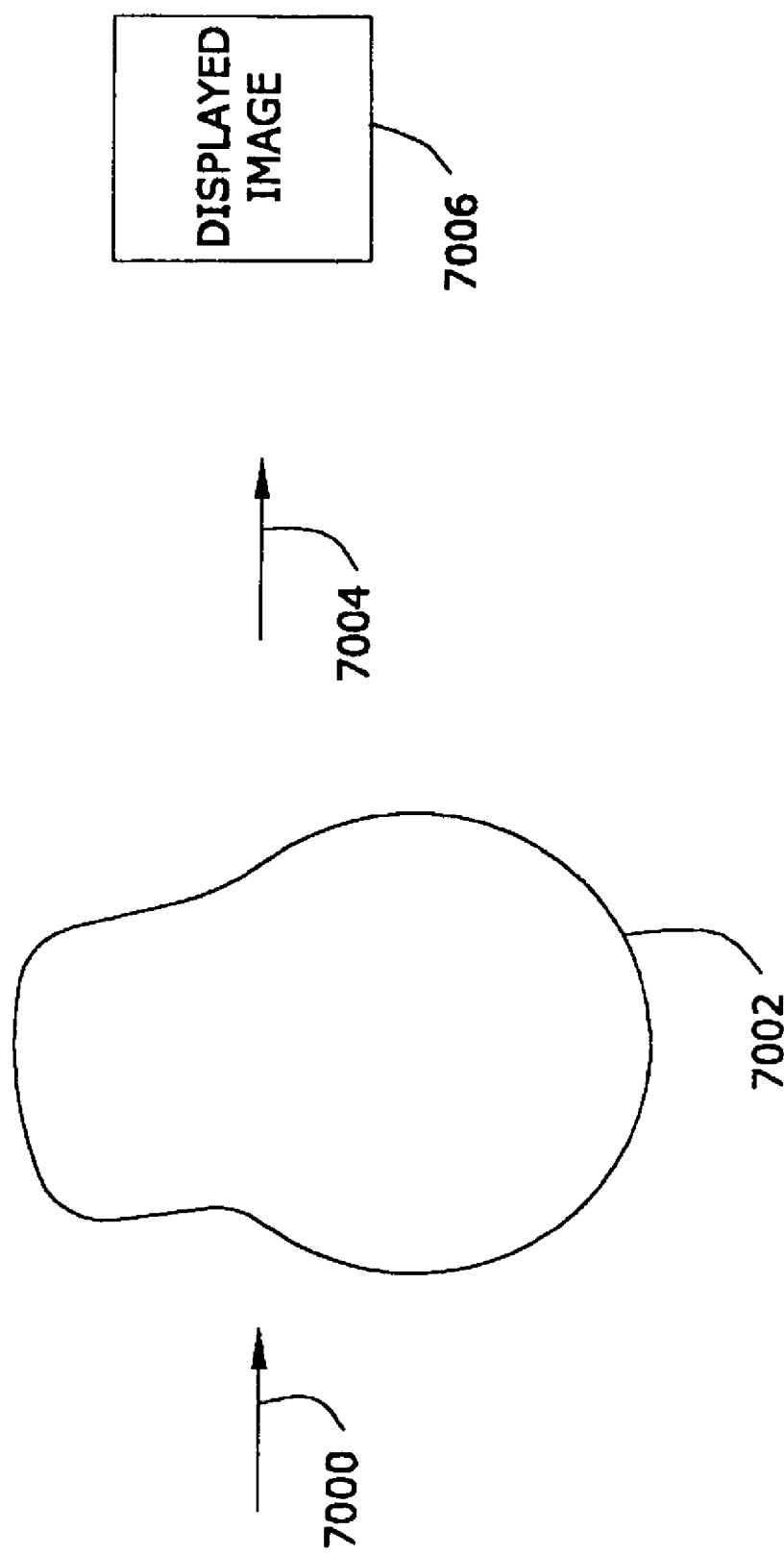
Figure 56C:
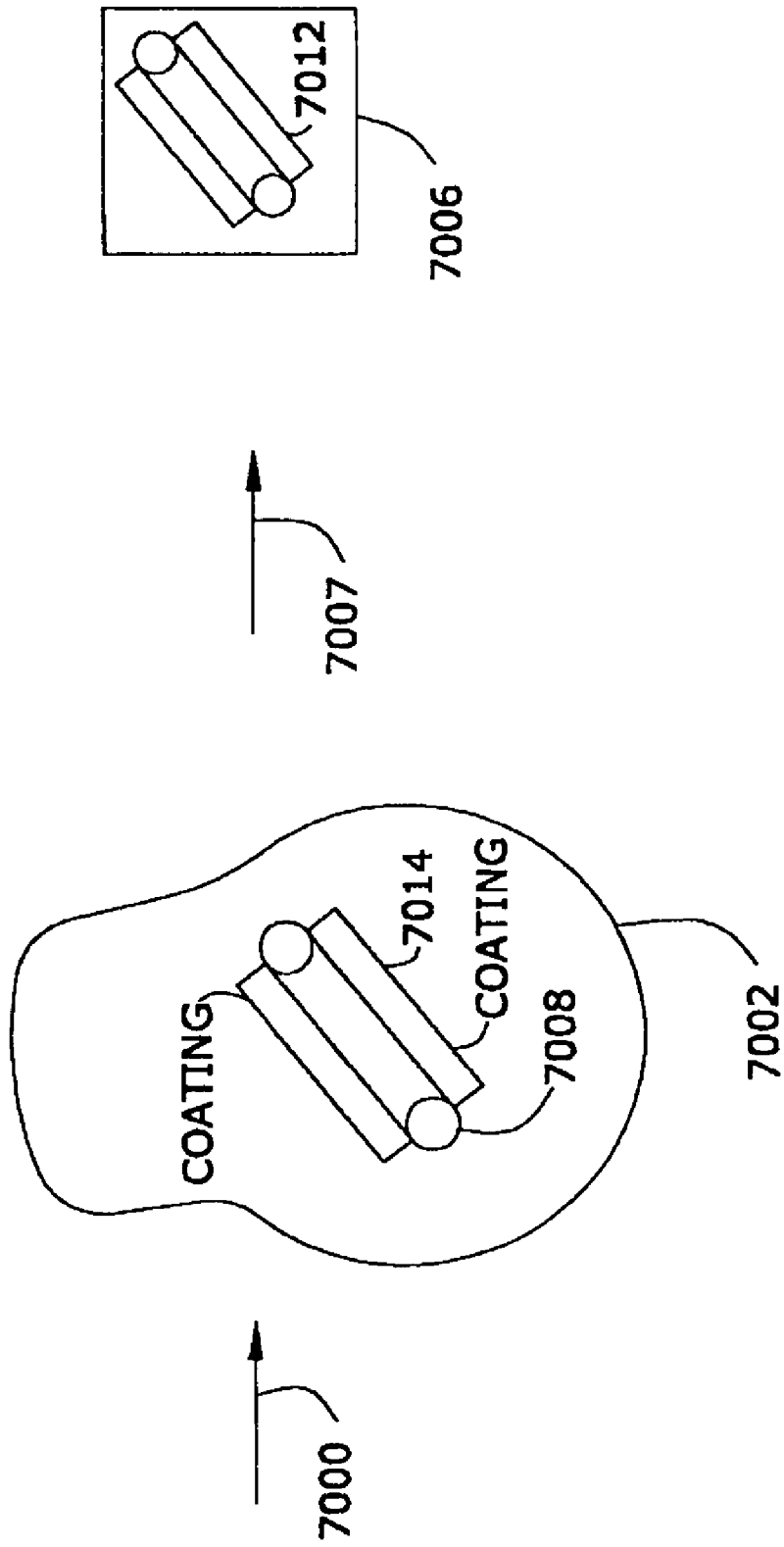

FIGS. 56A through 56C illustrate one preferred process of the invention. As is illustrated in FIG. 56A, a biological organism 7002 is shown being irradiated with electromagnetic radiation 7000 in a magnetic resonance (MR) imaging process. As a result of this irradiation, a signal 7004 that represents an undistorted image of the organism 7002 is produced; and, from this signal 7004, a displayed image 7006 is generated. This displayed image 7006 is representative of the true state of the biological organism; it contains no significant artifacts.

By comparison, and in the situation depicted in FIG. 56B, the biological organism 7002 contains disposed within it a medical device 7008. In this situation, when organism 7002 is irradiated with the MR radiation 7000, a different signal 7005 is produced; and an image of this different, distorted signal is presented in display 7006. Due to the interference caused by the medical device 7008, the image 7010 is not representative of the true state of either the biological organism 7002 or of the medical device 7008. It is said that the image 7010 is distorted by substantial image artifacts.

FIG. 56C represents the situation that occurs when the implanted medical device 7008 is coated with a nanomagnetic coating of this invention. In this case, because the "signature" of the coated medical device differs from the "signature" of the uncoated medical device, the image 7012 is less distorted by substantial image artifacts than is the image 7010; and, by proper choice of properties of the nanomagnetic coating, the image 7012 is representative of the true state of the biological organism 7002 and of the device 7008. The relative accuracy of this image 7012 is due to the fact that any interference due to medical device 7008 is mitigated by the presence of coating 7014.

To correct this problem, one may image medical device 7014 by MR radiation 7000 ex vivo, outside of the biological organism 7002. With data obtained from such imaging, the MRI may then be calibrated such that a correct waveform is generated that compensates for the presence of the device 7014. This calibration may be conducted in accordance with the formula $D=f[(M)e^{ia}]$, wherein D is the distortion, f indicates the variables that D is a function of, M is the magnitude of the electromagnetic wave, e is the natural logarithm base, i is the square root of −1, and a is a phase factor that is equal to the phase of the electromagnetic wave that is detected and displayed in the display 7006.

As is disclosed elsewhere in this specification, by the appropriate choice of materials for the nanomagnetic coating 7012, one may adjust the phase factor a so that D, as corrected, is equal to 1.

Some of the image artifact problems caused by implanted medical devices during MRI imaging are illustrated and discussed in a book by Frank G. Shellock entitled "Magnetic Resonance Procedures: Health Effects and Safety" (CRC Press, LLC, Boca Raton, Fla., 2001).

FIG. 14.4(a) of this Shellock book (at page 281) illustrates intracranial aneurysm clips, some of which contain ferromagnetic materials and, thus, are contraindicated for patients undergoing conventional MR procedures. FIG. 14.4(b) of the Shellock book illustrates the image artifacts caused by these aneurysm clips. It was noted by the author that " . . . the smallest artifacts are seen for the aneurysm clips made from titanium alloy and commercially pure titanium."

Similarly, FIG. 14.14 of the Shellock book (see page 298) illustrates a "T1-weighted, coronal plane image of the hips and pelvis obtained from a patient with a contraceptive diaphragm in place." The author urged the readers to "Note the presence of the substantial artifacts and image distortion."

As will be apparent, the process of this invention, when applied to these and other medical devices, resolves the prior art distortion problem.

In one embodiment, the radio-frequency wave produced during MRI imaging is a pulsed electromagnetic wave with a pulse duration of from about 1 microsecond to about 100 milliseconds. As is disclosed on page 70 of a book by Zhi-Pei Liang et al. entitled "Principles of Magnetic Resonance Imaging (IEEE Press, New York, N.Y., 2000), "RF pulse is a synonym of the $B_1$ field so called because the $B_1$ field is short-lived and oscillates in the radio-frequency range. Specifically, the $B_1$ field is normally turned on for a few microseconds or milliseconds . . . the $B_1$ field is much weaker (e.g., $B_1=50$ mT . . . )."

In one embodiment, the pulsed RF electromagnetic wave produced during MR imaging has a repetition rate of from about 10 to about 50,000 milliseconds. In one aspect of this embodiment, the amplitude of such pulsed RF electromagnetic wave is from about 10 microTesla to about 100 milliTesla.

The switched gradient magnetic field present during MRI imaging preferably has a rise time up to its maximum amplitude of from about 0.1 to about 2 milliseconds as the field strength rises from 0 to 10 milliTesla per meter.

Although the invention has been shown and described with respect to a preferred embodiment thereof, it should be understood by those skilled in the art that various changes and omissions in the form and detail thereof may be made therein without departing from the spirit and scope of the invention.

We claim:

1. A magnetic resonance imaging tracking assembly that comprises a medical device having a magnetic shield comprised of a layer of nanomagnetic material, means for contacting said magnetic shield with a first high frequency electromagnetic wave, means for modifying said first high frequency electromagnetic wave with said magnetic shield to produce a second high frequency electromagnetic wave, and means for transmitting said second high frequency electromagnetic wave from said layer of nanomagnetic material, wherein:

said medical device is disposed within a biological organism, said nanomagnetic material has an average particle size of less than about 100 nanometers, said layer of nanomagnetic material has a saturation magnetization of from about 200 to about 26,000 Gauss, said layer of nanomagnetic material is disposed between said first high frequency electromagnetic wave and said medical device, said layer of nanomagnetic material has a thickness of less than about 2 microns, said first high frequency electromagnetic wave has a frequency of from at least 21 megahertz to about 128 megahertz.

2. A magnetic resonance imaging tracking assembly that comprises a medical device having a magnetic shield, means for contacting said magnetic shield with a first electromagnetic wave, means for modifying said first electromagnetic wave with said magnetic shield to produce a second electromagnetic wave, and means for sensing said second electromagnetic wave wherein:

said medical device is disposed with a biological organism, said magnetic shield is comprised of a layer of said nanomagnetic material, wherein:

said layer of nanomagnetic material is disposed between said first electromagnetic wave and said medical device, said nanomagnetic material has an average particle size of less than about 100 nanometers, and said layer of nanomagnetic material has a saturation magnetization of from about 200 to about 26,000 Gauss and a thickness of less than about 10 microns.

3. A magnetic resonance imaging tracking assembly as recited in claim 2, wherein said first electromagnetic wave is a pulsed frequency electromagnetic wave.

4. A magnetic resonance imaging tracking assembly as recited in claim 3, wherein said pulsed frequency electromagnetic wave has a pulse duration of from about 1 microsecond to about 100 milliseconds.

5. A magnetic resonance imaging tracking assembly as recited in claim 2, wherein said medical device is comprised of a conductor.

6. A magnetic resonance imaging tracking assembly as recited in claim 5, wherein said conductor is flexible, having a bend radius of less than 2 centimeters.

7. A magnetic resonance imaging tracking assembly comprising:

a medical device having a magnetic shield comprised of nanomagnetic material;

means for contacting said magnetic shield with a first electromagnetic wave;

means for modifying said first electromagnetic wave to produce a second electromagnetic wave;

means for transmitting said second electromagnetic wave from the nanomagnetic material, and means for sensing said second electromagnetic wave;

said layer of nanomagnetic material having a saturation magnetization of from about 200 to about 26,000 Gauss;

said first electromagnetic wave having a frequency of from at least about 21 megahertz to about 128 megahertz.

8. A magnetic resonance imaging tracking assembly as recited in claim 7, further comprising means for producing an image from said second electromagnetic wave.

9. A magnetic resonance imaging tracking assembly as recited in claim 8, wherein said first wave is a pulsed electromagnetic wave.

10. A magnetic resonance imaging tracking assembly as recited in claim 7, further comprising means for producing said first electromagnetic wave.

11. A magnetic resonance imaging tracking assembly as recited in claim 7, further comprising means for cooling said medical device.

* * * * *